United States Patent
Goodnow, Jr. et al.

(10) Patent No.: US 9,586,916 B2
(45) Date of Patent: Mar. 7, 2017

(54) INTEGRIN ANTAGONIST CONJUGATES FOR TARGETED DELIVERY TO CELLS EXPRESSING ALPHA-V-BETA-3

(71) Applicant: Hoffmann-La Roche Inc., Nutley, NJ (US)

(72) Inventors: Robert Alan Goodnow, Jr., Gillette, NJ (US); Matthew Michael Hamilton, Hackettstown, NJ (US); Agnieszka Kowalczyk, Mine Hill, NJ (US); Achyutharao Sidduri, Livingston, NJ (US)

(73) Assignee: HOFFMANN-LA ROCHE INC., Nutley, NJ (US)

(*) Notice: Subject to any disclaimer, the term of this patent is extended or adjusted under 35 U.S.C. 154(b) by 0 days.

(21) Appl. No.: 14/374,680

(22) PCT Filed: Jan. 22, 2013

(86) PCT No.: PCT/EP2013/051082
§ 371 (c)(1),
(2) Date: Jul. 25, 2014

(87) PCT Pub. No.: WO2013/110578
PCT Pub. Date: Aug. 1, 2013

(65) Prior Publication Data
US 2015/0038523 A1 Feb. 5, 2015

Related U.S. Application Data

(60) Provisional application No. 61/591,299, filed on Jan. 27, 2012, provisional application No. 61/678,669, filed on Aug. 2, 2012.

(51) Int. Cl.
| | | |
|---|---|---|
| C07D 207/452 | (2006.01) |
| C07D 239/14 | (2006.01) |
| C07D 417/12 | (2006.01) |
| C07D 277/593 | (2006.01) |
| C07C 327/32 | (2006.01) |
| A61K 47/48 | (2006.01) |
| C07C 237/52 | (2006.01) |

(52) U.S. Cl.
CPC .... *C07D 277/593* (2013.01); *A61K 47/48061* (2013.01); *A61K 47/48092* (2013.01); *A61K 47/48215* (2013.01); *C07C 237/52* (2013.01); *C07C 327/32* (2013.01); *C07D 207/452* (2013.01); *C07D 239/14* (2013.01); *C07D 417/12* (2013.01)

(58) Field of Classification Search
CPC C07D 207/452; C07D 239/14; C07D 417/12; C07D 277/593; C07C 327/32
See application file for complete search history.

(56) References Cited

U.S. PATENT DOCUMENTS

2006/0030575 A1* 2/2006 Danthi ............... C07D 239/14
514/275

OTHER PUBLICATIONS

Chemical Abstracts Registry No. 106665-30-9, indexed in the Registry file on STN CAS Online Feb. 14, 1987.*

* cited by examiner

*Primary Examiner* — Laura L. Stockton

(57) ABSTRACT

The invention relates to compounds of formula (I): wherein $R^1$, $R^2$, and n are defined in the detailed description and claims. In particular, the present invention relates to the compounds of formula (I) for use in the manufacture and delivery of conjugated moieties such as small molecules, peptides, nucleic acids, fluorescent moieties, and polymers which are linked to alpha-V-beta-3 integrin antagonists to target cells expressing alpha-V-beta-3.

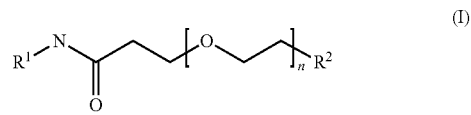

34 Claims, 10 Drawing Sheets

Fig. 1a

Table 1: Summaries of the composition of 5'-derivatized siRNA single and double strands

| Duplex-ID | Sense-ID | Sequence 5'-->3' | Antisense-ID | Sequence 5'-->3' |
|---|---|---|---|---|
| Duplex-1 | Sense-1 | GGAuGAAGuGGAGAuuAGudTsdT (Seq. Id. No. 1) | Antisense-1 | ACuAAUCUCcACUUcAUCCdTsdT (Seq. Id. No. 2) |
| Duplex-15 | Sense-15 | αVβ3 Ligand Reagent 1-(SC6)GGAuGAAGuGGAGAuuAGudTsdT (Seq. Id. No. 1) | Antisense-1 | ACuAAUCUCcACUUcAUCCdTsdT (Seq. Id. No. 2) |
| Duplex-16 | Sense-16 | αVβ3 Ligand Reagent 2-(SC6)GGAuGAAGuGGAGAuuAGudTsdT (Seq. Id. No. 1) | Antisense-1 | ACuAAUCUCcACUUcAUCCdTsdT (Seq. Id. No. 2) |
| Duplex-17 | Sense-17 | αVβ3 Ligand Reagent 6-(SC6)GGAuGAAGuGGAGAuuAGudTsdT (Seq. Id. No. 1) | Antisense-1 | ACuAAUCUCcACUUcAUCCdTsdT (Seq. Id. No. 2) |
| Duplex-18 | Sense-18 | αVβ3 Ligand Reagent 7-(SC6)GGAuGAAGuGGAGAuuAGudTsdT (Seq. Id. No. 1) | Antisense-1 | ACuAAUCUCcACUUcAUCCdTsdT (Seq. Id. No. 2) |

Fig. 1b

Table 2: Analytical Data for small molecule siRNA conjugates

| Small Molecule | Target | Number | Sequence (5'--3') | Calc. Mass | Exp. Mass | IEX % FLP |
|---|---|---|---|---|---|---|
| αVβ3-PEG8-Maleimide | Aha1 | Sense-15 | αVβ3 Ligand Reagent 1-(SC6)GGAuGAAGuGGAGAuuAGudTsdT (Seq. Id. No. 1) | 8170.5 | 8175.3 | >82.7 |
| αVβ3-PEG12-Maleimide | Aha1 | Sense-16 | αVβ3 Ligand Reagent 2-(SC6)GGAuGAAGuGGAGAuuAGudTsdT (Seq. Id. No. 1) | 8346.7 | 8349.4 | >75 |
| αVβ3-PEG8-maleimide | Aha1 | Sense-17 | αVβ3 Ligand Reagent 6-(SC6)GGAuGAAGuGGAGAuuAGudTsdT (Seq. Id. No. 1) | 8268.6 | 8270.9 | 86 |
| αVβ3-PEG12-maleimide | Aha1 | Sense-18 | αVβ3 Ligand Reagent 7-(SC6)GGAuGAAGuGGAGAuuAGudTsdT (Seq. Id. No. 1) | 8444.8 | 8447.6 | >85 |

Fig. 1c
Table 3: Summary of small molecule-siRNA conjugate potencies in integrin antagonists assays and siRNA KD data

| Targeting Element | Configuration | | | siRNA derivative | Jurkat Cells/VCAM-1 Adhesion Assay (nM) | αVβ3 Adhesion Assay (nM) | LFA1 Adhesion Assay (nM) | AHA1 % KD |
|---|---|---|---|---|---|---|---|---|
| | Small molecule Ligand Reagent | siRNA | Fluorochrome | | | | | |
| none | | AHA-1 | Duplex-1 | No | RD-03518 | > 200 | | | 98 |
| none | | AHA-1 | Duplex-1N | Nu547 | RD-05170 | > 200 | | | |
| αVβ3 Ligand 1-PEG 8 | αVβ3 Ligand Reagent 1 | Aha1 | Duplex-15 | no | RD-08412 | | 4.6 | | |
| αVβ3 Ligand 1-PEG 12 | αVβ3 Ligand Reagent 2 | Aha1 | Duplex-16 | no | RD-08413 | | 3.4 | | |
| αVβ3 Ligand 3-PEG 8 | αVβ3 Ligand Reagent 6 | Aha1 | Duplex-17 | no | RD-08414 | | 0.7 | | |
| αVβ3 Ligand 3-PEG 12 | αVβ3 Ligand Reagent 7 | Aha1 | Duplex-18 | no | RD-08415 | | 0.1 | | |
| αVβ3 small molecule | | | 141 | | | | 2 | | |
| Negative assay reference | | | FITC-22 | | | > 200 | | | |
| Negative assay reference | | | FITC-23 | | | > 200 | | | |

Fig. 1d Table 4: Identity, characterization and binding potencies of FITC isomer labeled reagents

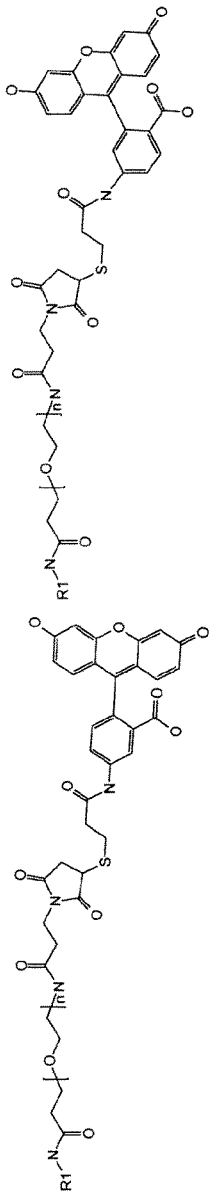

| Example | Targeting Element | Synthesis method: one pot or with corresponding targeting example | Jurkat Cells/VCAM-1 Adhesion Assay (IC50 nM) | αVβ3 Assay (IC50 nM) | LFA1 Adhesion Assay (IC50 nM) | Calc. Mass | Observed Mass |
|---|---|---|---|---|---|---|---|
| FITC-17 | αVβ3 Ligand 1-PEG12-FITC | αVβ3 Ligand Reagent 2 | | 801 | | 1685.81 | 1687.6 [M+2]+ |
| FITC-18 | αVβ3 Ligand 3-PEG12-FITC | αVβ3 Ligand Reagent 7 | | | 6 | 869.99 | 890.7 (M+2H)2+ |
| FITC-19 | αVβ3 Ligand 3-PEG8-FITC | αVβ3 Ligand Reagent 8 | | | | 803.86 | 804.5 [M+2]+ |
| FITC-20 | αVβ3 Ligand 4-PEG8-FITC | Method B (one pot) | | 7.8 | | 791.355 | 791.7855 [M+2H]+ |
| FITC-21 | αVβ3 Ligand 5-PEG8-FITC | Method B (one pot) | 9,400 | 84 | | 782.845 | 783.2784 [M+2H]2+ |
| FITC-22 | untargeted benzyl-PEG4-FITC | Method B (one pot) | >200 | | >10,000 | 941.019 | 941.3269 (M+H)+ |
| FITC-23 | untargeted benzyl-PEG8-FITC | Method B (one pot) | | | 74 | 1117.23 | 1117.4317 [M+H]+ |
| 142 | positive control | | 4 | | | | |
| 140 | positive control | | | 2 | | | |
| 141 | positive control | | | | | | |

Histograph (Red Duplex-27 500 nM and Example 140 10 µM; green Duplex -27)

Representative siRNA uptake image (Duplex-27 (500 nM)

Images of Jurkat cells with FITC conjugated with Example
FITC-5 (LFA-1 antagonist-labeled FITC) at 10 μM Images of Jurkat cells with FITC conjugated with Example
FITC-14 (VLA-4 antagonist-labeled FITC) at 10 μM

SEQUENCE LISTING

```
<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: siRNA targeting AHA1

<400> SEQUENCE: 1
ggaugaagug gagauuagut t                                             21

<210> SEQ ID NO 2
<211> LENGTH: 21
<212> TYPE: DNA
<213> ORGANISM: Artificial Sequence
<220> FEATURE:
<223> OTHER INFORMATION: siRNA targeting AHA1

<400> SEQUENCE: 2
acuaaucucc acuucaucct t                                             21
```

INTEGRIN ANTAGONIST CONJUGATES FOR TARGETED DELIVERY TO CELLS EXPRESSING ALPHA-V-BETA-3

This application is a National Stage Application of PCT/EP2013/051082 filed Jan. 22, 2013, which claims priority from Provisional Patent Application No. 61/591,299 filed on Jan. 27, 2012 and Provisional Patent Application No. 61/678,669 filed on Aug. 2, 2012.

FIELD OF THE INVENTION

The present invention relates to the synthesis and reaction of potent and selective small molecule integrin antagonists containing appropriate linkers and functional groups for chemical reaction with other molecules which contain reactive nucleophiles such as thiols such that a covalent linkage is formed between a moiety to be conjugated and the targeting entity. The small molecule targeting antagonists bind to cognate receptor systems as integrin type alpha-V-beta-3 ($\alpha V\beta 3$) receptor antagonists to the $\alpha V\beta 3$ dimer. The covalently linked moiety includes small molecule therapeutics, polymers, peptides, and oligonucleotides. Included are 5'-thio-containing oligonucleotides for formation of 5'-thio-siRNA derivatives as a means to enable targeted delivery of said siRNAs. Such derivatized siRNAs in conjunction with appropriate transfection agents aid in the selective delivery of siRNAs to cells which express such integrin receptors, thereby preventing the expression of target genes through RNA interference (RNAi).

BACKGROUND OF THE INVENTION

The integrin type $\alpha V\beta 3$ is a receptor for vitronectin [Hermann, P. et al. "The vitronectin receptor and its associated CD47 molecule mediates proinflammatory cytokine synthesis in human monocytes by interaction with soluble CD23" [The Journal of cell biology 144 (1999): 767-75]. It consists of two components, integrin alpha V and integrin beta 3 (CD61), and is expressed by platelets as well as other cell types. It has been shown that inhibitors of $\alpha V\beta 3$ like etaracizumab may be used as antiangiogenics.

RNA interference is a well-known process in which the translation of messenger RNA (mRNA) into protein is interfered with by the association or binding of complementary or partially complementary oligonucleotides such as small interfering RNA (siRNA), short hairpin RNA (shRNA), micro RNA (miRNA), or antisense oligonucleotides. siRNAs are doublestranded RNA molecules, usually ranging from 19-25 nucleotides in length that associate with a set of proteins in the cytoplasm known as RISC (RNA-induced silencing complex). RISC ultimately separates the double stranded siRNA allowing one strand to bind or associate with a complementary or partially complementary portion of an mRNA molecule after which the mRNA is destroyed by RISC or otherwise prevented from being translated—consequently suppressing the expression of the encoded protein or gene product.

One of the problems in using nucleic acids such as siRNA in therapeutic applications (especially for systemic administration in humans) has been in delivering the nucleic acids to: (1) particular target tissues or cell types and (2) to the cytoplasm of those cells (i.e., where the mRNA is present and translated into protein). Part of the delivery problem is based on the fact that nucleic acids are negatively charged and easily degraded (especially if unmodified), efficiently filtered by the kidney, and cannot be easily transported to the cytoplasm of the cells by themselves. Thus, a significant amount of research has focused on solving the delivery problem with various carriers and formulations including liposomes, micelles, peptides, polymers, conjugates and aptamers. See Ling et al, Advances in Systemic siRNA Delivery, Drugs Future 34(9): 721 (September 2009). Some of the more promising delivery vehicles have involved the use of lipidic systems including lipid nanoparticles. See Wu et al., Lipidic Systems for In Vivo siRNA Delivery, AAPS J. 11(4): 639-652 (December 2009); International Patent Application Publication No. WO 2010/042877 by Hope et al ("Improved Amino Lipids And Methods For the Delivery of Nucleic Acids"). However, a need remains for further improved targeting of siRNA; as well as substances such as small molecules, peptides, other nucleic acids, fluorescent moieties, and polymers to particular target cells and to the cytoplasm of such cells.

SUMMARY OF THE INVENTION

The invention relates to compounds of formula I:

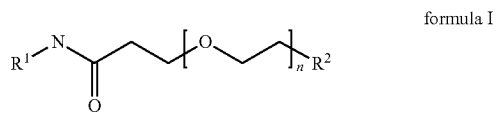

formula I wherein $R^1$, $R^2$, and n are defined in the detailed description and claims. In particular, the present invention relates to the compounds of formula I for the improved delivery of conjugated moieties such as small molecules, peptides, nucleic acids, fluorescent moieties, and polymers to target cells expressing the $\alpha V\beta 3$ dimer for various therapeutic and other applications. The present invention also relates to methods of manufacturing and using such compounds.

DETAILED DESCRIPTION OF THE INVENTION

Figure 1:
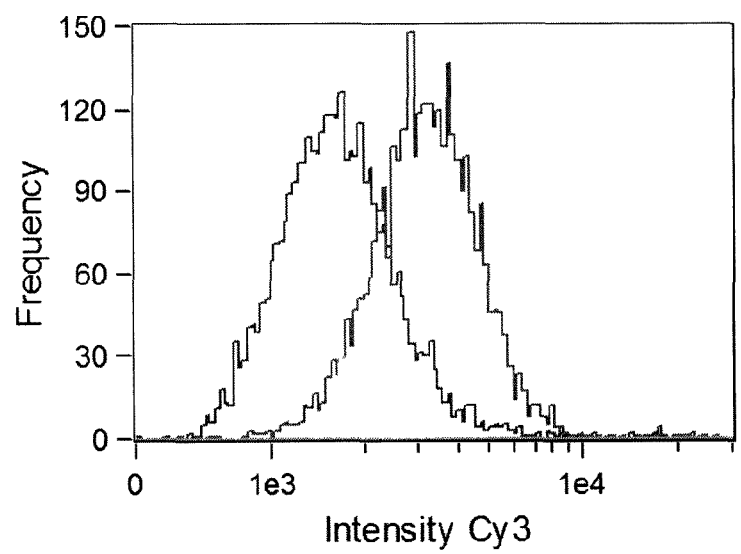
FIG. 1a): Table 1 shows the composition of particular 5'-derivatized siRNA single and double strands.
FIG. 1b): Table 2 shows analytical data for small molecule siRNA conjugates.
FIG. 1c): Table 3 shows small molecule-siRNA conjugate potencies in integrin antagonists assays and siRNA KD data.
FIG. 1d): Table 4 shows the identity, characterization and binding potencies of FITC isomer labeled reagents.
FIG. 1e) shows a histograph (Red Duplex-27 500 nM and Example 140 10 µM; green Duplex –27).
Figure 2:
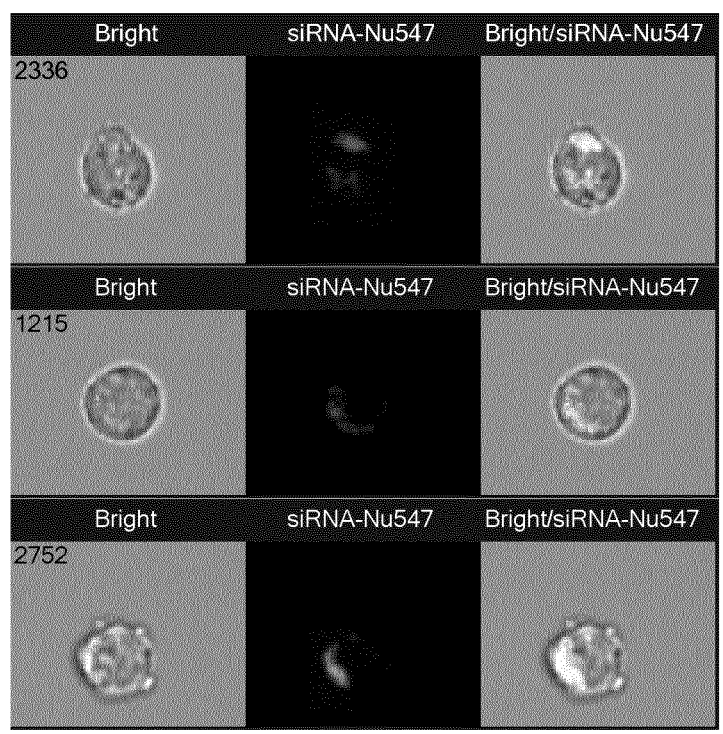
FIG. 2 shows representative siRNA uptake image (Duplex-27 (500 nM).
Figure 3:
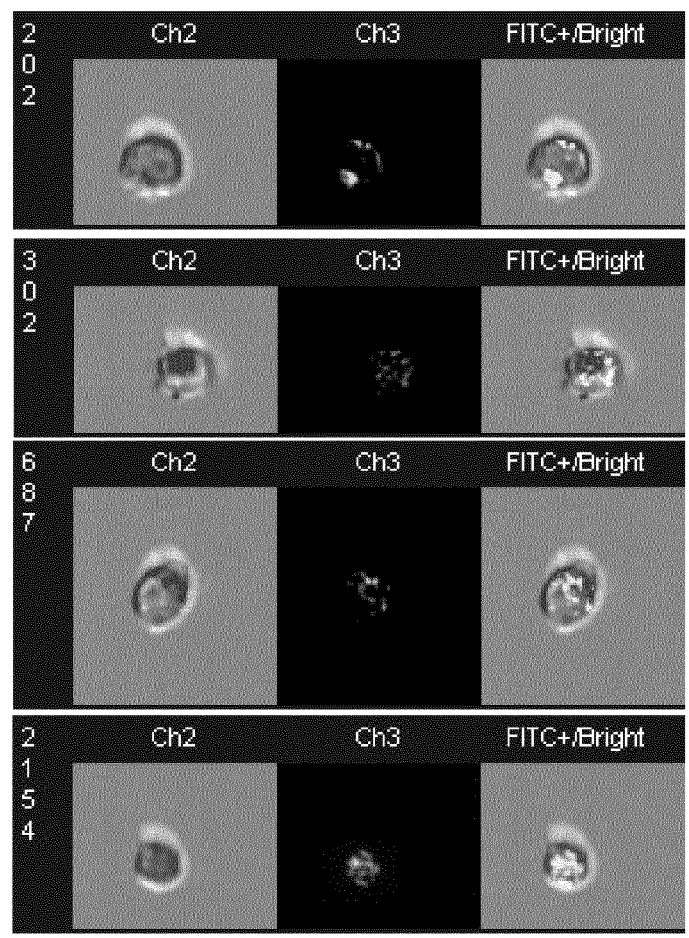
FIG. 3 shows images of Jurkat cells with FITC conjugated with Example FITC-5 (LFA-1 antagonist-labeled FITC) at 10 µM.
Figure 4:
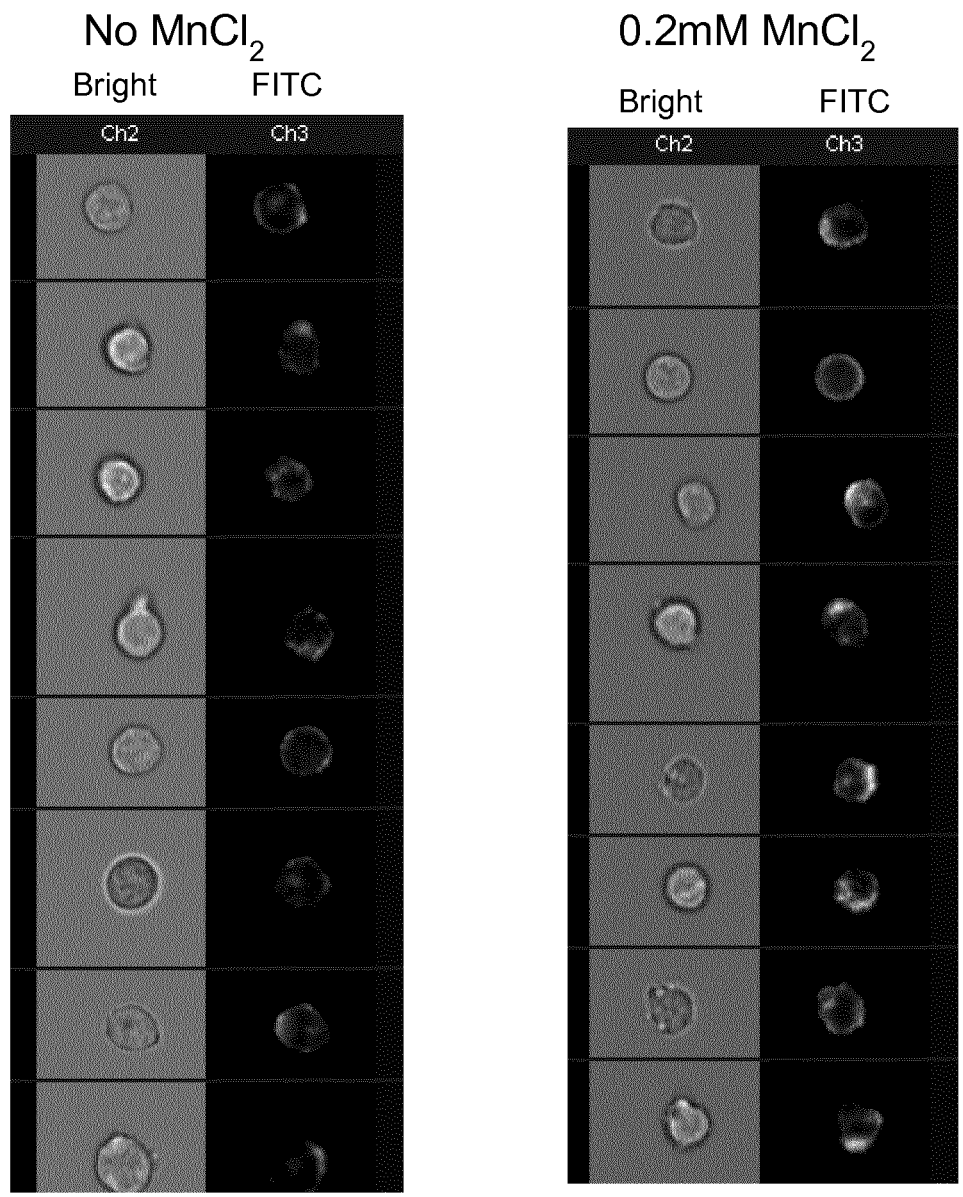
FIG. 4 shows images of Jurkat cells with FITC conjugated with Example FITC-14 (VLA-4 antagonist-labeled FITC) at 10 µM. The histograph indicates a shift in presence of the siRNA duplex with a VLA-4 targeting element. In the presence of VLA-4 antagonist example 140, this shift is oblated.

Unless otherwise indicated, the following specific terms and phrases used in the description and claims are defined as follows:

The term "moiety" refers to an atom or group of chemically bonded atoms that is attached to another atom or molecule by one or more chemical bonds thereby forming part of a molecule. For example, the variables $R^1$ and $R^2$ of formula I refer to moieties that are attached to the structure shown in formula I by a covalent bond where indicated.

The term "conjugated moiety" refers to moiety which is a therapeutic or useful compound, peptide, polymer, small molecule, fluorescent moiety, oligonucleotide or nucleic acid. Examples include drugs, therapeutic peptides, antisense oligonucleotides, siRNA, and fluorescein isothiocyanate (FITC).

Unless otherwise indicated, the term "hydrogen" or "hydro" refers to the moiety of a hydrogen atom (—H) and not $H_2$.

The term "halogen" refers to a moiety of fluoro, chloro, bromo or iodo.

The term "alkyl" denotes a monovalent linear or branched saturated hydrocarbon group of 1 to 12 carbon atoms. In particular embodiments, alkyl has 1 to 7 carbon atoms, and in more particular embodiments 1 to 4 carbon atoms. Examples of alkyl include methyl, ethyl, propyl, isopropyl, n-butyl, iso-butyl, sec-butyl, or tert-butyl.

The term "TFA" refers to trifluoroacetic acid.

Unless otherwise indicated, the term "a compound of the formula" or "a compound of formula" or "compounds of the formula" or "compounds of formula" means any compound selected from the genus of compounds as defined by the formula (including any pharmaceutically acceptable salt or ester of any such compound if not otherwise noted).

The term "pharmaceutically acceptable salts" refers to those salts which retain the biological effectiveness and properties of the free bases or free acids, which are not biologically or otherwise undesirable. Salts may be formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxalic acid, maleic acid, malonic acid, salicylic acid, succinic acid, fumaric acid, tartaric acid, citric acid, benzols acid, cinnamic acid, mandelic acid, methanesulfonic acid, ethanesulfonic acid, ptoluenesulfonic acid, N-acetylcystein and the like. In addition, salts may be prepared by the addition of an inorganic base or an organic base to the free acid. Salts derived from an inorganic base include, but are not limited to, the sodium, potassium, lithium, ammonium, calcium, and magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins and the like. Depending on the substitution patterns, the compounds of the present invention may also exist as zwitterions.

The compounds of the present invention can be present in the form of pharmaceutically acceptable salts. The compounds of the present invention can also be present in the form of pharmaceutically acceptable esters (i.e., the methyl and ethyl esters of the acids of formula I to be used as prodrugs). The compounds of the present invention can also be solvated, i.e. hydrated. The solvation can be affected in the course of the manufacturing process or can take place i.e. as a consequence of hygroscopic properties of an initially anhydrous compound of formula I (hydration).

Compounds that have the same molecular formula but differ in the nature or sequence of bonding of their atoms or the arrangement of their atoms in space are termed "isomers." Isomers that differ in the arrangement of their atoms in space are termed "stereoisomers." Diastereomers are stereoisomers with opposite configuration at one or more chiral centers which are not enantiomers. Stereoisomers bearing one or more asymmetric centers that are non-superimposable mirror images of each other are termed "enantiomers." When a compound has an asymmetric center, for example, if a carbon atom is bonded to four different groups, a pair of enantiomers is possible. An enantiomer can be characterized by the absolute configuration of its asymmetric center or centers and is described by the R- and S-sequencing rules of Cahn, Ingold and Prelog, or by the manner in which the molecule rotates the plane of polarized light and designated as dextrorotatory or levorotatory (i.e., as (+) or (-)-isomers respectively). A chiral compound can exist as either individual enantiomer or as a mixture thereof. A mixture containing equal proportions of the enantiomers is called a "racemic mixture".

The term "a therapeutically effective amount" means an amount of a compound that is effective to prevent, alleviate or ameliorate symptoms of disease or prolong the survival of the subject being treated. Determination of a therapeutically effective amount is within the skill in the art. The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. The daily dosage can be administered as a single dose or in divided doses, or for parenteral administration, it may be given as continuous infusion.

The term "pharmaceutically acceptable carrier" is intended to include any and all material compatible with pharmaceutical administration including solvents, dispersion media, coatings, antibacterial and antifungal agents, isotonic and absorption delaying agents, and other materials and compounds compatible with pharmaceutical administration. Except insofar as any conventional media or agent is incompatible with the active compound, use thereof in the compositions of the invention is contemplated. Supplementary active compounds can also be incorporated into the compositions.

In detail, the present invention relates to the compounds of formula I:

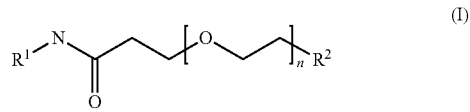

(I)

or pharmaceutically acceptable salts or esters thereof; wherein n is 1-24 and wherein: $R^1$ is selected from the group consisting of:

(1) a compound of the formula:
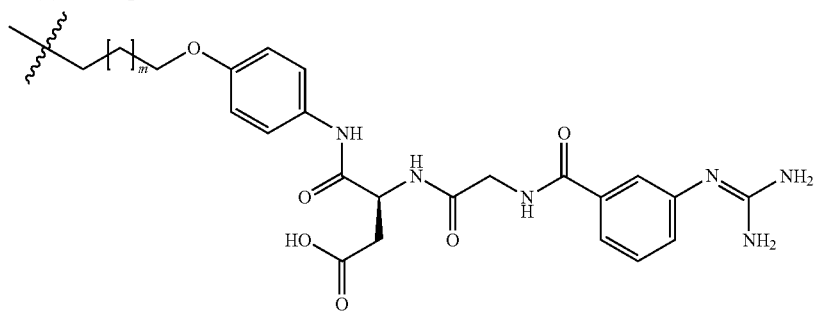
wherein m is 0 or 1;
(2) a compound of the formula:
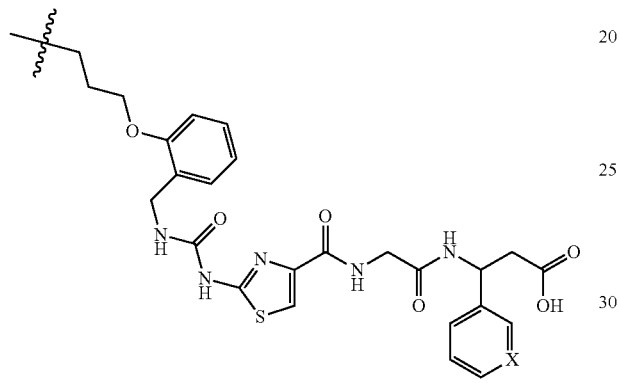
wherein X is N or CH;
(3) a compound of the formula:
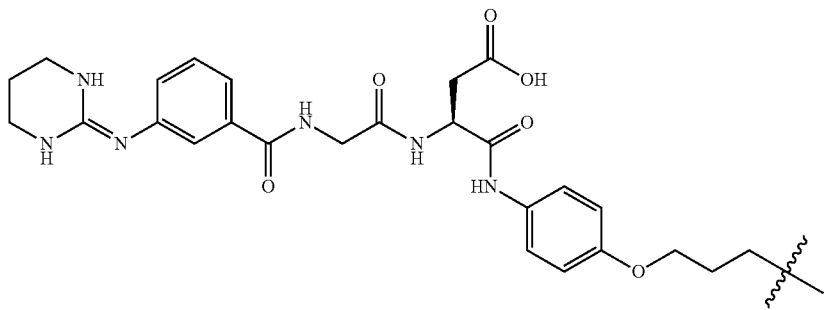 [SMILES: *CCCOc1ccc(NC(=O)[C@H](CC(=O)O)NC(=O)CNC(=O)c2cccc(N=C3NCCCN3)c2)cc1]
(4) a compound of the formula:
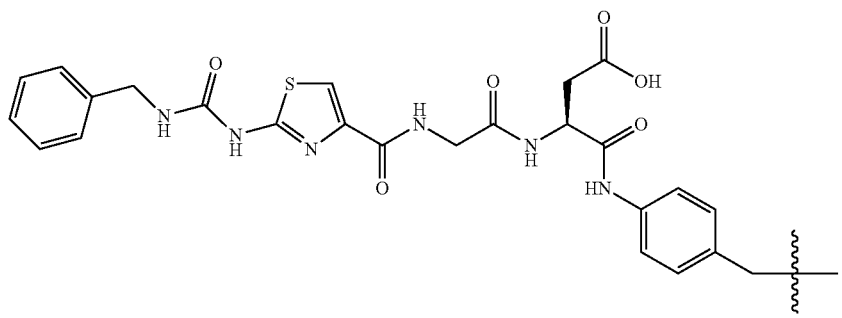 [SMILES: *Cc1ccc(NC(=O)[C@H](CC(=O)O)NC(=O)CNC(=O)c2csc(NC(=O)NCc3ccccc3)n2)cc1]

and
(5) a compound of the formula:

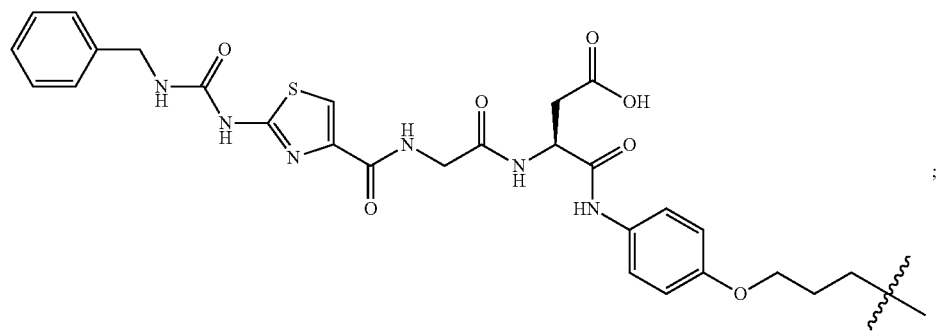 [SMILES: *CCCOc1ccc(NC(=O)[C@H](CC(=O)O)NC(=O)CNC(=O)c2csc(NC(=O)NCc3ccccc3)n2)cc1]

R² is selected from the group consisting of:
(1) a compound of the formula:

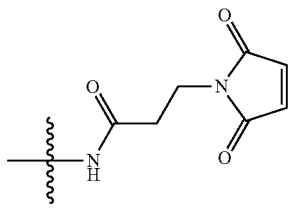 [SMILES: *NC(=O)CCN1C(=O)C=CC1=O]

(2) a compound of the formula:

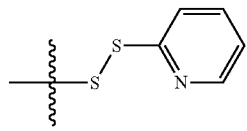 [SMILES: *SSc1ccccn1]

(3) a compound of the formula:

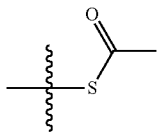 [SMILES: *SC(C)=O]

and
(4) a compound of the formula:

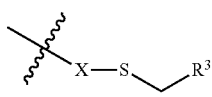

wherein R³ is a conjugated moiety and X represents either sulfur or a compound of the formula:

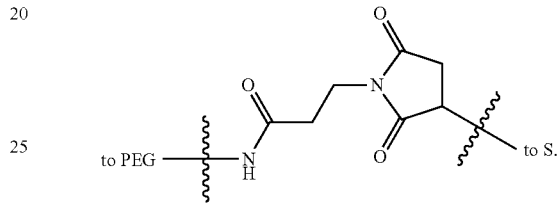

As used in the above structures, the symbol ⁂ is used to indicate where the structure or moiety is attached to the base molecule by a covalent bond. In addition, the phrase "to PEG" or "to S" or similar language used in combination with the above symbol, indicates where or how the structure or moiety is attached to the base molecule if there a multiple attachment points. For example, if R2 is a compound of the formula:

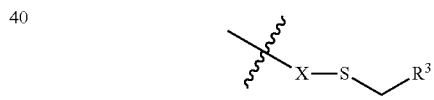

wherein X is a compound of the formula:

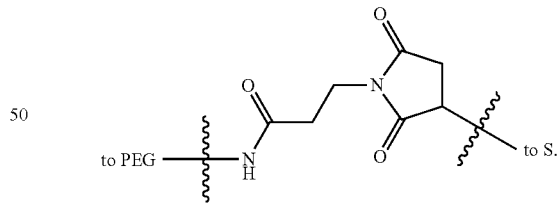

then the structure based upon formula I would be:

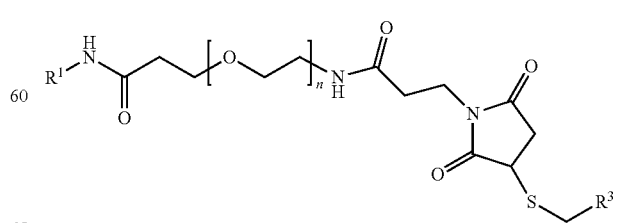

wherein R¹, R³, and n are as defined in formula I.

The present invention also relates to methods of manufacturing and using the compounds of formula I as well as pharmaceutical compositions containing such compounds. The compounds of formula I are useful in improving the delivery of small molecules, proteins, nucleic acids, polymers, fluorescent markers, and other substances to target cells expressing the αVβ3 receptor. In particular embodiments, the present invention relates to compositions and formulations containing the compounds of formula I which are useful in delivering siRNA to the cytoplasm of target cells expressing the αVβ3 receptor to inhibit the expression of certain target proteins through RNA interference.

In more particular embodiments, the invention relates to the use of the compounds of formula I for formulation to facilitate the delivery of nucleic acids such as siRNA to tumor cells and other cell types expressing αVβ3 receptors. Furthermore, the use of the compounds of formula I to synthesize delivery formulations to treat inflammation and proliferative disorders, like cancers, is part of the invention.

$R^1$ represents small molecule integrin antagonists which target the compounds of Formula I to integrin receptor complexes, thereby facilitating their delivery to cells that express such receptors.

In particular embodiments, the small molecule integrin antagonist targeting moieties of $R^1$ are attached at a position such that the affinity of binding of the small molecule to the integrin receptor is not substantially reduced relative to the free small molecule integrin antagonist. The $R^1$ moieties of formula I target the $\alpha_v\beta_3$ integrin dimer.

In particular embodiments, $R^1$ is an $\alpha_v\beta_3$ integrin targeting moiety of the formula:

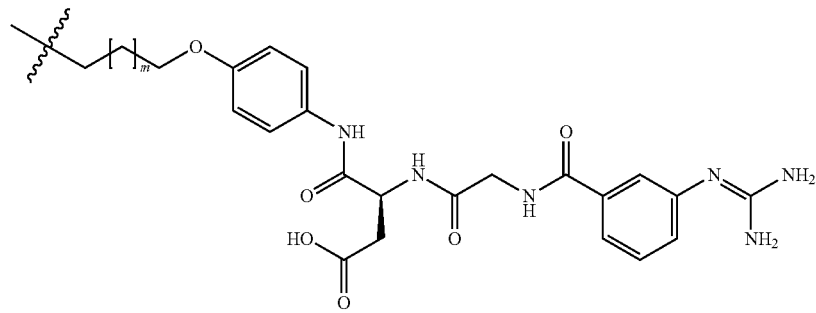

or a pharmaceutically acceptable salt or ester thereof, wherein m is 0 or 1.

In other embodiments, $R^1$ is an $\alpha_v\beta_3$ integrin targeting moiety of the formula:

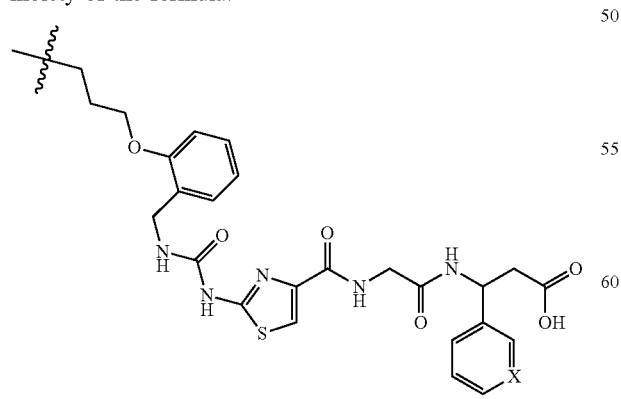

or a pharmaceutically acceptable salt or ester thereof, wherein X is N or CH.

In other embodiments, R¹ is an α$_v$β$_3$ integrin targeting moiety of the formula:

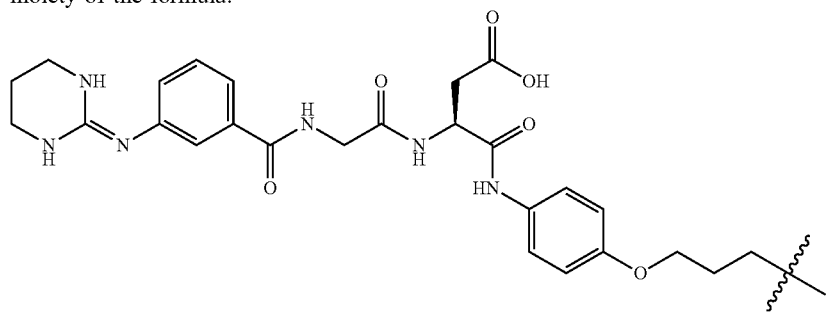

or a pharmaceutically acceptable salt or ester thereof.

In other embodiments, R¹ is an α$_v$β$_3$ integrin targeting moiety of the formula:

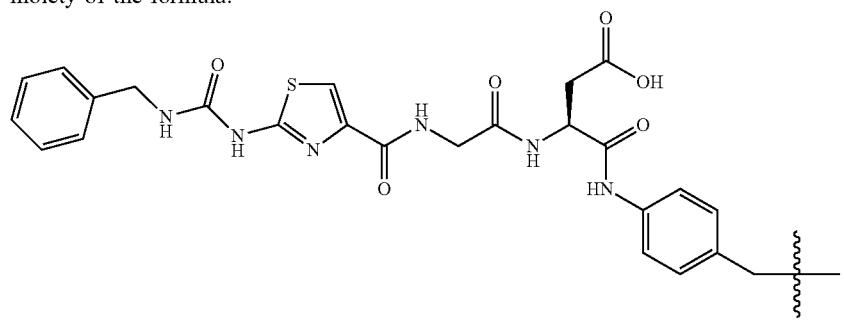

or a pharmaceutically acceptable salt or ester thereof.

In other embodiments, R¹ is an α$_v$β$_3$ integrin targeting moiety of the formula:

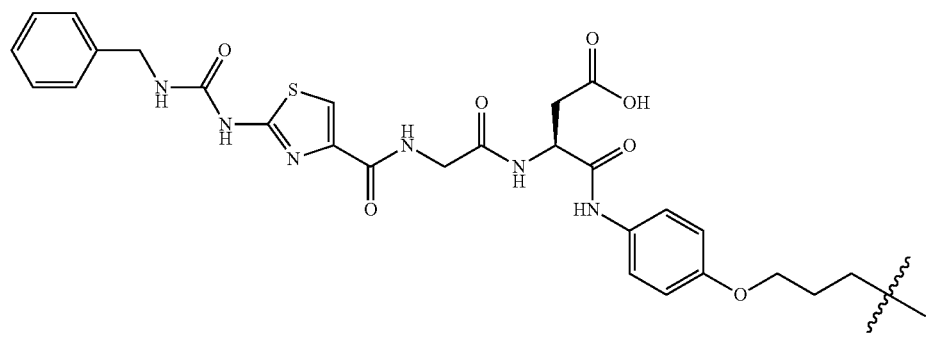 [SMILES: *CCCOc1ccc(NC(=O)[C@H](CC(=O)O)NC(=O)CNC(=O)c2csc(NC(=O)NCc3ccccc3)n2)cc1]

or a pharmaceutically acceptable salt or ester thereof.

R² may represent reactive moieties which can form covalent linkages with therapeutic or other useful compounds or conjugated moieties having strong nucleophiles such as thiol-containing molecules. Examples of such reactive moieties include moieties selected from the group consisting of:

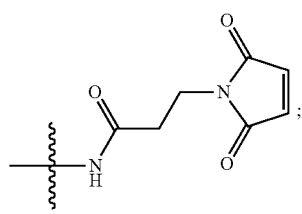

-continued

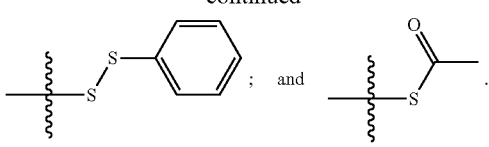

Alternatively, R² may represent a moiety which is already attached to a conjugated moiety such as a therapeutic or other useful compound, protein, or oligonucleotide (R³). More specifically, R² may represent a moiety of the formula:

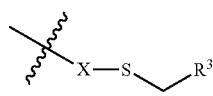

wherein R³ is a conjugated moiety and X represents either sulfur or a compound of the formula:

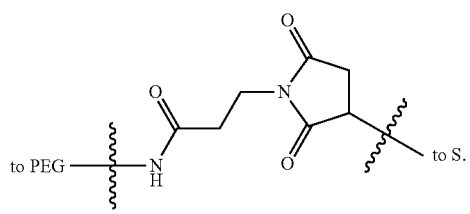 [SMILES: *NC(=O)CCN1C(=O)CC(*)C1=O]

In particular embodiments, R³ represents an oligonucleotide. In more specific embodiments, R³ represents the 5'-end of the sense strand of an RNA molecule which may exist as a single strand or in a duplex such as a siRNA molecule. Such siRNA molecules, also known as RNAi agents, inhibit the expression of a target gene in a cell. In specific embodiments, R³ is a siRNA molecule that consists essentially of an oligoribonucleotide strand of between 15 and 30 nucleotides in length, wherein the 5' terminus of the sense oligoribonucleotide strand is coupled to R² as shown in the above structures and is complementary to at least one portion of an mRNA corresponding to the target gene. In other embodiments, R³ is an oligonucleotide of DNA attached at its 5'-end. Such derivatized DNA may exist as a single strand or as one strand hybridized with a complementary strand of another oligonucleotide. The oligonucleotide strands can be either unmodified or modified for metabolic stability. Such modifications include, but are not limited to, substitutions at specific positions on the phosphate (e.g., phosphorothioate) and 2'-hydroxy (e.g., 2'-O-methyl and 2'-fluoro).

In particular embodiments, R² of formula I represents —X—S—CH₂—R³ wherein R³ includes a sense strand of RNA as shown below in formula 5 (based on formula I):

In other particular embodiments, the sense strand may be bound to an antisense strand.

In other specific embodiments, R² represents —X—S—CH₂—R³ wherein R³ represents a small molecule or protein, thereby forming a covalently linked, specifically targeted entity of formula I.

In more specific embodiments, R² represents —X—S—CH₂—R³ wherein R³ represents a therapeutic small molecule or protein.

In other specific embodiments, R² represents —X—S—CH₂—R³ wherein R³ represents a fluorescent moiety useful for the visualization of these integrin receptor bindings using cellular microscopy techniques.

In other specific embodiments, R² represents —X—S—CH₂—R³ wherein R³ represents a polymer having primary, reactive sulfides. More specifically, R3 may represent a cationic polymer useful for the complexation and delivery of siRNA to cell surfaces and the cytoplastic domains of cells.

In more particular embodiments, the present invention is directed to compounds of formula I wherein R³ is one of the structural isomers of fluorescein isothiocyanate (FITC) shown below:

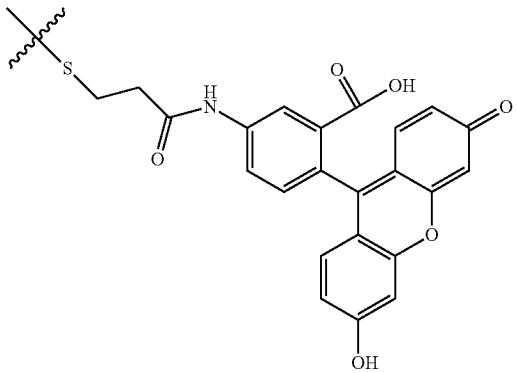

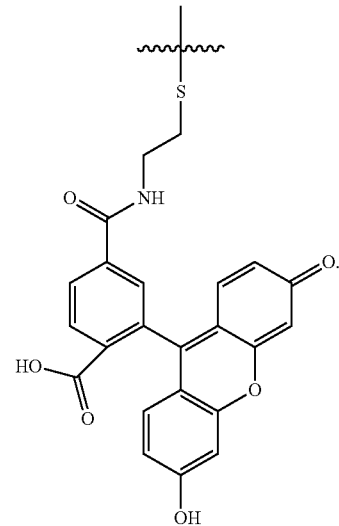

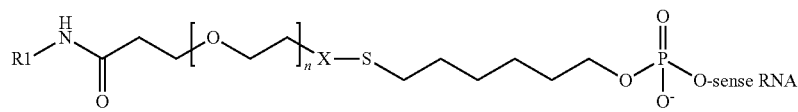

wherein R¹, n, and X are as defined in formula I.

In other more particular embodiments, the present invention is directed to compounds of formula I wherein $R^3$ is one of the structural isomers of FITC-14 shown below:

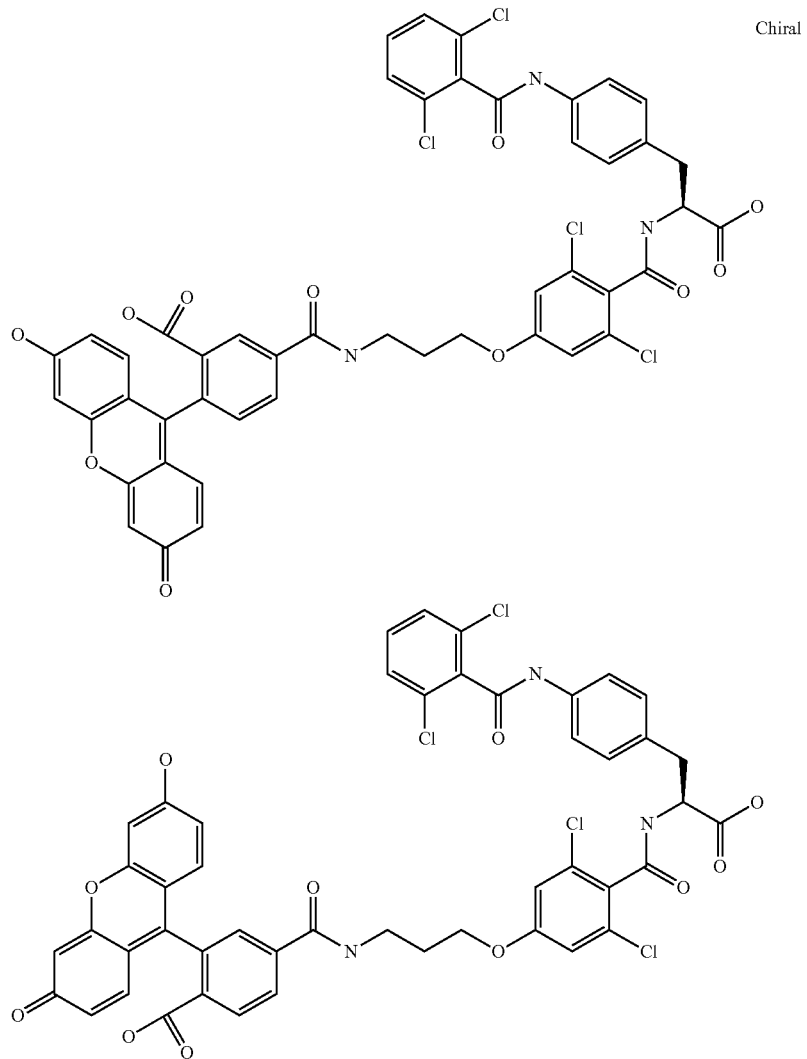

In other embodiments, the present invention is directed to a compound of formula I wherein n is 9-13, preferably 12.

In more specific embodiments, the present invention is directed to a compound of formula I selected from the group consisting of one of the following compounds (or a pharmaceutically acceptable salt or ester thereof):

αVβ3 Ligand Reagent 1: (S)—N-[4-[3-[3-[2-[2-[2-[2-[2-[2-[2-[2-[3-(2,5-dioxo-2,5-dihydro-pyrrol-1-yl)-propionylamino]ethoxy]ethoxy]ethoxy]ethoxy]ethoxy]ethoxy]ethoxy]ethoxy]-propionylamino]propoxy]-phenyl]-3-[2-[3-(guanidino)-benzoylamino]-acetylamino]-succinamic acid;

αVβ3 Ligand Reagent 2: (S)—N-[4-[3-[3-[2-[2-[2-[2-[2-[2-[2-[2-[2-[2-[2-[3-(2,5-dioxo-2,5-dihydro-pyrrol-1-yl)-propionylamino]ethoxy]ethoxy]ethoxy]ethoxy]ethoxy]ethoxy]ethoxy]ethoxy]ethoxy]ethoxy]ethoxy]-propionylamino]propoxy]-phenyl]-3-[2-[3-(guanidino)-benzoylamino]-acetylamino]-succinamic acid;

αVβ3 Ligand Reagent 3: 3:(S)—N-[[[4-[3-[2-[2-[2-[2-[2-[2-(2-acetylsulfanyl-ethoxy)ethoxy]ethoxy]ethoxy]ethoxy]ethoxy]ethoxy]ethoxy]-1-oxopropyl]amino]propoxy]-phenyl]-3-[2-[3-[guanidino-benzoylamino]-acetylamino]-succinamic acid trifluoroacetate salt; αVβ3

Ligand Reagent 4: (S)—N-[[[4-[3-[2-[2-[2-[2-[2-[2-[2-(2-acetylsulfanyl-ethoxy)ethoxy]ethoxy]ethoxy]ethoxy]ethoxy]ethoxy]ethoxy]-1-oxopropyl]amino]propoxy]-phenyl]-3-[2-[3-(tetrahydropyrimidin-2-ylideneamino)-benzoylamino]-acetylamino]-succinamic acid;

αVβ3 Ligand Reagent 5: (S)—N-[[4-[3-[2-[2-[2-[2-[2-[2-[2-[2-[2-[2-(2- acetylsulfanyl-ethoxy)ethoxy]ethoxy]ethoxy]ethoxy]ethoxy]ethoxy]ethoxy]ethoxy]ethoxy]ethoxy]ethoxy]propionylamino]methyl]phenyl]-3-[2-[[2-(3-benzylureido)thiazole-4-carbonyl]amino]acetylamino]-succinamic acid;

αVβ3 Ligand Reagent 6: (S)—N-[4-[3-[3-[2-[2-[2-[2-[2-[2-[2-[2-[3-(2,5-dioxo-2,5-dihydro-pyrrol-1-yl)-propionylamino]ethoxy]ethoxy]ethoxy]ethoxy]ethoxy]ethoxy]ethoxy]ethoxy]propionylamino]propoxy]-phenyl]-3-[2-[[2-(3-benzyl-ureido)-thiazole-4-carbonyl]-amino]-acetylamino]-succinamic acid;

αVβ3 Ligand Reagent 7: (S)—N-[4-[3-[3-[2-[2-[2-[2-[2-[2-[2-[2-[2-[2-[2-[3-(2,5-dioxo-2,5-dihydro-pyrrol-1-yl)-propionylamino]ethoxy]ethoxy]ethoxy]ethoxy]ethoxy]

ethoxy]ethoxy]ethoxy]ethoxy]ethoxy]ethoxy]ethoxy] propionylamino]ethoxy]-phenyl]-3-[2-[[2-(3-benzyl-ureido)-thiazole-4-carbonyl]-amino]-acetylamino]-succinamic acid;

αVβ3 Ligand Reagent 8: (S)—N-[4-[3-[3-[2-[2-[2-[2-[2-[2-[2-[2-acetylsulfanyl-ethoxy]ethoxy]ethoxy]ethoxy] ethoxy]ethoxy]ethoxy]ethoxy]propionylamino]propoxy]-phenyl]-3-[2-[[2-(3-benzyl-ureido)-thiazole-4-carbonyl]-amino]-acetylamino]-succinamic acid;

αVβ3 Ligand Reagent 9: (R)-3-[2-{(2-[3-{2-[3-(3-(2-{2-[2-(2-Acetylsulfanyl-ethoxy}-ethoxy)-ethoxy]-ethoxy}-pro-pionylamino)-propoxy]-benzyl}-ureido]-thiazole-4-car-bonyl)amino}-acetylamino]-phenyl-3-yl-propionic acid;

αVβ3 Ligand Reagent 10: 3-[2-{(2-[3-{2-[3-(3-{2-[2-(2-{2-[2-(2-{2-[2-(2-{2-[2-(2-Acetylsulfanyl-ethoxy)-ethoxy]-ethoxy}-ethoxy)-ethoxy]-ethoxy}-ethoxy)-ethoxy]-ethoxy}-ethoxy)-ethoxy]-ethoxy}-propionylamino)-propoxy]-benzyl}-ureido]-thiazole-4-carbonyl)amino}-acetylamino]-phenyl-3-yl-propionic acid;

αVβ3 Ligand Reagent 11: (R)-3-[2-{(2-[3-{2-[3-(3-(2-{2-[2-(2-Acetylsulfanyl-ethoxy}-ethoxy)-ethoxy]-ethoxy}-propionylamino)-propoxy]-benzyl}-ureido]-thiazole-4-carbonyl)amino}-acetylamino]-3-pyridin-3-yl-propionic acid;

αVβ3 Ligand Reagent 12: (R)-3-[2-{(2-[3-{2-[3-(3-{2-[2-(2-{2-[2-(2-{2-[2-(2-Acetylsulfanyl-ethoxy)-ethoxy]-ethoxy}-ethoxy)-ethoxy]-ethoxy}-ethoxy)-ethoxy]-ethoxy}-propionylamino)-propoxy]-benzyl}-ureido]-thiazole-4-carbonyl)amino}-acetylamino]-3-pyridin-3-yl-propionic acid;

In addition, the present invention relates to novel compositions and formulations containing compounds of formula I for the creation of nanoparticles upon combination with siRNA, resulting in the improved delivery of nucleic acids such as siRNA to the cytoplasm of target cells expressing αVβ3 dimers. In particular embodiments, the present invention is directed to a siRNA formulation comprising: (1) a compound of formula I wherein $R^2$ includes a 5'-siRNA oligonucleotide; and (2) a polycationic transfection agent.

The present invention also relates to methods of manufacturing and using such compounds and compositions. The compounds of formula I are useful as components of compositions or formulations which improve the delivery of drugs, nucleic acids, or other therapeutic compounds to tissues or cells expressing αVβ3 dimers. In particular embodiments, the present invention relates to formulations containing the compounds of formula I which are useful in delivering siRNA to the cytoplasm of target cells αVβ3 dimers to inhibit the expression of certain proteins through RNA interference. In more particular embodiments, the present invention relates to the compounds of formula I and compositions containing such compounds that can effectively deliver siRNA to tumor cells and other cell types expressing αVβ3 dimers for the treatment of cancer or inflammatory diseases. Such compounds and compositions are more efficacious and demonstrate improved knockdown capability compared to similar formulations lacking the compounds of formula I.

GENERAL SYNTHESIS OF THE COMPOUNDS OF THE INVENTION

Suitable processes for synthesizing compounds of formula I are provided in the examples. Generally, compounds of formula I can be prepared according to the schemes illustrated below. Unless otherwise indicated, the variables n and $R^1$ and $R^2$ in the schemes below are defined in the same manner as defined previously for the genus of formula I.

General Synthesis of Maleimide-(PEG)n-Integrin Antagonists Conjugating Agents

Compounds such as 26 in scheme 1 of various lengths of PEG are commercially available (e.g., from Pierce BioScience). Such compounds can also be made as by acylating the amino termini of PEG amino acids with 3-(2,5-dioxo-2,5-dihydro-pyrrol-1-yl)-propionic acid under amide bond forming conditions, followed by formation of reactive N-hydroxysuccinic esters by reaction of N-hydroxy succinic acid under ester forming conditions. As shown in scheme 1, reacting the compounds of 26 with compounds containing primary or secondary amines such as 27 are conducted in aprotic or protic solvents in the presence of basic amines such as DIEA (diisopropylethylamine) at room temperature generating the PEGylated intermediates of 28.

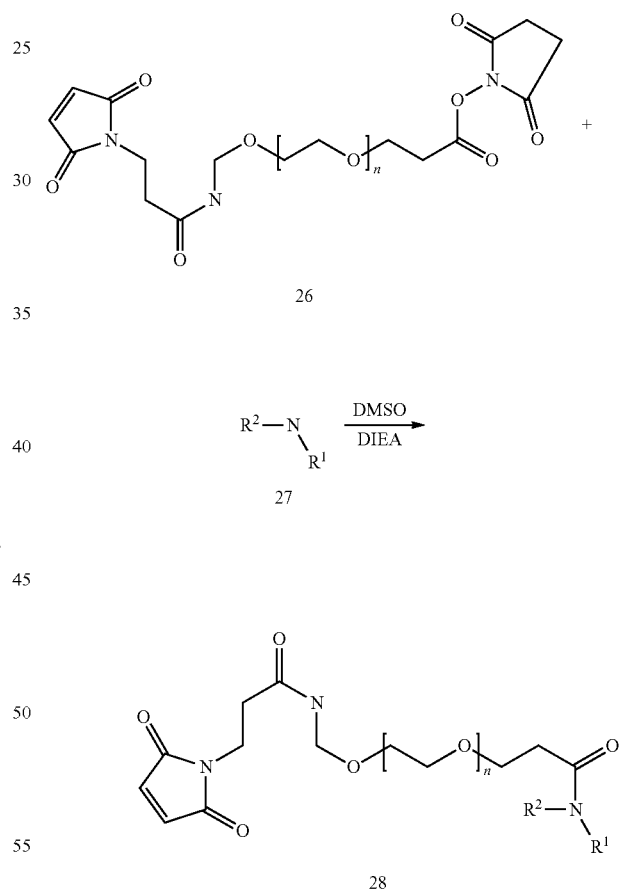

Scheme 1

Compounds such as 29 in scheme 2 for which $R^4$ is thioacetyl or 2-dithiopyridyl and having PEG moieties of various lengths are also commercially available (e.g., from Pierce BioScience). Reaction of compounds having the structure of 29 with compounds containing primary or secondary amines such as 27 are conducted in aprotic or protic solvents in the presence of basic amines such as DIEA (diisopropylethylamine) at room temperature generating the PEGylated intermediates of 30.

Scheme 2
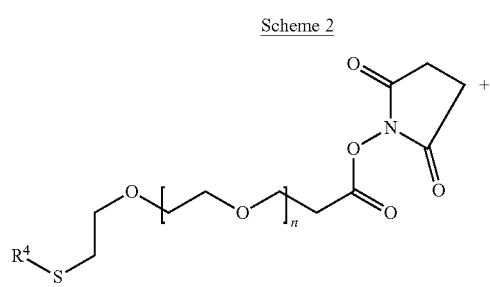
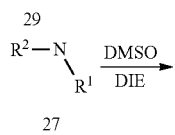
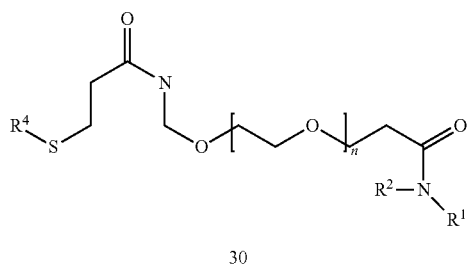
As a specific not limiting example for this invention, intermediate 26 is reacted with 31 to produce the maleimide intermediate of 32 as shown in Scheme 3:
Scheme 3
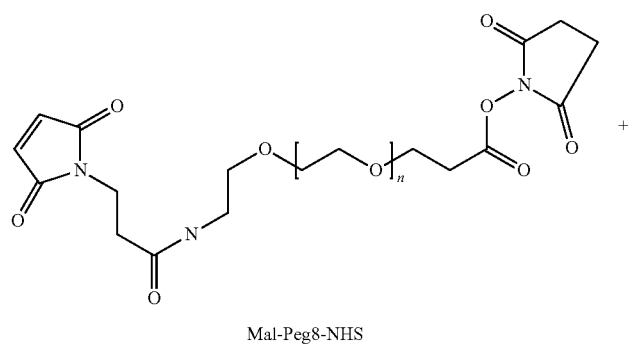
Mal-Peg8-NHS
26
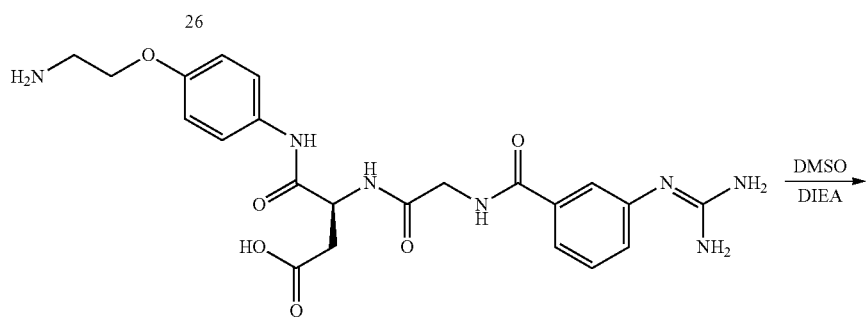
31
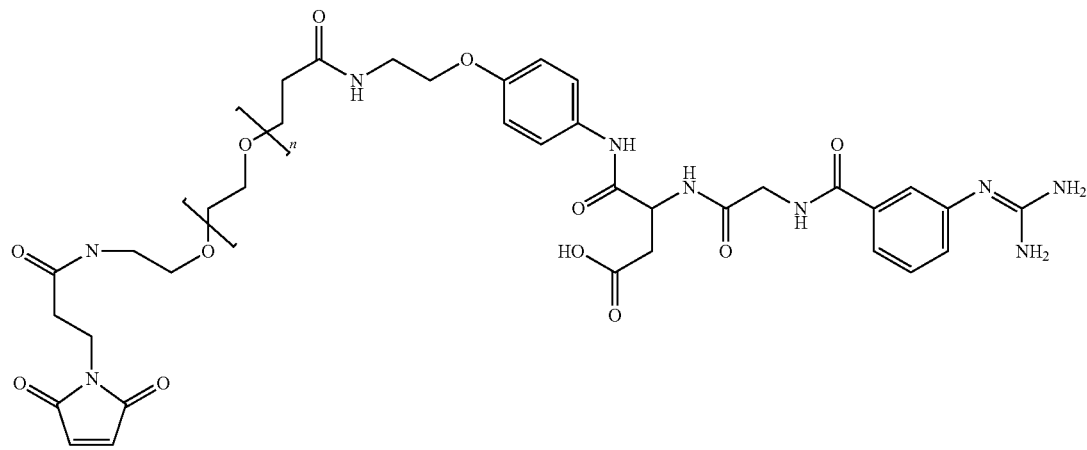
32

In a similar manner, intermediate 26 can be reacted with 33 to produce the maleimide intermediate of 34 as shown in Scheme 4:
Scheme 4
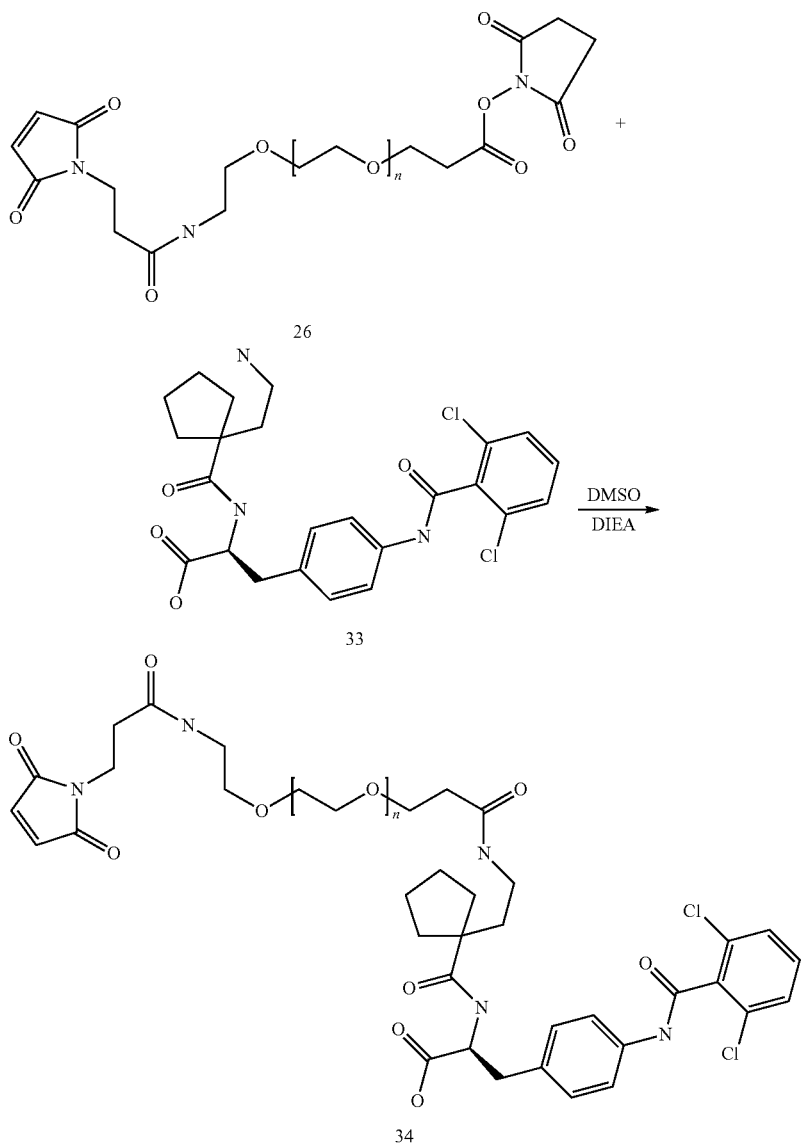
In a similar manner, intermediate 29 can be reacted with 35 to produce the intermediate of 36 as shown in Scheme 5 in which $R^4$ represents either thioacetyl or 2-dithiopyridyl:
Scheme 5
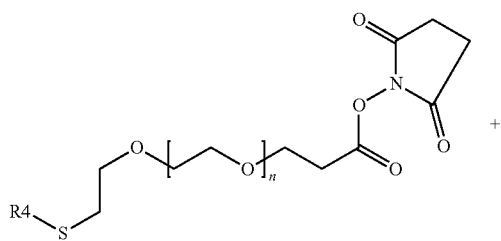

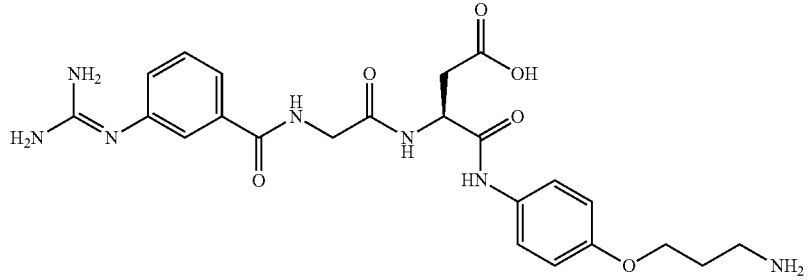
35
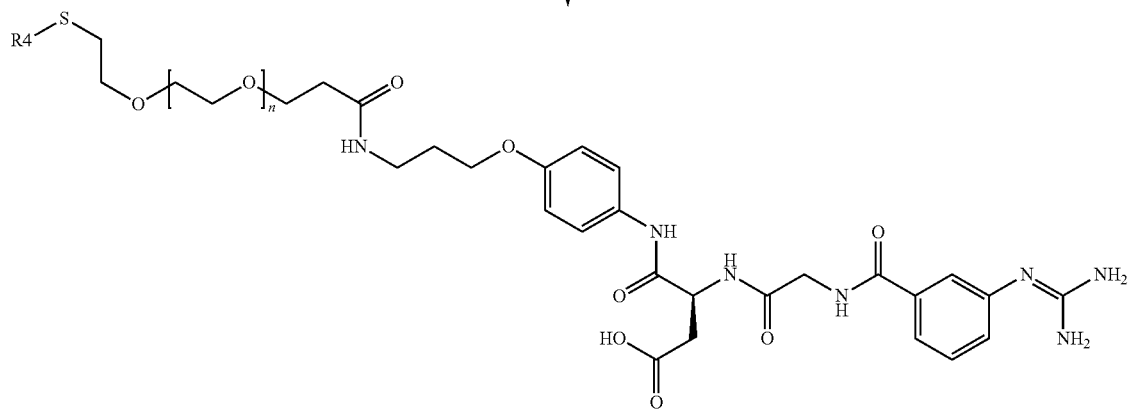
36
In a similar manner, intermediate 29 can be reacted with 37 to produce intermediate of 38 as shown in Scheme 6 in which R⁴ represents either thioacetyl or 2-dithiopyridyl:
Scheme 6
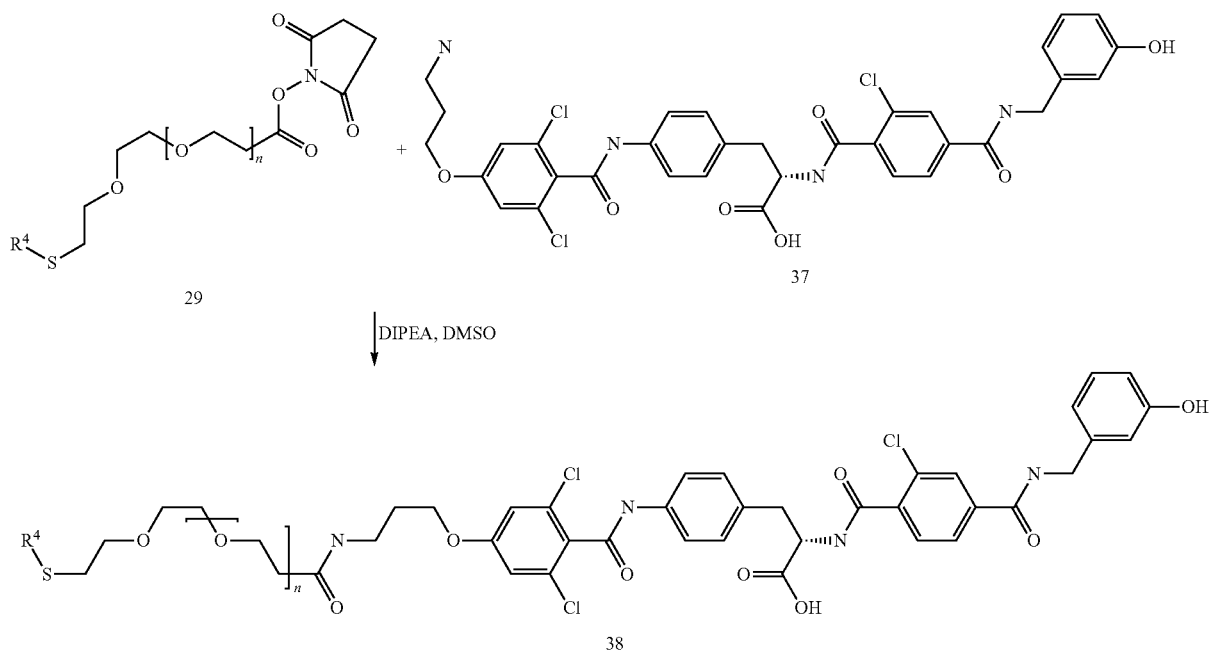

For compounds of general structure 26 or 29, different PEG lengths are available or easily made by those skilled in the art; preferably n=8-24. This topic has been thoroughly reported and reviewed (e.g., Chemistry for peptide and protein PEGylation, Advanced Drug Delivery Reviews Volume 54, Issue 4, 17 Jun. 2002, Pages 459-476).

Intermediate 31 can be synthesized in a manner similar to that which has been reported (e.g., Sidduri, A. et al. Bioorganic & Medicinal Chemistry Letters, 2002, 12, 2475-2478) as shown in Scheme 7:

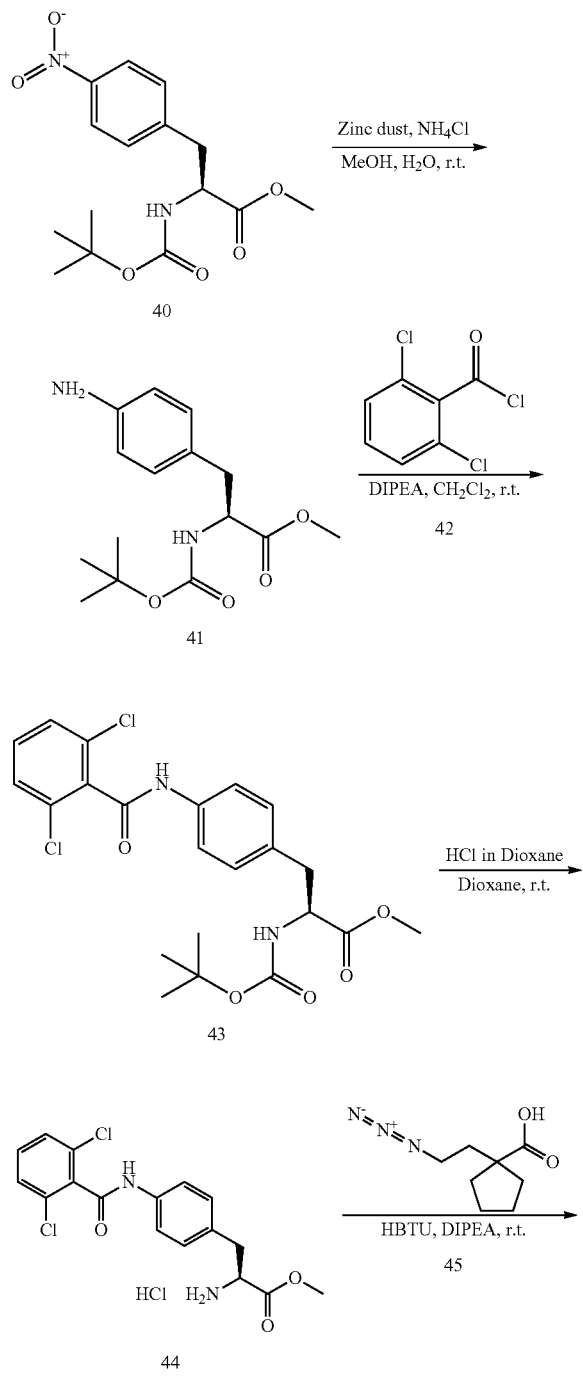

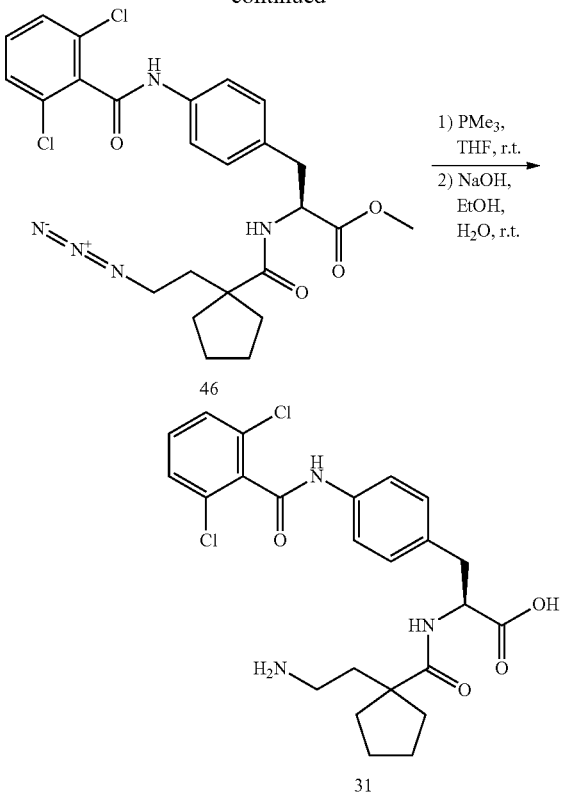

Specifically, as shown in Scheme 7, intermediate 41 was created from commercially available (S)-3-[4-nitrophenyl]-2-tert-butoxycarbonylamino-propionic acid 40. The nitro group of commercially available starting material 40 in a methanol solution was reduced with zinc dust in the presence of ammonium chloride at room temperature over the course of several hours, resulting in aniline 41. Other methods for nitro reduction are known to those skilled in the art. Aniline 41 was acylated with benzoyl halide derivatives such as 2,6-dichlorobenzoyl chloride 42 in aprotic solvent such as dichloromethane in the presence of a base such as di-isopropyl-ethyl amine at room temperature. In this manner, amide 43 was formed. The t-butylcarbonyl (Boc) amine protecting group was removed according to standard methods known to those skilled in the art, such as by treatment with an HCl solution in dioxane at room temperature; this resulted in hydrochloride 44. Hydrochloride 44 was treated with amide bond forming conditions (also well known to those skilled in the art) in the presence of known 1-(2-azido-ethyl)-cyclopentanecarboxylic acid 45 resulting in the production of di-amide 46. The azide group of intermediate 46 was reduced by treatment with tri-alkyl phosphine in an aprotic solvent such as tetrahydrofuran at room temperature. Further, the methyl ester was saponified by treatment with sodium hydroxide in a solvent mixture such as ethanol and tetrahydrofuran at an elevated temperature such as 50° C. and for 15 hours. This process resulted in the formation of intermediate 31 which may also be presented as a zwitterion.

Attachment of the PEG moiety is also possible with intermediate 39, which is synthesized as shown in Scheme 8. Specifically, 3,5-dichlorophenol 47 is protected with tri-isopropylsilylchloride in the presence of a base such as imidazole in a polar aprotic solvent such as DMF before reaction with a strong base such as butyl lithium in anhydrous tetrahydrofuran at low temperatures such as −78 degrees C. The resulting lithium complex is quenched with carbon dioxide added in the form of dry ice resulting in intermediate 48, a benzoic acid derivative. Intermediate 48 is then chlorinated to form the acyl chloride by treatment in an aprotic solvent such as toluene with sulfonyl chloride ($SOCl_2$). At this time, the acyl chloride is then reacted with amine hydrochloride 49 in the presence of base such as di-isopropylethyl amine (DIPEA) in aprotic solvent such as dichloromethane (DCM), thereby forming intermediate 50. The silyl protecting group of intermediate 50 is removed by treatment with tetrabutyl ammonium fluoride (TBAF) in a protic solvent such as tetrahydrofuran at room temperature. This phenol intermediate is reacted in the presence of a base such as potassium carbonate ($K_2CO_3$) in an aprotic solvent such as dimethylformamide (DMF) with 3-N-t-butyl-carbomate-1-bromopropane. In this manner intermediate 52 is formed which upon deprotection with trifluoroacetic acid (TFA) and subsequent hydrolysis with a base such as sodium hydroxide in protic solvent such as ethanol forms intermediate 39:

Scheme 8

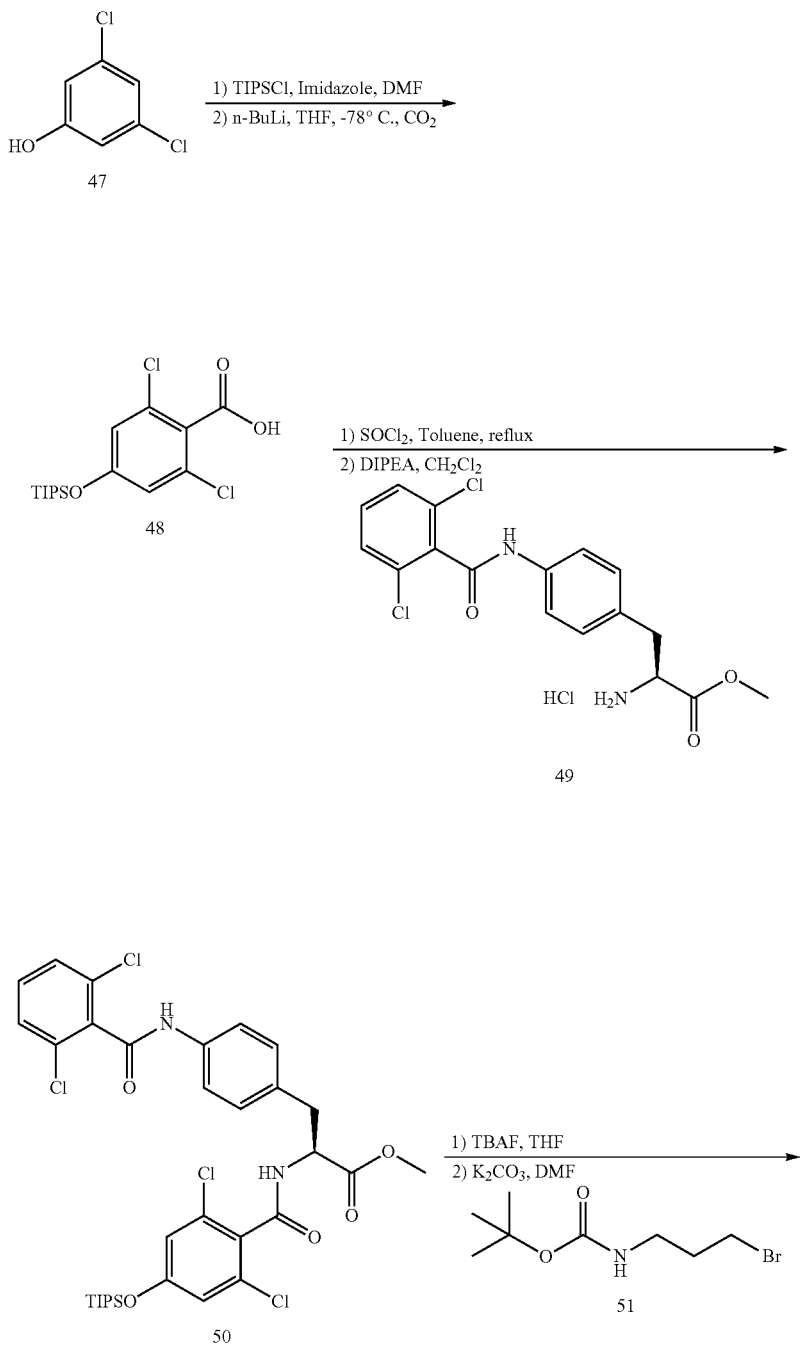

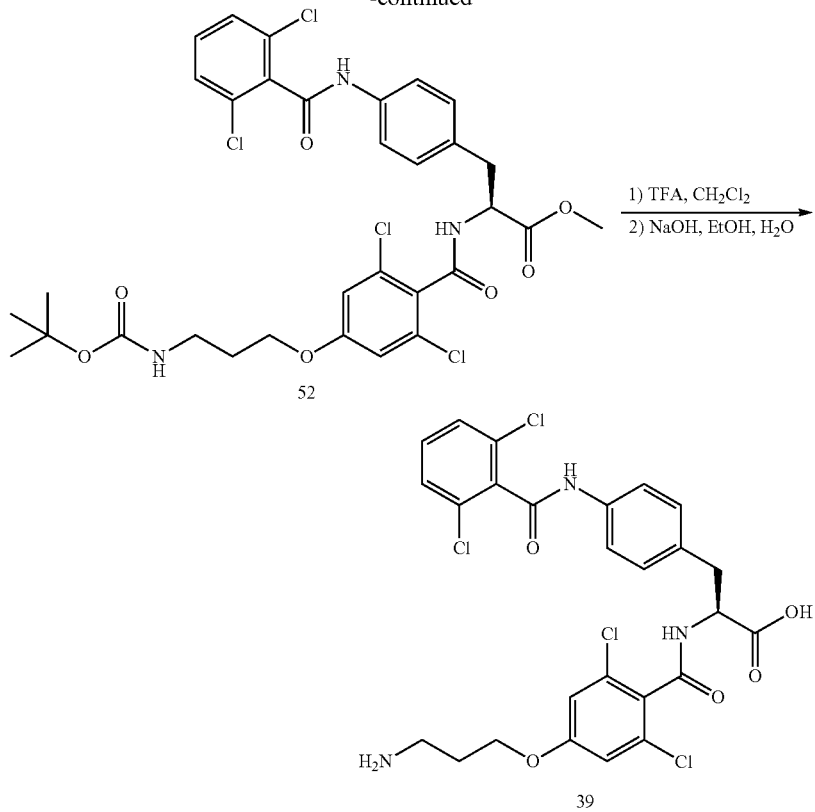

Synthesis of αVβ3 Antagonists Derivatizing Agents

Intermediate 117, an αVβ3 targeting module, can be synthesized as shown in the Scheme 15 below. Briefly, meta-aminobenzoic acid 110 is reacted with N,N-di-Boc-methylthiourea 111 in DMF, dichloromethane, and pyridine in the presence of mercuric acetate. At this point, benzyl ester protected glycine is coupled to the carboxylic acid of the product of the above reaction under standard peptide forming conditions. The benzyl ester is removed by hydrogenolysis conditions, thereby providing the free acid 112. In a separate reaction sequence, para-nitrophenol 113 is coupled with (2-hydroxy-ethyl)carbamic acid tert-butyl ester in the presence of triphenyl phosphine and diisopropyl azodicarboxylate in an aprotic solvent such as tetrahydrofuran. The nitro group of this product is reduced to the corresponding aniline 114, to which is coupled under amide bond forming conditions to N-α-Fmoc-L-aspartic acid β-tert-butyl ester. After removal of the amino protecting group Fmoc by treatment with piperidine, the amino terminus is coupled to intermediate 115 again under standard amide bond forming conditions to form Intermediate 116. Upon treatment with a strong acid, such as trifluoroacetic acid, intermediate 117 is formed and isolated by purification methods well known to those skilled in the art (e.g. preparative HPLC).

Scheme 15

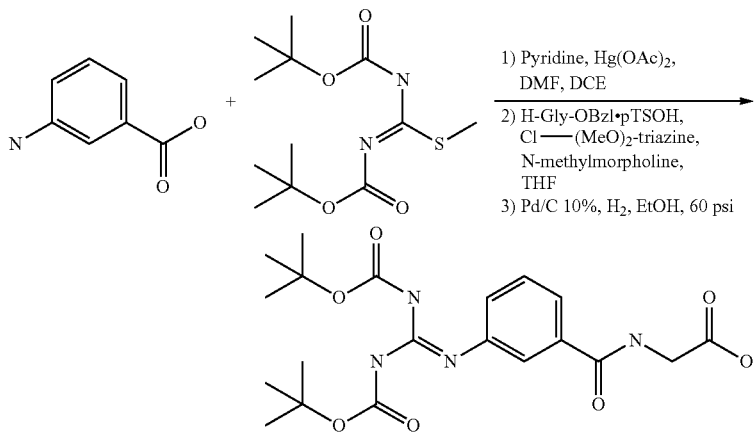

-continued

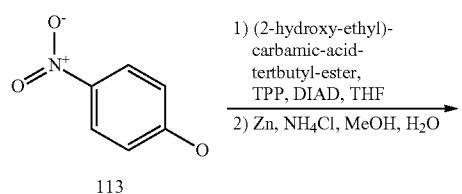

113

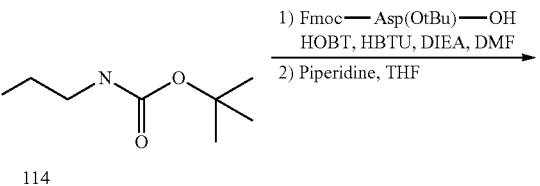

114

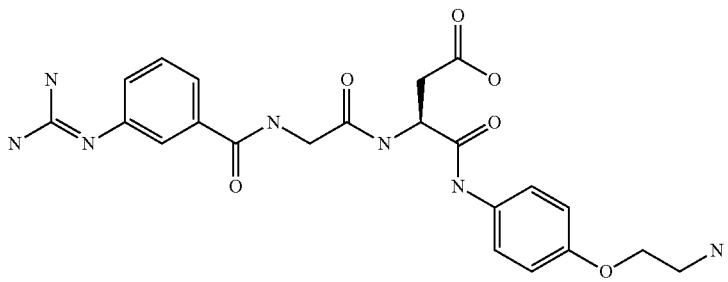

115

116

117

The 3-carbon chain amine analogue of 117 can be prepared in a similar manner as shown in Scheme 15 using (3-bromopropyl)carbamic acid tert-butyl ester instead of (2-hydroxyethyl)carbamic acid tert-butyl ester.

Other αVβ3 targeting modules can be synthesized as shown in the Scheme 16 below. [(2-amino-thiazole-4-carboxylic acid methyl ester 120 has been reported (Amide derivatives and their preparation and use as pesticides, By Kobayashi, Yumi; Daido, Hidenori; Katsuta, Hiroyuki; Nomura, Michikazu; Tsukada, Hidetaka; Hirabayashi, Atsushi; Takahashi, Yusuke; Aoki, Yoji; Kawahara, Atsuko; Fukazawa, Yasuaki; et al US Pat. Appl. Publ. (2011), US 20110201687 A1 20110818). Intermediate 120 is reacted under stand amide bond forming conditions with alanine methyl ester hydrochloride 121 thereby creating ester intermediate 122. Separately, tert-butyl 3-(2-(aminomethyl)phenoxy)propylcarbamate 129 is produced by reaction of N-(2-hydroxybenzyl)acetamide 127 in an aprotic solvent such as DMF with tert-butyl 3-bromopropylcarbamate 124 in the presence of a base such as potassium carbonate. The amino group of intermediate 129 is revealed by treatment with hydrazine hydrate. The resulting free amine 130 is treated with triphosgene to create isocyanate 131, which is combined with [(2-Amino-thiazole-4-carbonyl)-amino]-acetic acid methyl ester 132 in an aprotic solvent such as DMF producing intermediate 133. Transformation of the methyl ester of Intermediate 133 is achieved under standard saponification conditions, followed by coupling with commercially available methyl 3-amino-3-phenylpropanoate hydrochloride 146 or enantiomerically pure isomers of methyl 3-amino-3-(3-pyridyl)propanoate hydrochloride 147 and 148 under standard amide bond forming reaction conditions, thereby forming intermediate 135. The Boc protecting group is removed under standard conditions to form the αVβ3 targeting small molecule 136.

Reaction Scheme 16 for the Following Examples:

αVβ3 Ligand Reagent 9, αVβ3 Ligand Reagent 10, αVβ3 Ligand Reagent 11, and αVβ3 Ligand Reagent 12:

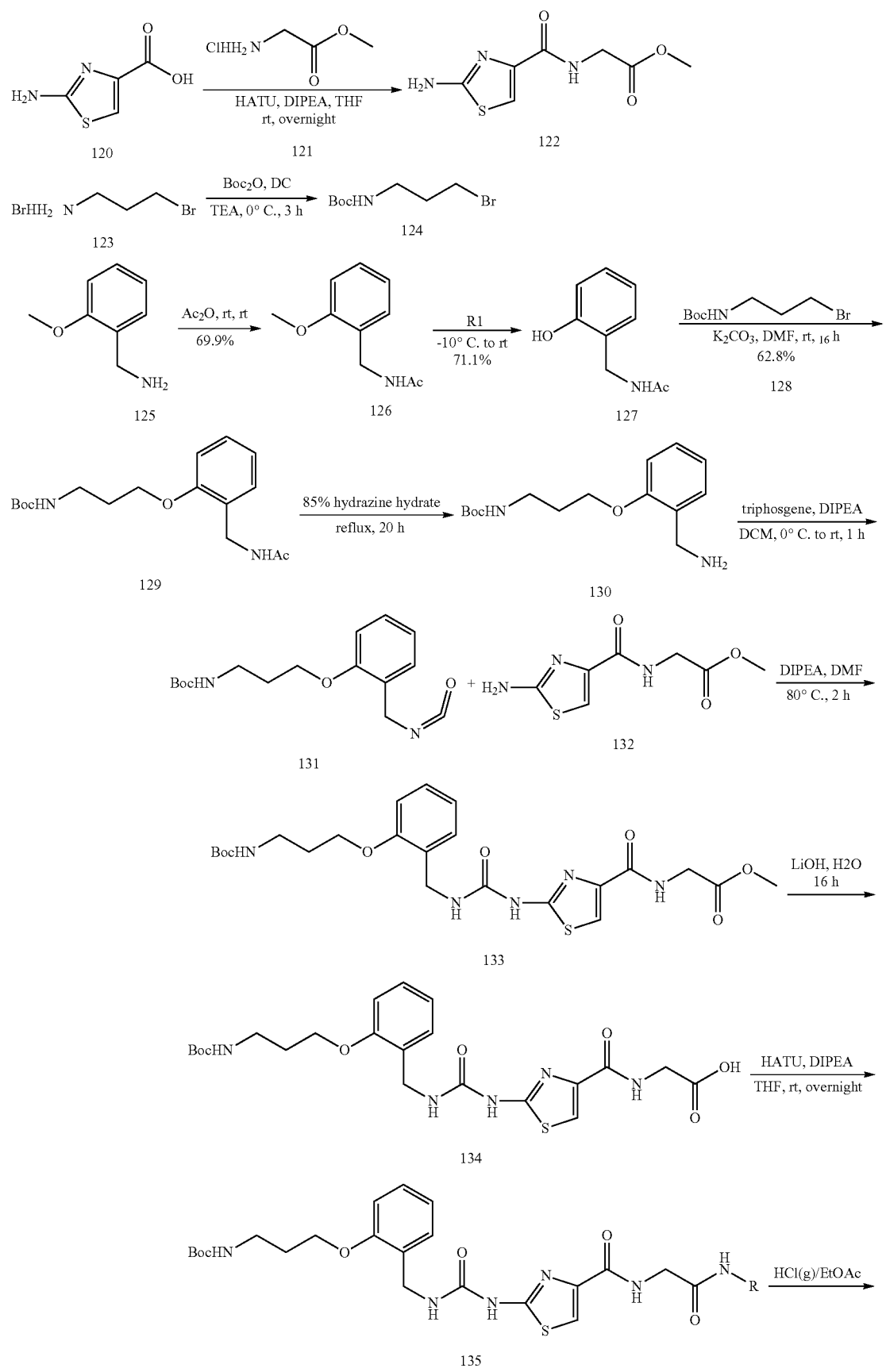

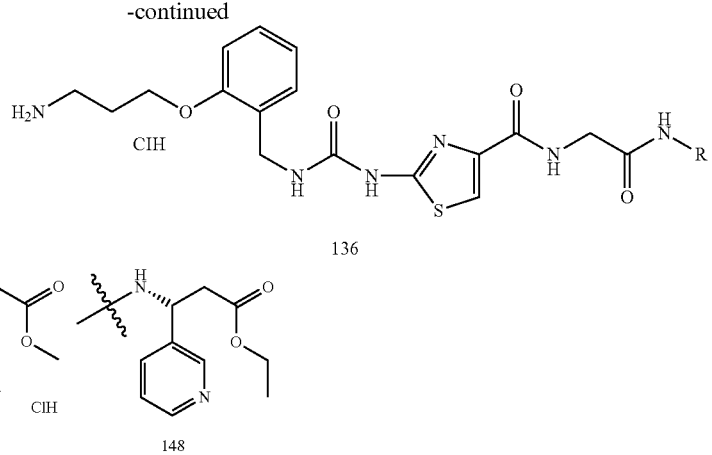

UTILITY

The compounds of formula I are useful in delivering conjugated moieties such as therapeutics, small molecules, peptides, nucleic acids, fluorescent moieties, and polymers to target cells expressing αVβ3 integrin receptor complexes for various therapeutic and other applications. Accordingly, the compounds of formula I may be used for treating various diseases and conditions that are associated with the expression or overexpression of αVβ3. Such diseases and conditions may include inflammation, cancer, and metabolic related diseases.

In particular embodiments, the present invention comprises a method of treating or preventing cancer in a mammal (preferably a human) in need of such treatment, wherein the method comprises administering a therapeutically effective amount of a compound of formula I. Such compositions can be administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "effective amount" of the compound to be administered will be governed by such considerations as the minimum amount necessary to treat or prevent the disease or condition (e.g. inhibit the expression of a target protein) and avoid unacceptable toxicity. For example, such amount may be below the amount that is toxic to normal cells, or the mammal as a whole. The compositions containing a compound of formula I of the invention may be administered by parenteral, intraperitoneal, and intrapulmonary administration. Parenteral infusions include intramuscular, intravenous, intraarterial, intraperitoneal, or subcutaneous administration.

EXAMPLES

The invention will be more fully understood by reference to the following examples. They should not, however, be construed as limiting the scope of the invention.

Reagents were purchased from Aldrich, Sigma, and Pierce BioScience or other suppliers as indicated below and used without further purification. The purification of multi-milligram to multi-gram scale was conducted by methods known to those skilled in the art such as elution of silica gel flash column. Preparative flash column purifications were also affected in some cases by use of disposable pre-packed multigram silica gel columns (RediSep) eluted with a CombiFlash system. Biotage™ and ISCO™ are also flash column instruments that may be used in this invention for purification of intermediates.

For the purpose of judging compound identity and purity, LC/MS (liquid chromatography/mass spectroscopy) spectra were recorded using the following system. For measurement of mass spectra, the system consists of a Micromass Platform II spectrometer: ES Ionization in positive mode (mass range: 150-1200 amu). The simultaneous chromatographic separation was achieved with the following HPLC system: ES Industries Chromegabond WR C-18 3u 120 Å (3.2×30 mm) column cartridge; Mobile Phase A: Water (0.02% TFA) and Phase B: Acetonitrile (0.02% TFA); gradient 10% B to 90% B in 3 minutes; equilibration time of 1 minute; flow rate of 2 mL/minute. In some cases, ammonium acetate at 20 millimolar concentration was used as a modifier for effective ionization during preparative HPLC. In such cases, the ammonium salt was isolated.

For some separations, the use of super critical fluid chromatography may also be useful. Super critical fluid chromatography separations were performed using a Mettler-Toledo Minigram system with the following typical conditions: 100 bar, 30° C., 2.0 mL/min eluting a 12 mm AD column with 40% MeOH in super critical fluid $CO_2$. In the case of analytes with basic amino groups, 0.2% isopropyl amine was added to the methanol modifier.

Compounds were characterized either by $^1$H-NMR using a Varian Inova 400 MHz NMR Spectrometer or a Varian Mercury 300 MHz NMR Spectrometer as well as by high resolution mass spectrometry using a Bruker Apex-II high-resolution 4.7T FT-Mass Spectrometer. Final compounds were also characterized by high resolution mass spectrometry using a LTQ CL Orbitrap sold by Thermo Electron.

Abbreviations used herein are as follows:
AIBN 2,2'-azobisisobutyronitrile
Bu butyl
DCE 1,2-dichloroethane
DCM dichloromethane
DBU 1,8-diazabicyclo[5.4.0]undec-7-ene
DIAD diisopropyl azodicarboxylate
DIEA diethylamine
DIPEA diisopropylethylamine
DMF N,N-dimethylformamide
DMSO dimethylsulfoxide
EDC-HCl 1-ethyl-3-(3-dimethyllaminopropyl)carbodiimide hydrochloride EtOAc ethyl acetate
EtOH ethyl alcohol
FCC flash column chromatography
h hour
HBTU O-(benzotriazol-1-yl)-N,N,N',N'-tetramethyluroniumhexafluorophosphate
HOBt hydroxybenzotriazole
HPLC high pressure liquid chromatography
HRMS high resolution mass spectra
LRMS low resolution mass spectra
LC liquid chromatography
L-Pro L-proline
MCPBA meta-chloroperoxybenzoic acid
MeOH methyl alcohol
MW microwave
NIS N-iodosuccinimide
NBS N-bromosuccinimide
NMP 1-methyl-2-pyrrolidinone
PdCl2(dppf) [1,1'-Bis(diphenylphosphino)ferrocene]dichloropalladium(II)
PEGn Polyethylene glycol repeating n times (e.g., PEG2=—OCH$_2$CH$_2$OCH$_2$CH$_2$—)
PG protecting group
PyBroP bromo-tris-pyrrolidino-phosphonium hexafluorophosphate
rt room temperature
TBAF tetrabutylammonium fluoride
TBDMS tert-butyl-dimethylsilyl
TBTU 2-(1H-benzotriazole-1-yl)-1,1,3,3-tetramethyluronium tetrafluoroborate
TMS trimethylsilyl
TEA triethylamine
TFA trifluoroacetic acid
THF tetrahydrofuran
TLC thin layer chromatography
TPP triphenylphosphine Synthesis Of Compounds Targeting αVβ3

Example 1

(S)—N-[4-[3-[3-[2-[2-[2-[2-[2-[2-[2-[2-[3-(2,5-dioxo-2,5-dihydro-pyrrol-1-yl)-propionylamino]ethoxy]ethoxy]ethoxy]ethoxy]ethoxy]ethoxy]ethoxy]-propionylamino]propoxy]-phenyl]-3-[2-[3-(guanidino)-benzoylamino]-acetylamino]-succinamic acid; αVβ3 Ligand Reagent 1

Step 1: Preparation of 3-(N,N-bis-tert-butoxycarbonylguanidino)-benzoic acid

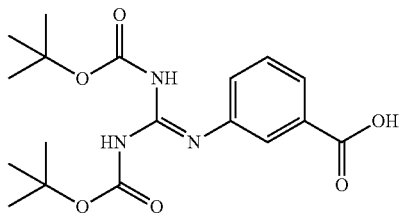

A solution of the 3-aminobenzoic acid (82.3 g, 0.60 mole), N,N'-bis(tert-butoxycarbonyl)-S-methylisothiourea (1,3-di-boc-2-methylisothiourea, CAS #107819-90-9) (174.2 g, 0.6 mole), and pyridine (94.92 g, 97 mL, 1.20 mole, 2.0 equivalents) in a mixture of anhydrous dimethylformamide (600 mL) and anhydrous 1,2-dichloroethane (600 mL) was treated with mercuric acetate (95.6 g, 0.30 mole, 0.5 equivalents) and stirred with overhead mechanical stirrer for 5 h at room temperature. Then, the solids were filtered off, washed with dichloromethane and the combined filtrate and washings were evaporated to afford the crude product (~307 g). To this crude material methanol (240 mL) was added and the mixture was stirred vigorously for 2 h. Then, slowly add 2400 mL of water while stirring vigorously. Filter, wash the solids thoroughly with water and suck dry overnight to obtain the 3-(N,N-bis-tert-butoxycarbonylguanidino)-benzoic acid in more than theoretical yield. Pump dry on high vac.

The weight obtained was over the theoretical value (theoretical=227.6 g, actual=251.2 g 1H NMR implies ~10% of DMF present).

Step 2: Preparation of 2-(3-(N,N-bis-tert-butoxycarbonylguanidino)benzoyl)-amino-acetic acid benzyl ester

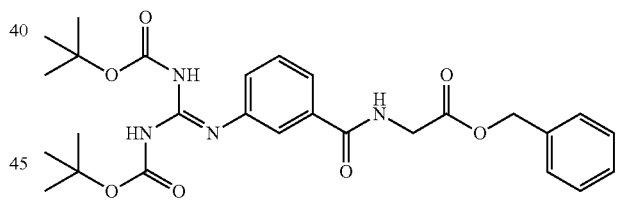

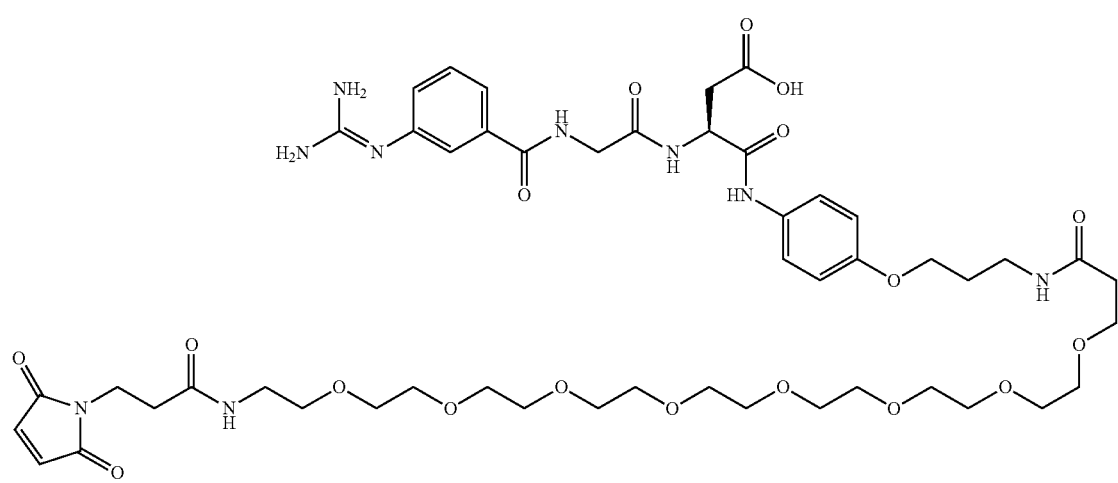 [SMILES: NC(N)=Nc1cccc(C(=O)NCC(=O)N[C@@H](CC(=O)O)C(=O)Nc2ccc(OCCCNC(=O)CCOCCOCCOCCOCCOCCOCCOCCOCCNC(=O)CCN3C(=O)C=CC3=O)cc2)c1]

A light brown solution of 3-(N,N-bis-tert-butoxycarbonylguanidino)benzoic acid (171.56 g, 0.4073 mole), 2-chloro-4,6-dimethoxy-triazine (71.52 g, 0.4073 mole), and N-methylmorpholine (41.2 g, 44.78 mL, 0.4073 mole) in anhydrous tetrahydrofuran (1600 mL) was stirred (overhead mechanical stirrer) for 2 h at room temperature and then the glycine benzylester p-TsOH salt (137.44 g, 0.4073 mole) and a second equivalent of N-methylmorpholine (41.2 g, 44.78 mL, 0.4073 mole) were added. The resulting mixture was stirred at room temperature for 36 h. Then, the tetrahydrofuran was removed on the rotary evaporator and ethyl acetate (2000 mL) was then added. The resulting mixture was washed successively with ice cold 0.5 N HCl (3×1000 mL), water (1×1000 mL), 5% aqueous sodium carbonate (1×1000 mL), water (1×1000 mL), saturated aqueous sodium chloride (1×1000 mL) and dried over sodium sulfate. The solids were filtered off, and the solvent was evaporated to afford the crude product (228.5 g) as an oil. The crude material was purified by chromatography on the Waters Prep500 (10 runs) using dichloromethane:hexane:ethyl acetate in a ratio of 40:45:15 as the eluent, to afford 2-(3-(N,N-bis-tert-butoxycarbonylguanidino)benzoyl)-amino-acetic acid benzyl ester (79.3% yield). (Note: on the first runs obtained 152 g of clean material and 33 g of slightly impure material which was rechromatographed in two runs). ES(+)-HRMS m/e calcd. for C27H34N4O7 (M+H)+527.2500, obsd. 527.2499.

Step 3: Preparation of 2-(3-(N,N-bis-tert-butoxycarbonylguanidino)benzoyl)-amino-acetic acid

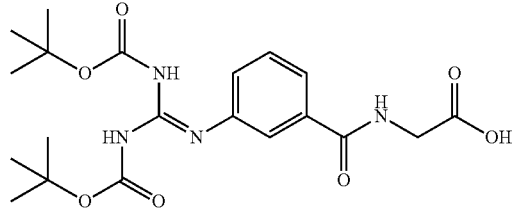 [SMILES: CC(C)(C)OC(=O)NC(=Nc1cccc(C(=O)NCC(=O)O)c1)NC(=O)OC(C)(C)C]

A solution of 2-(3-(N,N-bis-tert-butoxycarbonylguanidino)benzoyl)-amino-acetic acid benzyl ester (170.0 g, 0.323 mole) in absolute ethanol (2000 mL) was hydrogenated over 10% Pd on carbon (20 g wet catalyst, which contains ~50% water) at 60 psi overnight (18 h) in the High Pressure facility at room temperature. The catalyst was filtered off, and solvent was evaporated to afford the product. The product was azeotrophed with toluene (3 times) to remove all the ethanol, to afford 2-(3-(N,N-bis-tert-butoxycarbonylguanidino)benzoyl)-amino-acetic acid (97.88% yield) as a white solid. ES(+)-HRMS m/e calcd. for C20H28N4O7 (M+H)+437.2031, obsd. 437.2030.

Step 4: Preparation of [3-(4-nitro-phenoxy)-propyl]-carbamic acid tert-butyl ester

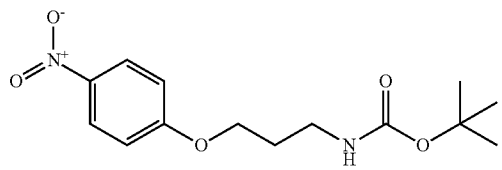 [SMILES: CC(C)(C)OC(=O)NCCCOc1ccc([N+](=O)[O-])cc1]

To a solution of (3-hydroxy-propyl)-carbamic acid tert-butyl ester (7.03 g, 40.1 mmol) in anhydrous THF (40 mL) were added 4-nitrophenol (5.07 g, 36.5 mmol), triphenylphosphine (10.5 g, 40.1 mmol) at room temperature under nitrogen atmosphere. The resulting solution was cooled to ~0° C. with an ice-water bath and then diisopropyl azodicarboxylate (DIAD, 8.1 g, 40.1 mmol) was added drop-wise for 15-20 minutes. After addition, the solution was warmed to room temperature and stirred for 15 h at which time LCMS analysis indicated the presence of 16% of the starting material. Then, another 0.1 equivalents of all the above reagents were added and the reaction mixture was stirred for another 15 h. The solids were filtered off and were washed with ethyl acetate and then the filtrate was washed with saturated sodium chloride solution and dried over anhydrous magnesium sulfate. Filtration and concentration gave the crude residue which was purified using an ISCO (340 g) column chromatography to obtain [3-(4-nitro-phenoxy)propyl]-carbamic acid tert-butyl ester (64% yield) as a white solid. ES(+)-HRMS m/e calcd. for C14H20N2O5 (M+Na)+ 319.1264, obsd. 319.1266.

Step 5: Preparation of [3-(4-amino-phenoxy)-propyl]-carbamic acid tert-butyl ester

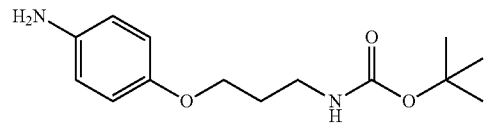 [SMILES: CC(C)(C)OC(=O)NCCCOc1ccc(N)cc1]

To a solution of [3-(4-nitro-phenoxy)-propyl]-carbamic acid tert-butyl ester (7.7 g, 26 mmol) in methanol (200 mL, heated to dissolve starting material) were added water (10 mL), ammonium chloride (20.9 g, 390 mmol, 15 equivalents), and zinc dust (16.4 g, 260 mmol, 10 equivalents, 3-portions) at room temperature. After addition of zinc dust, the reaction mixture was exothermic and the reaction mixture was stirred for 1-2 h at which time TLC analysis of the mixture indicated the absence of starting material. Then, the solids were filtered off and were washed with water and ethyl acetate and the organic compound from filtrate was extracted with ethyl acetate (3×100 mL). The combined extracts were washed with brine solution and dried over anhydrous magnesium sulfate. Filtration and concentration gave the crude residue which was purified using an ISCO (330 g) column chromatography to isolate [3-(4-aminophenoxy)propyl]-carbamic acid tert-butyl ester (79% yield) as a white solid. ES(+)-HRMS m/e calcd. for C14H22N2O3 (M+Na)+289.1522, obsd. 289.1523.

Step 6: Preparation of (S)—N-[4-(3-tert-butoxycar-
bonylamino-propoxy)-phenyl]-3-(9H-fluoren-9-yl-
methoxycarbonylamino)-succinamic acid tert-butyl
ester

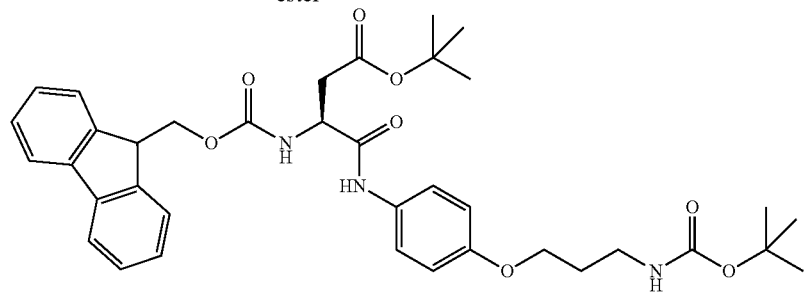

To a solution of [3-(4-amino-phenoxy)-propyl]-carbamic acid tert-butyl ester (5.41 g, 20.2 mmol) and (S)-2-(9H-fluoren-9-ylmethoxycarbonylamino)-succinic acid tert-butyl ester in DMF (40 mL) were added HOBT (3 g, 22.2 mmol), and DIPEA (8.52 g, 66.6 mmol) at room temperature. The resulting solution was cooled to 0° C. with an ice-bath and the solid HBTU (8.43 g, 22.2 mmol) was added in 3 portions during 5-10 minutes period. After addition, the cooling bath was removed and the reaction mixture was allowed to warm to room temperature and stirred for 2.5 h at which point LCMS analysis indicated the absence of starting material. Then, the reaction mixture was diluted with ethyl acetate (400 mL) and were washed with water (400 ml), saturated sodium bicarbonate solution (400 mL), and brine solution (400 mL). After drying over anhydrous magnesium sulfate, the filtration was concentrated and the crude residue was purified using an ISCO (330 g) column chromatography to isolate (S)—N-[4-(3-tert-butoxycarbonylamino-propoxy)-phenyl]-3-(9H-fluoren-9-ylmethoxycarbonylamino)-succinamic acid tert-butyl ester (95% yield) as a white solid. ES(+)-HRMS m/e calcd. for C37H45N3O8 (M+Na)+ 682.3099, obsd. 682.3105.

Step 7: Preparation of (S)-3-amino-N-[4-(3-tert-
butoxycarbonylamino-propoxy)phenyl]-succinamic
acid tert-butyl ester

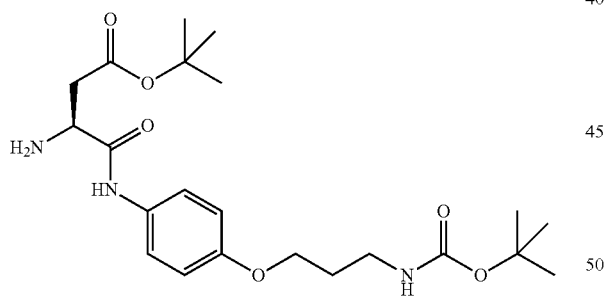

To a solution of (S)—N-[4-(3-tert-butoxycarbonylamino-propoxy)-phenyl]-3-(9H-fluoren-9-ylmethoxycarbonylamino)-succinamic acid tert-butyl ester (11 g, 16.67 mmol) in THF (95 mL) were added piperidine (4.26 g, 50 mmol) at room temperature. The resulting solution was stirred 4 h at which point LCMS analysis indicated the absence of starting material. Then, the solvent was removed under vacuum and the residue was azeotrophed with toluene to obtain a white solid which was dissolved in minimum ethyl acetate (25-30 mL) at hot condition and then it was diluted with hexanes (250-300 mL) until precipitation. The resulting solids were collected by filtration and washed with hexanes to obtain, after air drying, (S)-3-amino-N-[4-(3-tert-butoxycarbonylamino-propoxy)-phenyl]-succinamic acid tert-butyl ester (81% yield) as a white solid. ES(+)-HRMS m/e calcd. for C22H35N3O6 (M+Na)+460.2418, obsd. 460.2416.

Step 8: Preparation of (S)-3-(2-(3-(N,N-bis-tert-
butoxycarbonylguanidino)benzoylamino)-acety-
lamino)-N-[4-(3-tert-butoxycarbonylamino-
propoxy)-phenyl]-succinamic acid tert-butyl ester

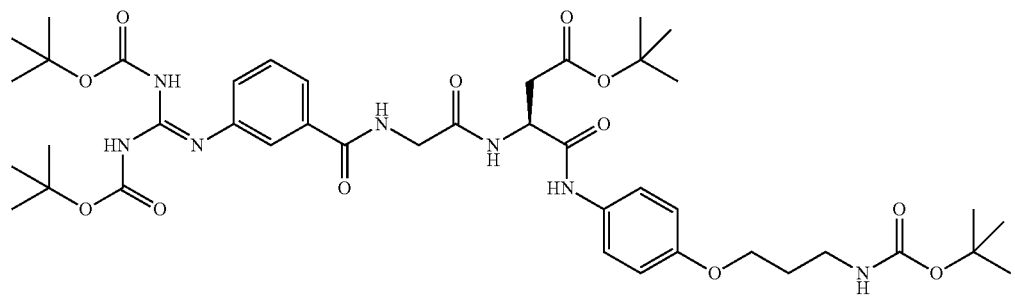 [SMILES: CC(C)(C)OC(=O)C[C@H](NC(=O)CNC(=O)c1cccc(N=C(NC(=O)OC(C)(C)C)NC(=O)OC(C)(C)C)c1)C(=O)Nc1ccc(OCCCNC(=O)OC(C)(C)C)cc1]

To a mixture of (S)-3-amino-N-[4-(3-tert-butoxycarbonylamino-propoxy)-phenyl]-succinamic acid tert-butyl ester (2.0 g, 4.58 mmol), 2-(3-(N,N-bis-tert-butoxycarbonyl-guanidino)benzoyl)-amino-acetic acid (2.0 g, 4.58 mmol), HBTU (1.91 g, 5.04 mmol), and HOBT (681 mg, 5.04 mmol) were added DMF (15 mL) followed by DIPEA (1.95 g, 15.12 mmol) at room temperature under nitrogen atmosphere. The resulting light brown solution was stirred for 2 days at which point lot of gel like solids were formed. Then, water (~50 mL) was added and the resulting light brown paste was dissolved in ethyl acetate (~200 mL) at hot condition. Then, the two layers were separated and the aqueous layer was extracted one more time with ethyl acetate (100 mL). The combined ethyl acetate extracts were washed with saturated sodium bicarbonate solution, water, and brine solution and then the organic layer was dried over anhydrous magnesium sulfate. Filtration and concentration gave the crude light brown solid which was purified using an ISCO (120 g) column chromatography to isolate (S)-3-(2-(3-(N,N-bis-tert-butoxycarbonylguanidino)-benzoylamino)-acetylamino)-N-[4-(3-tert-butoxycarbonylamino-propoxy)-phenyl]-succinamic acid tert-butyl ester (94% yield) as a white solid. ES(+)-HRMS m/e calcd. for C42H61N7O12 (M+H)+856.4450, obsd. 856.4451.

Step 9: Preparation of (S)—N-[4-(3-amino-propoxy)-phenyl]-3-(2-(3-(guanidino)benzoylamino)-acetylamino)-succinamic acid trifluoroacetate salt αVβ3 Ligand-1

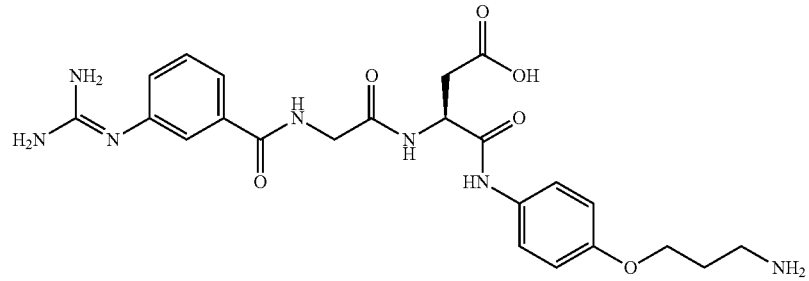 [SMILES: NCCCOc1ccc(NC(=O)[C@H](CC(=O)O)NC(=O)CNC(=O)c2cccc(N=C(N)N)c2)cc1]

To a solution of (S)-3-(2-(3-(N,N-bis-tert-butoxycarbonylguanidino)-benzoylamino)acetylamino)-N-[4-(3-tert-butoxycarbonylamino-propoxy)-phenyl]-succinamic acid tert-butyl ester (3.7 g, 4.32 mmol) in dichloromethane (80 mL) was added an excess of trifluoroacetic acid (40 mL) at 0° C. (ice-bath) under nitrogen atmosphere. The resulting colorless solution was stirred for 1-2 h at this temperature and then it was allowed to warm to room temperature by removing the cooling bath. After stirring for 15 h, the solvent was removed under vacuum and the residue was azeotrophed with toluene. The resulting dark blue paste was triturated with tert-butyl methyl ether, but it did not give good solids. Then, the solvent was removed under vacuum and the residue was triturated with dichloromethane and diethyl ether. The resulting light brown solids were collected by filtration and washed with diethyl ether. After drying in the air, 2.7 g of (S)—N-[4-(3-amino-propoxy)-phenyl]-3-(2-(3-(guanidino)-benzoylamino)-acetylamino)succinamic acid was isolated as a trifluoroacetate salt (85% yield). ES(+)-HRMS m/e calcd. for C23H29N7O6 (M+H)+500.2252, obsd. 500.2252.

Step 10: Preparation of (S)—N-[4-[3-[3-[2-[2-[2-[2-[2-[2-[2-[2-[3-(2,5-dioxo-2,5-dihydro-pyrrol-1-yl)-propionylamino]ethoxy]ethoxy]ethoxy]ethoxy]ethoxy]ethoxy]ethoxy]-propionylamino]propoxy]-phenyl]-3-[2-[3-(guanidino)-benzoylamino]-acetylamino]-succinamic acid; αVβ3 Ligand Reagent 1

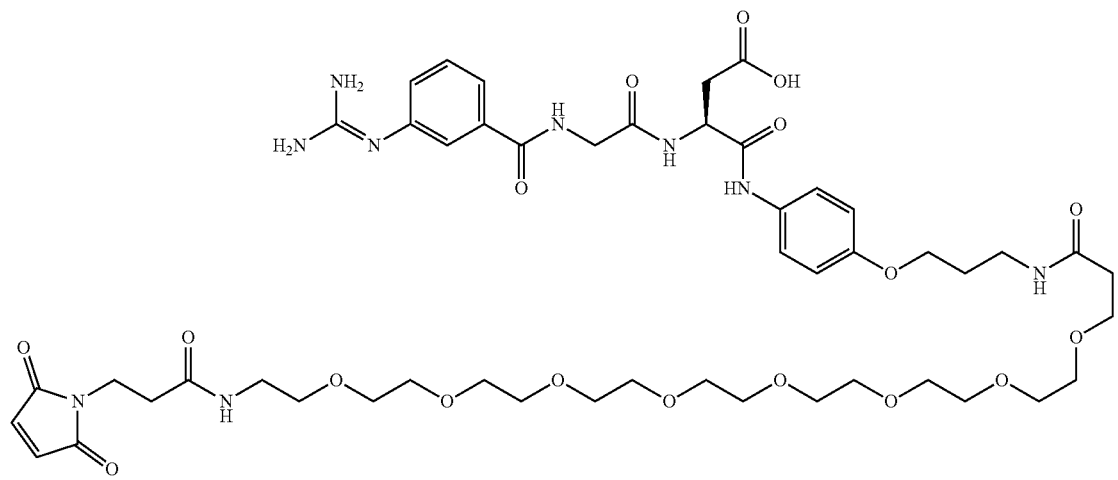 [SMILES: NC(N)=Nc1cccc(C(=O)NCC(=O)N[C@@H](CC(=O)O)C(=O)Nc2ccc(OCCCNC(=O)CCOCCOCCOCCOCCOCCOCCOCCOCCNC(=O)CCN3C(=O)C=CC3=O)cc2)c1]

To a solution of (S)—N-[4-(3-amino-propoxy)-phenyl]-3-(2-(3-(guanidino)-benzoylamino)acetylamino)-succinamic acid (245 mg, 0.289 mmol) and 3-[2-[2-[2-[2-[2-[2-[2-[[3-(2,5-dioxo-2,5-dihydro-pyrrol-1-yl)-propionylamino]-ethoxy]ethoxy]ethoxy]ethoxy]ethoxy]ethoxy]ethoxy]-propionic acid-2,5-dioxo-pyrrolidin-1-yl ester (200 mg, 0.289 mmol) in DMSO (5 mL) was added an excess of DIPEA (186 mg, 252 uL, 1.44 mmol) at room temperature under nitrogen atmosphere. The resulting light yellow solution was stirred for 2 h at which time LCMS analysis indicated the absence of starting material. Then, the excess DIPEA was removed under vacuum and the desired product was isolated by purification using HPLC to obtain 212 mg (68% yield) of (S)—N-[4-[3-[3-[2-[2-[2-[2-[2-[2-[2-[3-(2,5-dioxo-2,5-dihydro-pyrrol-1-yl)-propionylamino]ethoxy] ethoxy]ethoxy]ethoxy]ethoxy] ethoxy]ethoxy]-propionylamino]propoxy]-phenyl]-3-[2-[3-(guanidino)-benzoylamino]-acetylamino]-succinamic acid as a light yellow solid. ES(+)-HRMS m/e calcd. for C49H71N9O18 (M+H)+1074.4990, obsd. 1074.4984.

Example 2

Preparation of (S)—N-[4-[3-[3-[2-[2-[2-[2-[2-[2-[2-[2-[2-[2-[2-[3-(2,5-dioxo- 2,5-dihydro-pyrrol-1-yl)-propionylamino]ethoxy]ethoxy]ethoxy]ethoxy] ethoxy]ethoxy]ethoxy]ethoxy]ethoxy]ethoxy] ethoxy]ethoxy]-propionylamino]propoxy]-phenyl]-3-[2-[3-(guanidino)-benzoylamino]acetylamino]-succinamic acid; αVβ3 Ligand Reagent 2

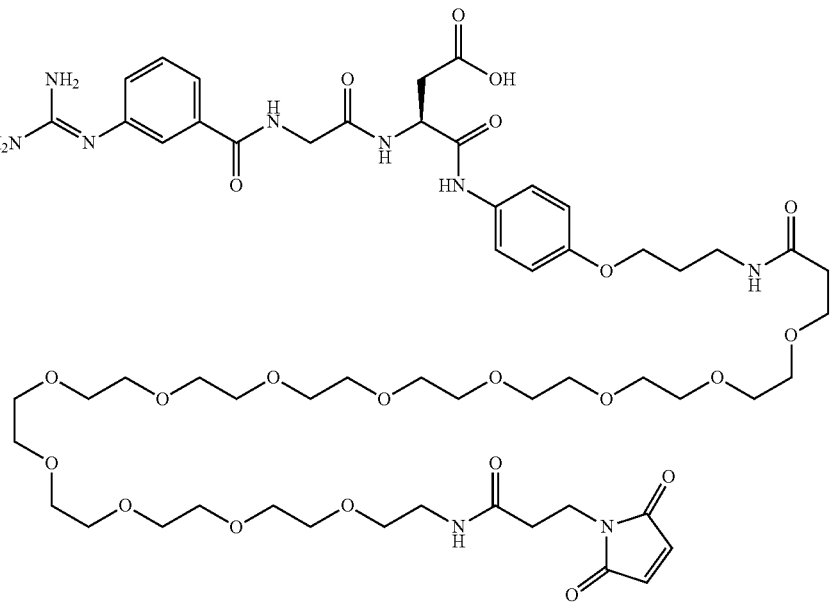

The title compound was prepared using a similar procedure as described in Example 1, Step 10, starting from (S)—N-[4-(3-amino-propoxy)-phenyl]-3-(2-(3-(guanidino)-benzoylamino)acetylamino)-succinamic acid (245 mg, 0.289 mmol), 3-[2-[2-[2-[2-[2-[2-[2-[2-[2-[2-[2-[3-(2,5-dioxo-2,5-dihydro-pyrrol-1-yl)-propionylamino]-ethoxy]ethoxy]ethoxy]ethoxy]ethoxy]ethoxy]ethoxy]ethoxy]ethoxy]-propionic acid-2,5-dioxo-pyrrolidin-1-yl ester (250 mg, 0.289 mmol), and DIPEA (373 mg, 503 uL, 2.89 mmol), and after HPLC purification, resulted in a light brown oil (312 mg, 86%). ES(+)-HRMS m/e calcd. for C57H87N9O22 (M+H)+1250.6039, obsd. 1250.6032.

Example 3

Preparation of (S)—N-[[[4-[3-[2-[2-[2-[2-[2-[2-[2-(2-acetylsulfanyl-ethoxy)ethoxy]ethoxy]ethoxy]ethoxy]ethoxy]ethoxy]-1-oxopropyl]amino]propoxy]-phenyl]-3-[2-[3-[guanidino]-benzoylamino]-acetylamino]-succinamic acid trifluoroacetate salt; αVβ3 Ligand Reagent 3

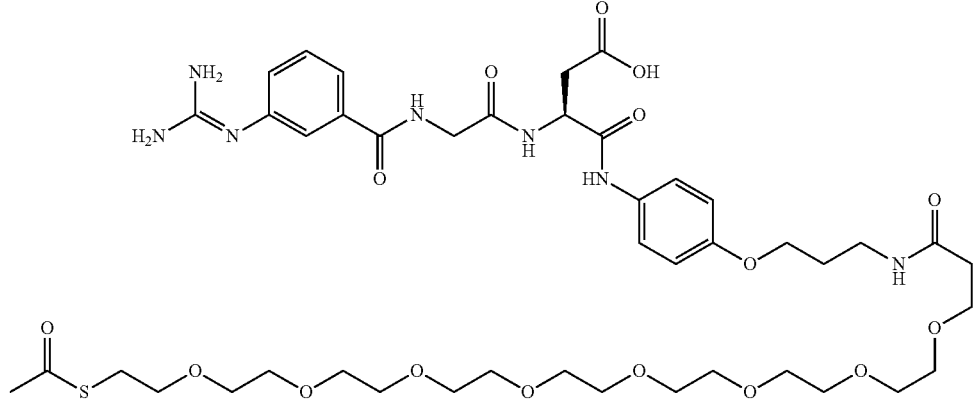 [SMILES: CC(=O)SCCOCCOCCOCCOCCOCCOCCOCCOCCC(=O)NCCCOc1ccc(NC(=O)[C@H](CC(=O)O)NC(=O)CNC(=O)c2cccc(N=C(N)N)c2)cc1]

The title compound was prepared using a similar procedure as described in Example 1, Step 10, starting from (S)—N-[4-(3-amino-propoxy)-phenyl]-3-(2-(3-(guanidino)-benzoylamino)acetylamino)-succinamic acid (245 mg, 0.289 mmol), 3-[2-[2-[2-[2-[2-[2-[2-(2-acetylsulfanyl-ethoxy)ethoxy]ethoxy]ethoxy]ethoxy]ethoxy]ethoxy]-propionic acid-2,5-dioxo-pyrrolidin-1-yl ester (172 mg, 0.289 mmol), and DIPEA (503 uL, 2.89 mmol), and after HPLC purification, resulted in a light yellow viscous oil (172 mg, 73%). ES(+)-HRMS m/e calcd. for C44H67N7O16S (M+H)+982.4438, obsd. 982.4432.

Example 4

(S)—N-[[[4-[3-[2-[2-[2-[2-[2-[2-(2-acetylsulfanyl-ethoxy)ethoxy]ethoxy]ethoxy]ethoxy]ethoxy]ethoxy]-1-oxopropyl]amino]propoxy]-phenyl]-3-[2-[3-(tetrahydropyrimidin-2-ylideneamino)-benzoylamino]-acetylamino]-succinamic acid; αVβ3 Ligand Reagent 4

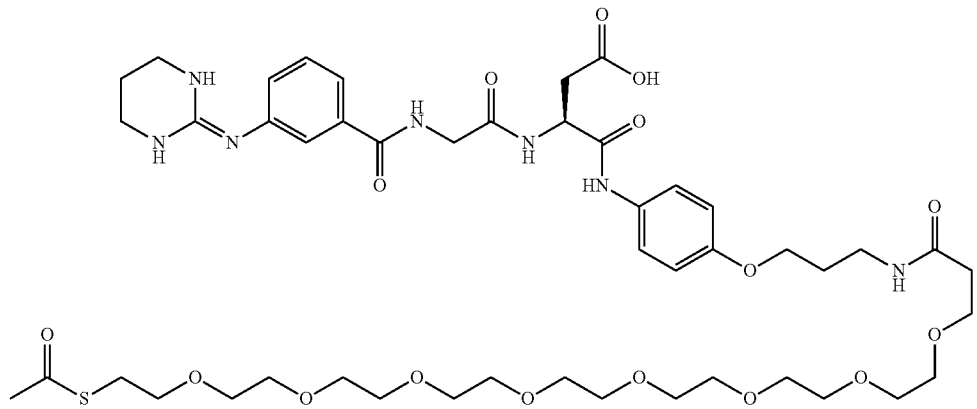 [SMILES: CC(=O)SCCOCCOCCOCCOCCOCCOCCOCCOCCC(=O)NCCCOc1ccc(NC(=O)[C@H](CC(=O)O)NC(=O)CNC(=O)c2cccc(N=C3NCCCN3)c2)cc1]

Step 1: Preparation of 2-[3-(benzyloxycarbonylmethylcarbamoyl)phenylimino]-dihydropyrimidine-1,3-dicarboxylic acid di tert-butyl ester

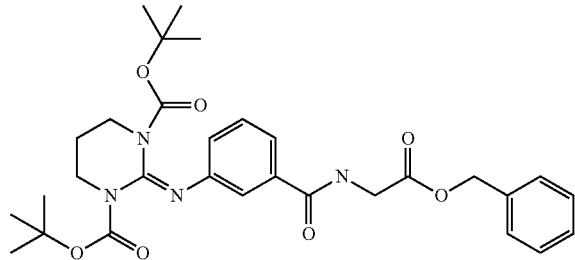 [SMILES: CC(C)(C)OC(=O)N1CCCN(C(=O)OC(C)(C)C)C1=Nc1cccc(C(=O)NCC(=O)OCc2ccccc2)c1]

The title compound was prepared using a similar procedure as described in Example 1, Step 2, starting from 2-[3-carboxyphenylimino]-dihydropyrimidine-1,3-dicarboxylic acid di tert-butyl ester (4.85 g, 11.56 mmol), 2-chloro-4,6-dimethoxy-triazine (2.03 g, 11.56 mmol), N-methylmorpholine (1.17 g, 1.27 mL, 11.56 mmol), glycine benzylester p-TsOH salt (3.9 g, 11.56 mmol), and a second equivalent of N-methylmorpholine (1.17 g, 1.27 mL, 11.56 mmol) in anhydrous tetrahydrofuran (90 mL), and after ISCO column chromatography purification, resulted in a colorless viscous oil (3.19 g, 49%). ES(+)-HRMS m/e calcd. for C30H38N4O7 (M+H)+567.2813, obsd. 567.2810.

Step 2: Preparation of 2-[3-(carboxymethyl-carbamoyl)phenylimino]-dihydropyrimidine-1,3-dicarboxylic acid di tert-butyl ester

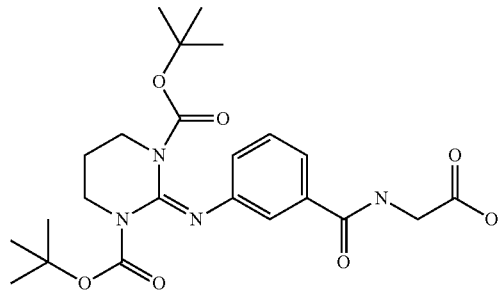 [SMILES: CC(C)(C)OC(=O)N1CCCN(C(=O)OC(C)(C)C)C1=Nc1cccc(C(=O)NCC(=O)O)c1]

The title compound was prepared using a similar procedure as described in Example 1, Step 3, starting from 2-[3-(benzyloxycarbonylmethylcarbamoyl)phenylimino]-dihydropyrimidine-1,3-dicarboxylic acid di tert-butyl ester (475 mg, 0.84 mmol) and 10% Pd/on carbon (250 mg) in absolute ethanol (20 mL), resulting in an amorphous white solid (355 mg, 89%). ES(+)-HRMS m/e calcd. for C23H32N4O7 (M+H)+477.2344, obsd. 477.2344.

Step 3: Preparation of 2-[3-[[[(S)-2-tert-butoxycarbonyl-1-[4-(3-tert-butoxycarbonylamino-propoxy)phenylcarbamoyl]ethylcarbamoyl]methyl]carbamoyl]phenylimino]dihydropyrimidine-1,3-dicarboxylic acid di tert-butyl ester

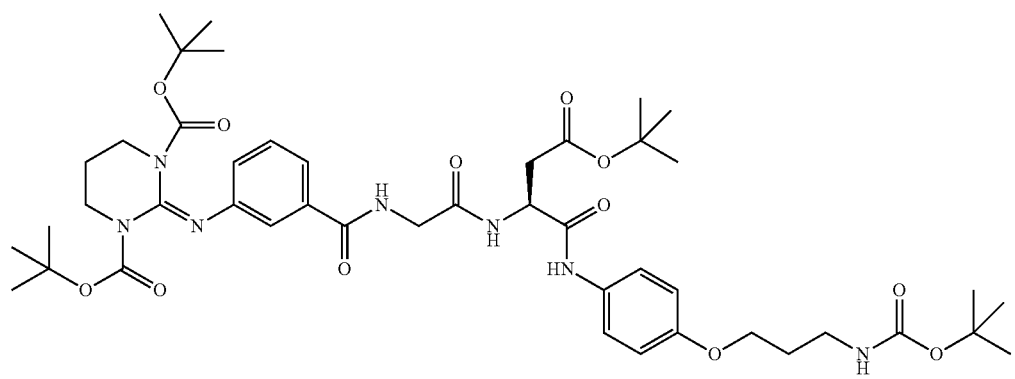 [SMILES: CC(C)(C)OC(=O)C[C@H](NC(=O)CNC(=O)c1cccc(N=C2N(C(=O)OC(C)(C)C)CCCN2C(=O)OC(C)(C)C)c1)C(=O)Nc1ccc(OCCCNC(=O)OC(C)(C)C)cc1]

The title compound was prepared using a similar procedure as described in Example 1, Step 8, starting from 2-[3-(carboxymethyl-carbamoyl)phenylimino]-dihydropyrimidine-1,3-dicarboxylic acid di tert-butyl ester (332 mg, 0.69 mmol), (S)-3-amino-N-[4-(3-tert-butoxycarbonylamino-propoxy)-phenyl]-succinamic acid tert-butyl ester (305 mg, 0.69 mmol), HBTU (290 mg, 0.76 mmol), HOBT (104 mg, 0.76 mmol), and DIPEA (297 mg, 400 uL, 2.3 mmol) in DMF (5 mL), and after ISCO column chromatography purification, resulted in an amorphous white solid (602 mg, 97%). ES(+)-HRMS m/e calcd. for C45H65N7O12 (M+H)+896.4764, obsd. 896.4764.

Step 4: Preparation of (S)—N-[4-(3-aminopropoxy)phenyl]-3-[2-[3-(tetrahydropyrimidin-2-ylideneamino)benzoylamino]acetylamino]succinamic acid; αVβ3 Ligand-2

The title compound was prepared using a similar procedure as described in Example 1, Step 9, starting from 2-[3-[[[(S)-2-tert-butoxycarbonyl-1-[4-(3-tert-butoxycarbonylamino-propoxy)phenylcarbamoyl]ethylcarbamoyl]methyl]carbamoyl]phenylimino]dihydropyrimidine-1,3-dicarboxylic acid di tert-butyl ester (595 mg, 0.66 mmol) and trifluoroacetic acid (10 mL) in dichloromethane (20 mL), resulting in a light brown solid as a trifluoroacetate salt (555 mg, 96%). ES(+)-HRMS m/e calcd. for C23H29N7O6 (M+H)+500.2252, obsd. 500.2252.

Step 5: Preparation of (S)—N-[[[4-[3-[2-[2-[2-[2-[2-[2-[2-(2-acetylsulfanyl-ethoxy)ethoxy]ethoxy]ethoxy]ethoxy]ethoxy]ethoxy]-1-oxopropyl]amino]propoxy]-phenyl]-3-[2-[3-(tetrahydropyrimidin-2-ylideneamino)-benzoylamino]-acetylamino]-succinamic acid (αVβ3 Ligand Reagent 4)

The title compound was prepared using a similar procedure as described in in Example 1, Step 10, starting from (S)—N-[4-(3-amino-propoxy)phenyl]-3-[2-[3-(tetrahydro-pyrimidin-2-ylideneamino)benzoylamino]acetylamino]-succinamic acid (265 mg, 0.3 mmol), 3-[2-[2-[2-[2-[2-[2-[2-(2-acetylsulfanyl-ethoxy)ethoxy]ethoxy]ethoxy]ethoxy]ethoxy]ethoxy]-propionic acid-2,5-dioxo-pyrrolidin-1-yl ester (179 mg, 0.3 mmol), and DIPEA (387 mg, 526 uL, 3.0 mmol), and after HPLC purification, resulted in a light yellow viscous oil (208 mg, 68%). ES(+)-HRMS m/e calcd. for C47H71N7O16S (M+H)+ 1022.4751, obsd. 1022.4742.

Example 5

Preparation of (S)—N-[[4-[3-[2-[2-[2-[2-[2-[2-[2-[2-[2-[2-[2-(2-acetylsulfanyl-ethoxy)ethoxy]ethoxy]ethoxy]ethoxy]ethoxy]ethoxy]ethoxy]ethoxy]ethoxy]ethoxy]propionylamino]methyl]phenyl]-3-[2-[[2-(3-benzylureido)thiazole-4-carbonyl]amino]acetylamino]-succinamic acid; αVβ3 Ligand Reagent 5

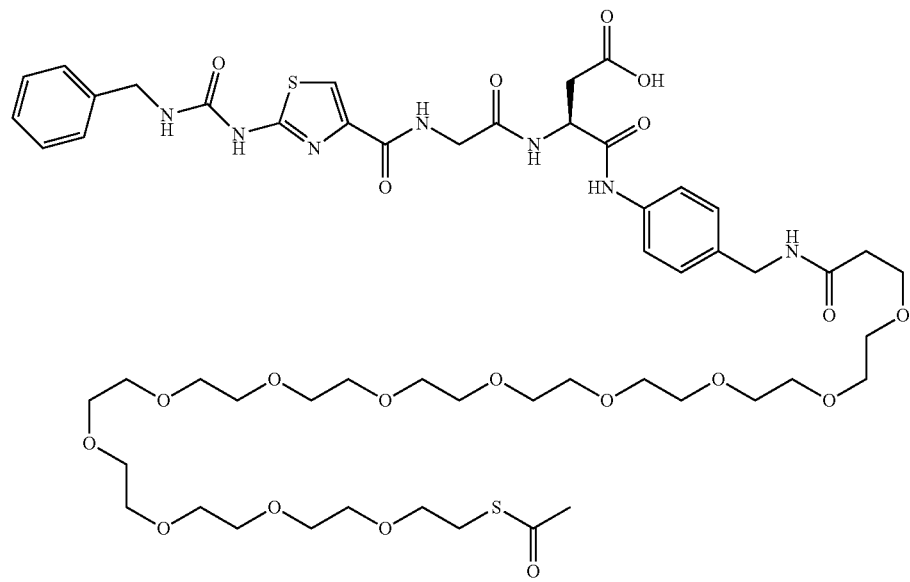 [SMILES: CC(=O)SCCOCCOCCOCCOCCOCCOCCOCCOCCOCCOCCOCCOCCC(=O)NCc1ccc(NC(=O)[C@H](CC(=O)O)NC(=O)CNC(=O)c2csc(NC(=O)NCc3ccccc3)n2)cc1]

The title compound was prepared using a similar procedure as described in Example 1, Step 10, starting from (S)—N-[4-aminomethylphenyl]-3-[2-[[2-(3-benzylureido)thiazole-4-carbonyl]amino]-acetylamino]-succinamic acid (166 mg, 0.3 mmol), 3-[2-[2-[2-[2-[2-[2-[2-[2-[2-[2-[2-(2-acetylsulfanyl-ethoxy)ethoxy]ethoxy]ethoxy]ethoxy]ethoxy]ethoxy]ethoxy]ethoxy]ethoxy]ethoxy]-propionic acid-2,5-dioxo-pyrrolidin-1-yl ester (232 mg, 0.3 mmol), and DIPEA (387 mg, 522 uL, 3.0 mmol), and after HPLC purification, resulted in a light brown oil (362 mg, 99%). ES(+)-HRMS m/e calcd. for C54H81N7O20S2 (M+H)+1212.5051, obsd. 1212.5058.

Example 6

(S)—N-[4-[3-[3-[2-[2-[2-[2-[2-[2-[2-[2-[3-(2,5-di-oxo-2,5-dihydro-pyrrol-1-yl)-propionylamino]ethoxy]ethoxy]ethoxy]ethoxy]ethoxy]ethoxy]ethoxy]propionylamino]propoxy]-phenyl]-3-[2-[[2-(3-benzyl-ureido)-thiazole-4-carbonyl]-amino]-acetylamino]-succinamic acid; αVβ3 Ligand Reagent 6

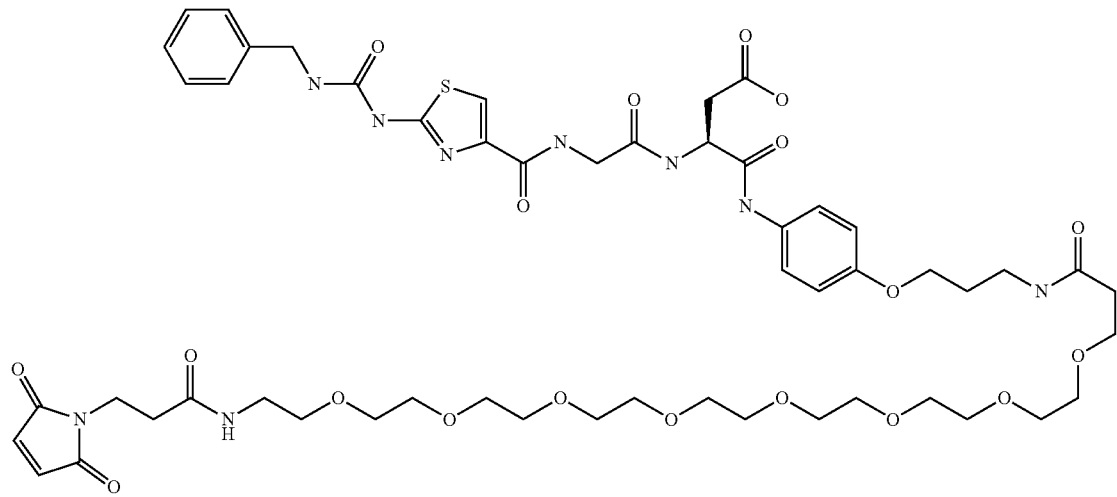 [SMILES: O=C(O)C[C@H](NC(=O)CNC(=O)c1csc(NC(=O)NCc2ccccc2)n1)C(=O)Nc1ccc(OCCCNC(=O)CCOCCOCCOCCOCCOCCOCCOCCOCCNC(=O)CCN2C(=O)C=CC2=O)cc1]

Step 1: Preparation of 2-amino-thiazole-4-carboxylic acid ethyl ester hydrobromide

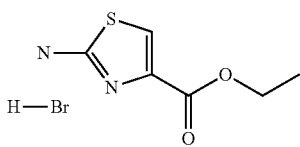

To a 3 L 3 neck flask fitted with a condenser, thermometer, and mechanical stirred, set in an oil bath, was charged with thiourea (48.2 g, 634 mmol) and ethyl bromopyruvate (137 g, 88.3 mL, 634 mmol). The reaction was heated slowly and carefully until a clear solution formed (60° C.) upon which the reaction became exothermic (temperature of reaction reached 110° C.) and was stirred as the reaction solidified. To the reaction was added EA (500 mL), the reaction was removed from heat and cooled to room temperature. The solid was filtered and washed with EA and Et2O resulting in 2-amino-thiazole-4-carboxylic acid ethyl ester hydrobromide salt resulting in a white solid (157 g, 98%).

Step 2: Preparation of 2-(3-benzyl-ureido)-thiazole-4-carboxylic acid ethyl ester

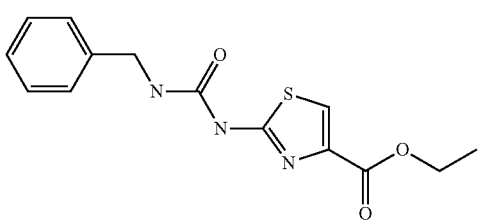 [SMILES: CCOC(=O)c1csc(NC(=O)NCc2ccccc2)n1]

To a reaction vessel containing 2-amino-thiazole-4-carboxylic acid ethyl ester hydrobromide salt (66.6 g, 263 mmol), 4-ethylmorpholine (60.7 g, 67.1 mL, 527 mmol), and anhydrous DMF (660 ml) was added benzyl isocyanate (42.1 g, 316 mmol), reaction stirred at room temperature under argon for 7 hr, more benzyl isocyanate (42.1 g, 316 mmol) was added, and reaction stirred at room temperature under argon overnight. The next day the reaction was concentrated 2/3, diluted with water (1.6 L), and the resulting precipitate was filtered and suction dried overnight yielding 2-(3-Benzyl-ureido)-thiazole-4-carboxylic acid ethyl ester as an off white solid (146 g, 182%). NMR analysis suggested material was still wet with water and DMF and was used as is.

Step 3: Preparation of 2-(3-benzyl-ureido)-thiazole-4-carboxylic acid

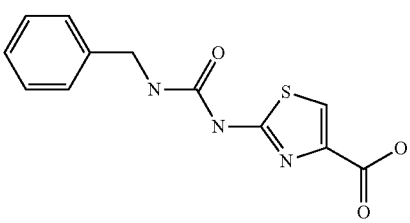 [SMILES: O=C(NCc1ccccc1)Nc1nc(C(=O)O)cs1]

To a reaction vessel containing wet 2-(3-benzyl-ureido)-thiazole-4-carboxylic acid ethyl ester (146 g, assumed theoretical 263 mmol) was added ethanol (1.2 L) and 1 N NaOH (1.31 L). The reaction was warmed (60° C.) and stirred under argon for 4 hr. The reaction was filtered and solid was discarded. The filtrate was cooled in an ice bath and acidified with 1 N HCl (1.31 L) and the resulting precipitate was filtered and washed with water and suction dried for two days yielding 2-(3-benzyl-ureido)-thiazole-4-carboxylic acid (72 g, 99%).

Step 4: Preparation of {[2-(3-benzyl-ureido)-thiazole-4-carbonyl]-amino}-acetic acid ethyl ester

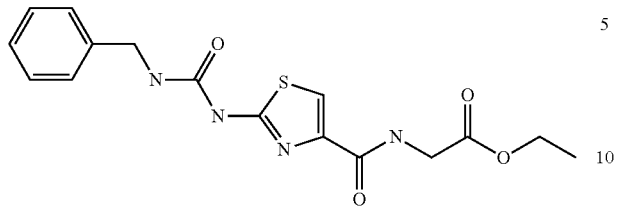

The title compound was prepared using a similar procedure as described in Example 1, Step 2, starting from 2-(3-benzyl-ureido)-thiazole-4-carboxylic acid (72 g, 259 mmol), 2-chloro-4,6-dimethoxy-triazine (45.5 g, 259 mmol), N-methylmorpholine (26.2 g, 28.5 ml, 259 mmol), glycine ethyl ester hydrochloride (36.2 g, 259 mmol), and a second equivalent of N-methylmorpholine (26.2 g, 259 mmol), and after crystallization and chromatography resulted in white crystals as a solid (72.6 g, 76%).

Step 5: Preparation of {[2-(3-Benzyl-ureido)-thiazole-4-carbonyl]-amino}-acetic acid The title compound was prepared using a similar procedure as described in Example 1, Step 3, starting from {[2-(3-benzyl-ureido)-thiazole-4-carbonyl]-amino}-acetic acid ethyl ester (72.3 g, 199 mmol), methanol (200 mL), THF (1 L), 1 N NaOH (0.2 L), and 1 N HCl (0.2 L), and after neutralization, evaporation, and crystallization, resulted in white crystals (73.1 g, 109%). NMR analysis suggested product contained solvent, used as is.

Step 6: Preparation of (S)-3-(2-{[2-(3-benzyl-ureido)-thiazole-4-carbonyl]-amino}-acetylamino)-N-[4-(3-tert-butoxycarbonylamino-propoxy)-phenyl]-succinamic acid tert-butyl ester

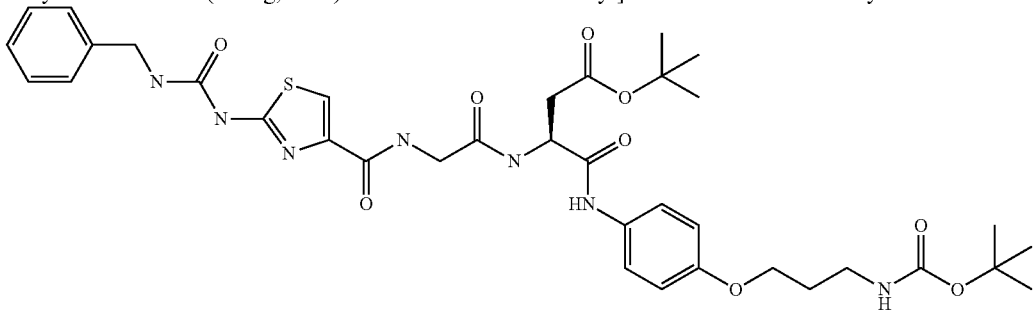

The title compound was prepared using a similar procedure as described in Example 1, Step 8, starting from {[2-(3-benzyl-ureido)-thiazole-4-carbonyl]-amino}-acetic acid, (S)-3-amino-N-[4-(3-tert-butoxycarbonylamino-propoxy)-phenyl]-succinamic acid tert-butyl ester (1.5 g, 3.43 mmol), HBTU (1.43 g, 3.77 mmol), HOBT (0.51 g, 3.77 mmol), and DIPEA (1.46 g, 1.97 mL, 11.3 mmol) resulting in a white solid (1.83 g, 70%). ES(+)-HRMS m/e calcd. for C36H47N7O9S (M+Na)+776.3048, obsd. 776.3050.

Step 7: Preparation of (S)—N-[4-(3-Amino-propoxy)-phenyl]-3-(2-{[2-(3-benzyl-ureido)-thiazole-4-carbonyl]-amino}-acetylamino)-succinamic acid αVβ3 Ligand Reagent 8, 40389-052) αVβ3 Ligand-3

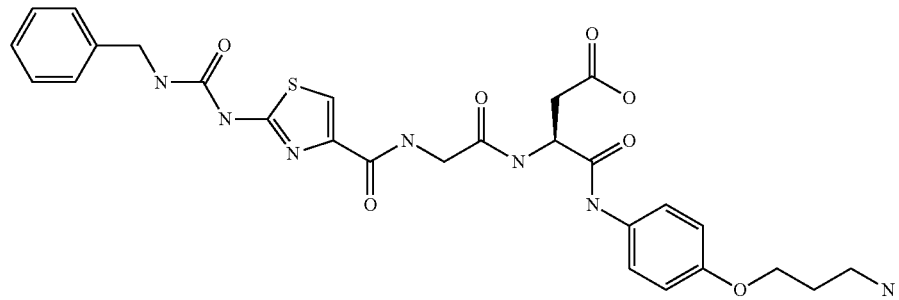 [SMILES: NCCCOc1ccc(NC(=O)[C@H](CC(=O)O)NC(=O)CNC(=O)c2csc(NC(=O)NCc3ccccc3)n2)cc1]

The title compound was prepared using a similar procedure as described in Example 1, Step 9, starting from (S)-3-(2-{[2-(3-benzyl-ureido)-thiazole-4-carbonyl]-amino}-acetylamino)-N-[4-(3-tert-butoxycarbonylamino-propoxy)-phenyl]-succinamic acid tert-butyl ester (1.83 g, 2.48 mmol) resulting in a white solid (1.29 g, 88%). ES(+)-HRMS m/e calcd. for C17H31N7O7S (M+H)+598.2079, obsd 598.2077.

Step 8: Preparation of (S)—N-[4-[3-[3-[2-[2-[2-[2-[2-[2-[2-[2-[3-(2,5-dioxo-2,5-dihydro-pyrrol-1-yl)-propionylamino]ethoxy]ethoxy]ethoxy]ethoxy]ethoxy]ethoxy]ethoxy]ethoxy]propionylamino]propoxy]-phenyl]-3-[2-[[2-(3-benzyl-ureido)-thiazole-4-carbonyl]-amino]-acetylamino]-succinamic acid

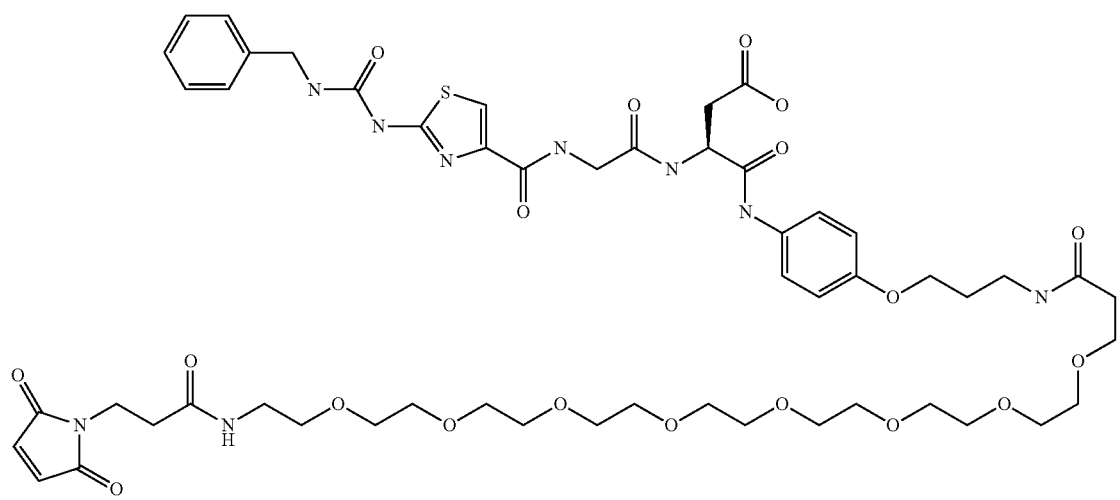 [SMILES: O=C(O)C[C@H](NC(=O)CNC(=O)c1csc(NC(=O)NCc2ccccc2)n1)C(=O)Nc1ccc(OCCCNC(=O)CCOCCOCCOCCOCCOCCOCCOCCOCCNC(=O)CCN2C(=O)C=CC2=O)cc1]

The title compound was prepared using a similar procedure as described in Example 1, Step 10, starting from (S)—N-[4-(3-Amino-propoxy)-phenyl]-3-(2-{[2-(3-benzyl-ureido)-thiazole-4-carbonyl]-amino}-acetylamino)-succinamic acid αVβ3 Ligand Reagent 8, 40389-052) (242 mg, 0.405 mmol), 3-[2-[2-[2-[2-[2-[2-[2-[2-[2-[2-[3-(2,5-di-oxo-2,5-dihydro-pyrrol-1-yl)- propionylamino]-ethoxy]ethoxy]ethoxy]ethoxy]ethoxy]ethoxy]ethoxy]-propionic acid-2,5-dioxo-pyrrolidin-1-yl ester (280 mg, 0.405 mmol), and DIPEA (262.2 mg, 353 µL, 2.03 mmol) and after HPLC purification, resulted in a light brown gum (206 mg, 43%) ES(+)-HRMS m/e calcd. for C53H73N9O19S (M+H)+1172.4816, obsd 1172.4806.

Example 7

Preparation of (S)—N-[4-[3-[3-[2-[2-[2-[2-[2-[2-[2-[2-[2-[2-[2-[3-(2,5-dioxo- 2,5-dihydro-pyrrol-1-yl)-propionylamino]ethoxy]ethoxy]ethoxy]ethoxy]ethoxy]ethoxy]ethoxy]ethoxy]ethoxy]ethoxy]ethoxy]propionylamino]ethoxy]-phenyl]-3-[2-[[2-(3-benzyl-ureido)thiazole-4-carbonyl]-amino]-acetylamino]-succinamic acid; αVβ3 Ligand Reagent 7, 40389-058)

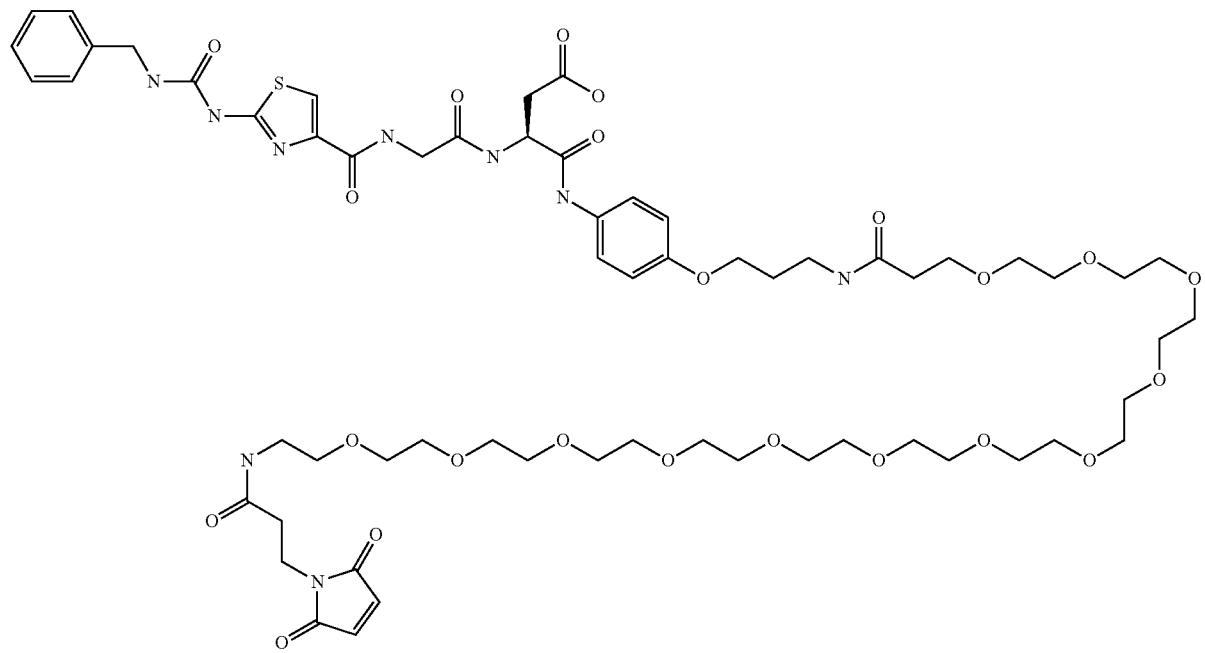 [SMILES: O=C(O)C[C@H](NC(=O)CNC(=O)c1csc(NC(=O)NCc2ccccc2)n1)C(=O)Nc1ccc(OCCCNC(=O)CCOCCOCCOCCOCCOCCOCCOCCOCCOCCOCCOCCOCCNC(=O)CCN2C(=O)C=CC2=O)cc1]

The title compound was prepared using a similar procedure as described in Example 1, Step 10, starting from (S)—N-[4-(3-Amino-propoxy)-phenyl]-3-(2-{[2-(3-benzyl-ureido)-thiazole-4-carbonyl]-amino}-acetylamino)-succinamic acid αVβ3 Ligand Reagent 8, 40389-052) (155 mg, 0.260 mmol), 3-[2-[2-[2-[2-[2-[2-[2-[2-[2-[2-[2-[3-(2,5-dioxo-2,5-dihydro-pyrrol-1-yl)- propionylamino]-ethoxy]ethoxy]ethoxy]ethoxy]ethoxy]ethoxy]ethoxy]ethoxy]ethoxy]ethoxy]-propionic acid-2,5-dioxo-pyrrolidin-1-yl ester (225 mg, 0.260 mmol), and DIPEA (167 mg, 226 μL, 1.29 mmol) and after HPLC purification, resulted in a light yellow gum (149 mg, 42%) ES(+)-HRMS m/e calcd. for C61H89N9O23S (M+H)+1348.5865, obsd 1348.5864.

Example 8

Preparation of (S)—N-[4-[3-[3-[2-[2-[2-[2-[2-[2-[2-[2-acetylsulfanyl-ethoxy]ethoxy]ethoxy]ethoxy]ethoxy]ethoxy]ethoxy]propionylamino]propoxy]-phenyl]-3-[2-[[2-(3-benzyl-ureido)-thiazole-4-carbonyl]-amino]-acetylamino]-succinamic acid; αVβ3 Ligand Reagent 8

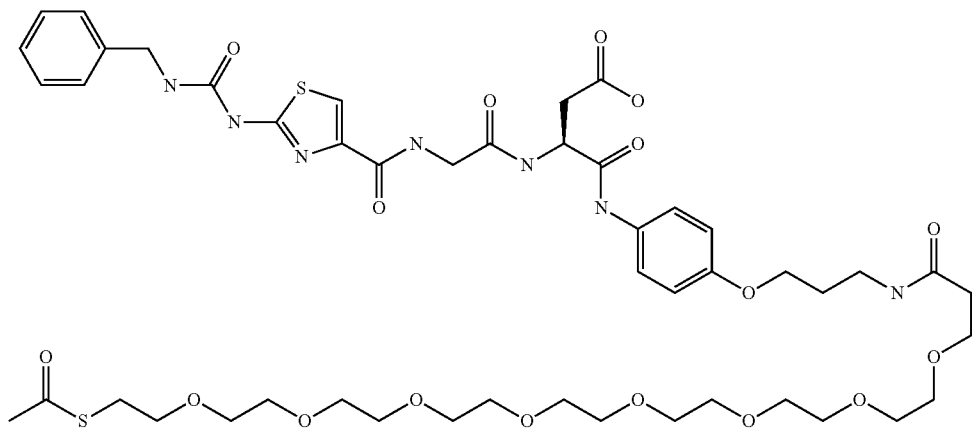 [SMILES: CC(=O)SCCOCCOCCOCCOCCOCCOCCOCCOCCC(=O)NCCCOc1ccc(NC(=O)[C@H](CC(=O)O)NC(=O)CNC(=O)c2csc(NC(=O)NCc3ccccc3)n2)cc1]

The title compound was prepared using a similar procedure as described in Example 1, Step 10, starting from (S)—N-[4-(3-Amino-propoxy)-phenyl]-3-(2-{[2-(3-benzyl-ureido)-thiazole-4-carbonyl]-amino}-succinamic acid, 40389-052) (120 mg, 0.201 mmol), 3-[2-[2-[2-[2-[2-[2-[2-acetylsulfanyl-ethoxy]-ethoxy]ethoxy]ethoxy]ethoxy]ethoxy]ethoxy]-propionic acid-2,5-dioxo-pyrrolidin-1-yl ester (120 mg, 0.201 mmol), and DIPEA (129.2 mg, 174 μL, 1.01 mmol) and after HPLC purification, resulted in a light brown gum (206 mg, 43%) ES(+)-HRMS m/e calcd. for C48H69N7O17S2 (M+H)+ 1080.4264, obsd 1080.4257.

Preparation of N-(2-methoxybenzyl)acetamide

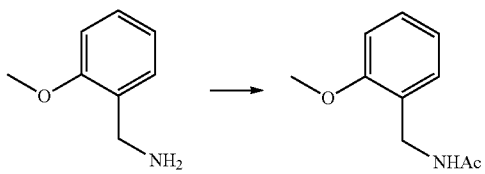

To a neat compound 2-methoxybenzylamine (40 g, 0.29 mol) was added dropwise Ac2O (80 mL, 0.85 mol) on an iced-water bath. Then the reaction mixture was stirred at room temperature for another 2 hours. The mixture was poured into 50 mL of water, and extracted with ethyl acetate (3×300 mL). The combined organic layers were washed with water (3×150 mL), brine (100 mL), and dried over anhydrous sodium sulfate. After filtration and concentration, the residue was suspended in petroleum ether (200 mL) and stirred for 10 minutes, then filtered and dried to give the title compound (36.5 g, 69.9%) as a pure white solid. 1H NMR (300 MHz, CDCl3): δ 7.31-7.25 (m, 2H), 6.95-6.87 (m, 2H), 6.01 (brs, 1H), 4.44 (d, 2H, J=6.0 Hz), 3.87 (s, 3H), 1.98 (s, 3H).

Preparation of N-(2-hydroxybenzyl)acetamide

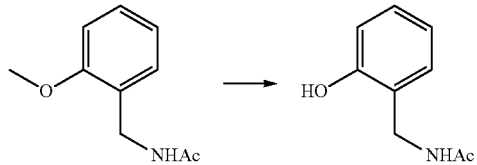

N-(2-methoxybenzyl)acetamide (6.5 g, 0.036 mol) was dissolved in DCM (100 mL), and the solution was cooled to −10° C. under nitrogen. To this solution was added BBr3 (15 mL, 0.15 mol) dropwise. After addition, the ice bath was removed and the reaction mixture was stirred at room temperature for 2 hours. The reaction mixture was re-cooled to −10° C. and quenched by water (20 mL). The mixture was extracted by DCM (3×100 mL), and the organic layer was washed with water (3×100 mL), brine (100 mL) and dried to give the title compound (4.3 g, 71.7%) as a solid. It was used directly in the next step without further purification. 1H NMR (300 MHz, DMSO): δ 9.56 (brs, 1H), 8.27 (brs, 1H), 7.09-7.03 (m, 2H), 6.79-6.72 (m, 2H), 4.16 (d, 2H, J=6.0 Hz), 1.87 (s, 3H). LC-MS: 166.2 [M+H]+, tR=1.15 min.

Preparation of tert-butyl 3-bromopropylcarbamate

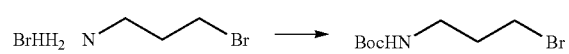

To a suspension of 3-bromopropylamine hydrobromide (50 g, 0.228 mol) in DCM (1000 mL) were added (Boc)2O (52 g, 0.238 mol) and triethylamine (100 mL, 0.722 mol). Then the reaction was stirred at room temperature for another 3 hours. The solvent was removed in vacuo and the residue was washed with petroleum ether (500 mL). The mixture was filtered and the filtrate was evaporated to give the title compound (54 g, 99.2%) as a colorless oil. 1H NMR (300 MHz, CDCl3): δ 4.69 (brs, 1H), 3.43 (t, 2H, J=6.6 Hz), 3.27-3.23 (m, 2H), 2.10-2.03 (m, 2H), 1.27 (s, 9H).

Preparation of {3-[2-(Acetylamino-methyl)-phenoxy]-propyl}-carbamic acid tert-butyl ester

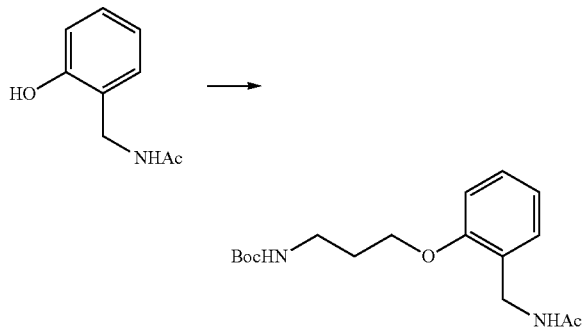

To a stirred solution of N-(2-hydroxybenzyl)acetamide (18.8 g, 0.11 mol) in DMF (100 mL) was added tert-butyl 3-bromopropylcarbamate (32 g, 0.135 mol) and K2CO3 (47 g, 0.34 mol) at room temperature. Then the reaction mixture was stirred at room temperature for 16 hours. The mixture was filtered and the solvent was removed in vacuo to give a crude product which was purified by silica gel chromatography (petroleum ether/ethyl acetate=1:3-1:4) to give the title compound (23 g, 62.8%) as a solid. 1H NMR (300 MHz, CDCl3): δ 8.08 (t, 1H, J=5.8 Hz), 7.20-7.13 (m, 2H), 6.94-6.86 (m, 3H), 4.21 (d, 2H, J=5.4 Hz), 3.97 (t, 2H, J=5.9 Hz), 3.14-3.08 (m, 2H), 1.87 (s, 3H), 1.82-1.86 (m, 2H), 1.36 (s, 9H). LC-MS: 323.1 [M+H]+, tR=2.98 min.

Preparation of tert-butyl 3-(2-(aminomethyl)phenoxy)propylcarbamate

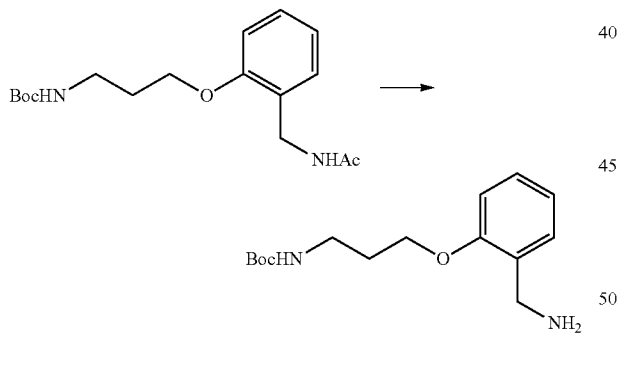

{3-[2-(Acetylamino-methyl)-phenoxy]-propyl}-carbamic acid tert-butyl ester (10.4 g, 0.032 mol) was suspended in hydrazine hydrate (150 mL, 85%) and the reaction mixture was stirred at reflux for 20 hours. The mixture was cooled to room temperature and extracted with diethyl ether (3×150 mL). The combined organic phase was washed with brine (150 mL) and dried over anhydrous sodium sulfate. After filtration and concentration, the residue was purified by silica gel chromatography (DCM/MeOH=20:1~1:1) to give the title compound (4 g, 44.6%). 1H NMR (300 MHz, CDCl3): δ 7.33-7.28 (m, 2H), 7.01-6.90 (m, 2H), 5.41-5.36 (m, 1H), 4.15-4.11 (m, 2H), 3.91 (s, 2H), 3.44-3.40 (m, 2H), 2.09-2.05 (m, 2H), 1.90 (brs, 2H), 1.50 (s, 9H). LC-MS: 281.1 [M+H]+, tR=2.33 min.

Synthesis of compound 2-aminothiazole-4-carboxylic acid 120

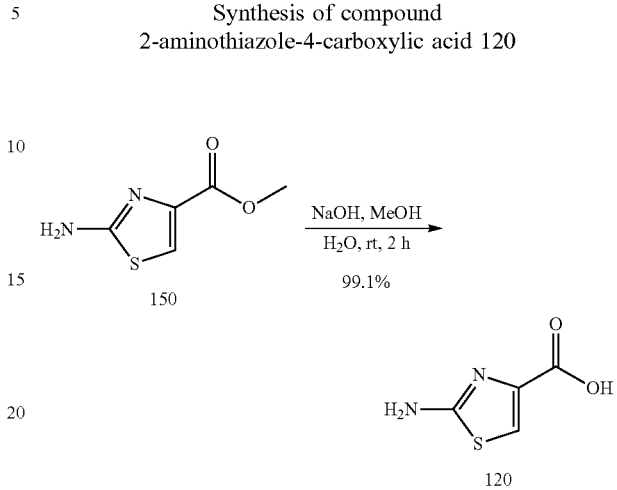

To a suspension of compound 150 (125 g, 0.525 mol) in THF (2500 mL) was added drop wise NaOH solution (63 g in 790 mL water) over one hour period. The resulting mixture was stirred at room temperature for 2 hours. The solvent was evaporated and the residue was treated with 2 N HCl (770 mL), filtered and dried to give compound 120 (75 g, 99.1%) as a yellow solid. 1H NMR (300 MHz, DMSO): δ 7.38 (s, 1H), 7.13 (brs, 2H).

Synthesis of compound [(2-amino-thiazole-4-carbonyl)-amino]-acetic acid methyl ester 8

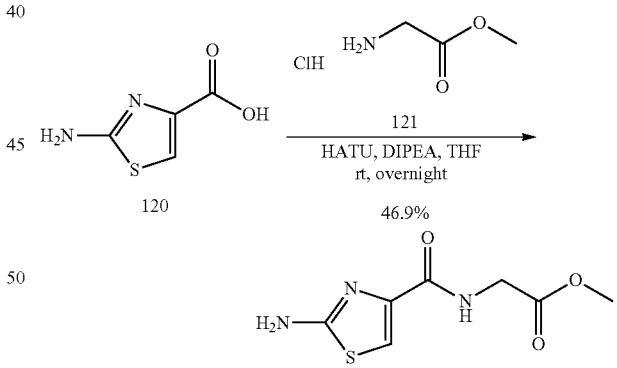

To a solution of compound 120 (1 g, 6.93 mmol) in DMF (50 mL) was added compound 121 (0.97 g, 7.73 mmol), DIPEA (3.5 mL, 21.1 mmol) and HATU (2.93 g, 7.7 mmol). The resulting solution was stirred at room temperature overnight. The reaction solution was evaporated in vacuo at 85° C. to dryness which was treated with 30 mL of THF, and stirred at room temperature for about 0.5 hour, then filtered, washed with a little of ethanol and dried to give compound 122 (0.7 g, 46.9%) as a yellow solid. 1H NMR (300 MHz, DMSO): δ 8.07 (t, 1H, J=6.0 Hz), 7.22 (s, 1H), 7.12 (brs, 1H), 3.97 (d, 2H, J=6.0 Hz), 3.64 (s, 3H).

Preparation of [(2-{3-[2-(3-tert-butoxycarbonylamino-propoxy)-benzyl]-ureido}-thiazole-4-carbonyl)-amino]-acetic acid methyl ester

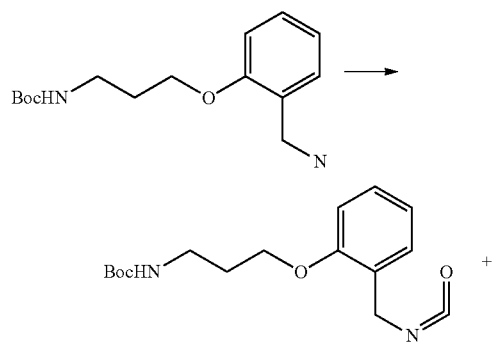

To a stirred solution of tert-butyl 3-(2-(aminomethyl)phenoxy)propylcarbamate (489 mg, 1.74 mmol) in DCM (50 mL) was added a solution of DIPEA (449 mg, 3.48 mmol) in DCM (5.0 mL). This solution was added dropwise to another solution of triphosgene (180 mg, 0.61 mmol) in DCM (5 mL) at 0° C. under nitrogen. After the addition, the mixture was stirred at 0° C. for another 15 minutes. The solution was evaporated to give [3-(2-isocyanatomethyl-phenoxy)propyl]-carbamic acid tert-butyl ester as a white solid. It was dissolved in 2.5 mL of DMF and used directly to the next step.

To a solution of [(2-amino-thiazole-4-carbonyl)-amino]-acetic acid methyl ester (374 mg, 1.74 mmol) and DIPEA (449 mg, 3.48 mmol) in DMF (2.5 mL) was added a solution of [3-(2-isocyanatomethyl-phenoxy)-propyl]-carbamic acid tert-butyl ester in DMF (2.5 mL made above) at room temperature. The reaction mixture was stirred at 80° C. for 2 hours. Then the mixture was cooled down and poured into 50 mL of water, extracted with ethyl acetate (3×100 mL). The organic phase was washed with brine (20 mL) and dried over anhydrous sodium sulfate. After filtration and concentration, the residue was purified by chromatography (petroleum ether/ethyl acetate=1:2-1:1) to give the title compound (165 mg, 18.2% over two steps) as a yellow solid.

1H NMR (300 MHz, CD3OD): δ 7.55 (s, 1H), 7.17-7.14 (m, 2H), 6.87-6.77 (m, 2H), 4.34 (s, 2H), 4.01-3.96 (m, 4H), 3.64 (s, 3H), 3.22-3.19 (m, 2H), 1.91-1.86 (m, 2H), 1.31 (s, 9H). LC-MS: 522.2 [M+H]+, tR=2.73 min.

Preparation of [(2-{3-[2-(3-tert-butoxycarbonylamino-propoxy)-benzyl]-ureido}-thiazole-4-carbonyl)-amino]-acetic acid To a solution of [(2-{3-[2-(3-tert-butoxycarbonylamino-propoxy)-benzyl]-ureido}-thiazole-4-carbonyl)-amino]-acetic acid methyl ester (0.165 g, 0.31 mmol) in THF (5 mL) was added dropwise a solution of LiOH.H2O (0.132 g, 3.1 mmol) in water (1 mL) at room temperature. Then the solution was stirred at this temperature for 16 hours. The solvent was evaporated and the residue was diluted with 5 mL of water. The water solution was extracted with ethyl acetate (10 mL), and the water phase was acidified by 1N citric acid solution until pH ~5. The water solution was extracted with ethyl acetate (3×15 mL), and the combined organic layers were washed with brine (10 mL), and dried over Na2SO4. After filtration and concentration, the title compound (0.080 g, 50.9%) was obtained as a solid.

1H NMR (300 MHz, DMSO): δ 10.57 (brs, 1H), 8.06 (t, 1H, J=5.8 Hz), 7.63 (s, 1H), 7.26-7.20 (m, 2H), 6.98-6.88 (m, 4H), 4.32 (d, 2H, J=5.7 Hz), 4.03-3.91 (m, 4H), 3.16-3.10 (m, 2H), 1.90-1.83 (m, 2H), 1.36 (s, 9H). LC-MS: 508.2 [M+H]+, tR=2.58 min Preparation of methyl 3-(2-(2-(3-(2-(3-(tert-butoxy-carbonylamino)propoxy)benzyl)ureido)thiazole-4-carboxamido)acetamido)-3-phenylpropanoate

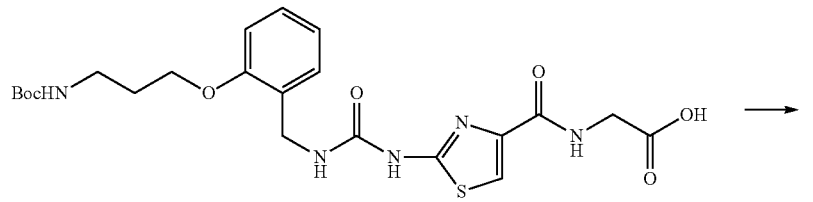

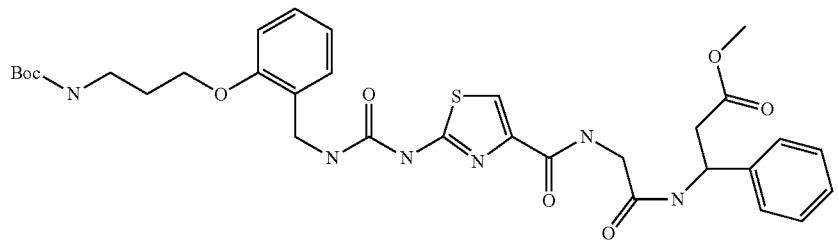

To a solution of [(2-{3-[2-(3-tert-butoxycarbonylamino-propoxy)-benzyl]-ureido}-thiazole-4-carbonyl)-amino]-acetic acid (0.7 g, 1.38 mmol) in THF (25 mL) was added DIPEA (1.4 g, 10.8 mmol) and HATU (0.525 g, 1.38 mmol) at room temperature. Then the reaction was stirred for 20 minutes. Methyl 3-amino-3-phenylpropanoate hydrochloride (0.29 g, 1.34 mmol) was added in one portion, and the reaction mixture was stirred for 16 hours. The solvent was removed at reduced pressure and the residue was dissolved in 50 mL of ethyl acetate, washed with 1N NaOH solution (3×15 mL), followed by 1N HCl (3×15 mL) and water (3×15 mL), then brine (15 mL) and dried over sodium sulfate. After filtration and concentration, the residue was purified by silica gel chromatography (eluting with ethyl acetate/petroleum ether/methanol=25:25:2) to give the title compound (0.54 g, 58.6%) as a solid.

1H NMR (300 MHz, CD3OD): δ 7.67 (s, 1H), 7.37-7.24 (m, 7H), 6.99-6.92 (m, 2H), 5.40 (t, 1H, J=7.3 Hz), 4.46 (s, 2H), 4.13-4.04 (m, 4H), 3.67 (s, 3H), 3.34-3.32 (m, 2H), 2.90-2.86 (m, 2H), 2.03-1.98 (m, 2H), 1.43 (s, 9H). LC-MS: 669.2 [M+H]+, tR=3.11 min Preparation of methyl 3-(2-(2-(3-(2-(3-amino-propoxyl)benzyl)ureido)thiazole-4-carboxamido)acetamido)-3-phenylpropanoate hydrochloride

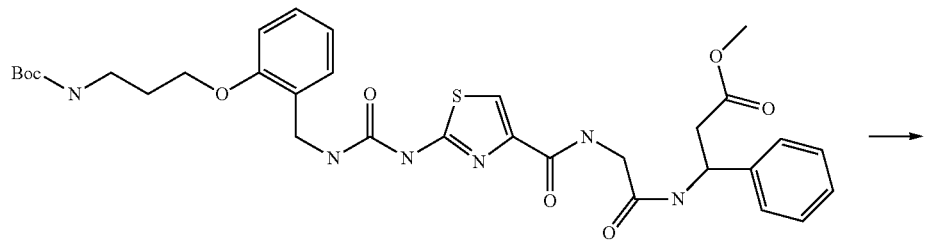

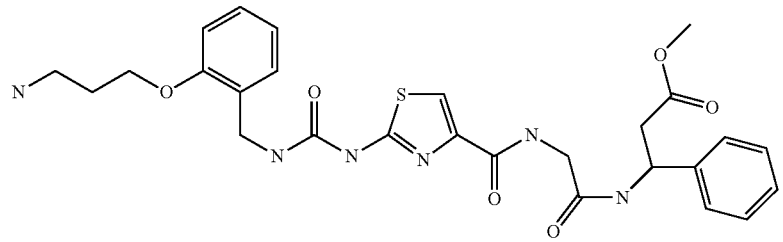

To a stirred saturated solution of HCl in ethyl acetate (250 mL) was added dropwise a solution of methyl 3-(2-(2-(3-(2-(3-(tert-butoxycarbonylamino)propoxy)benzyl)ureido)thiazole-4-carboxamido)acetamido)-3-phenylpropanoate (5.5 g, 8.23 mmol) in ethyl acetate (30 mL) at room temperature, then the mixture was stirred at room temperature for 16 hours. The organic solvent was removed under reduced pressure, and the solid was treated with diethyl ether (50 mL), and then filtered to give the title compound (4.7 g, 94.5%) as a white solid.

1H NMR (300 MHz, CD3OD): δ 7.69 (s, 1H), 7.36-7.27 (m, 7H), 7.02-6.95 (m, 2H), 5.40 (t, 1H, J=7.4 Hz), 4.48 (s, 2H), 4.19 (t, 2H, J=5.6 Hz), 4.06 (d, 2H, J=2.1 Hz), 3.63 (s, 3H) 3.24 (t, 2H, J=7.2 Hz), 2.90-2.86 (m, 2H), 2.24-2.15 (m, 2H). LC-MS: 569 [M+H]+, tR=3.00 min. HPLC: 99.85% at 214 nm, 99.14% at 254 nm, tR=4.05 min Preparation of 3-{2-[(2-{3-[2-(3-amino-propoxy)-benzyl]-ureido}-thiazole-4-carbonyl)-amino]-acetylamino}-3-phenyl-propionic acid αVβ3 Ligand-4

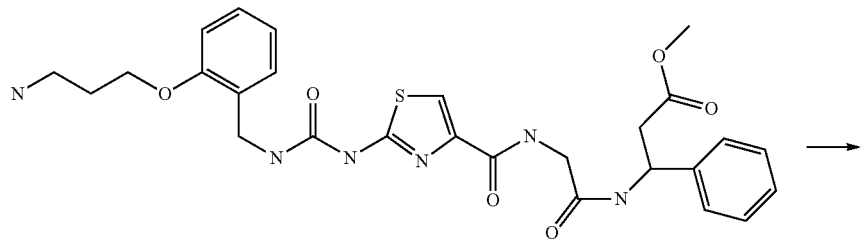

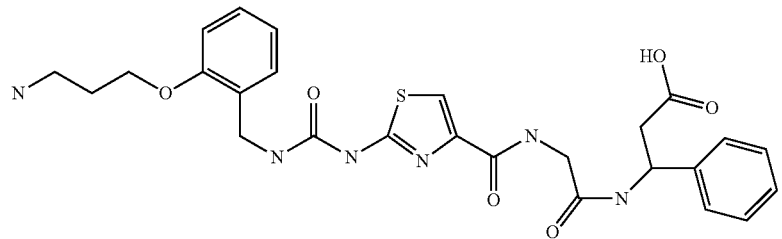

To a solution of 3-{2-[(2-{3-[2-(3-amino-propoxy)-benzyl]-ureido}-thiazole-4-carbonyl)amino]-acetylamino}-3-phenyl-propionic acid methyl ester hydrochloride (2.0 g, 3.31 mmol, Eq: 1.00) in methanol (10 ml) was added 2 M sodium hydroxide (33.1 mmol, Eq: 10.00). The reaction mixture was stirred to 55° C. overnight. During neutralization with 1 N HCl the crude product precipitated and was collected by filtration (2.19 g). The crude product was purified by reverse-phase HPLC to yield 1041 mg of the title compound as TFA salt.

HRMS m/e 555.2006 (M+H)+

Preparation of (R)-ethyl 3-(2-(2-(3-(2-(3-(tert-butoxycarbonylamino)propoxy)benzyl) ureido)thiazole-4-carboxamido)acetamido)-3-(pyridin-3-yl)propanoate

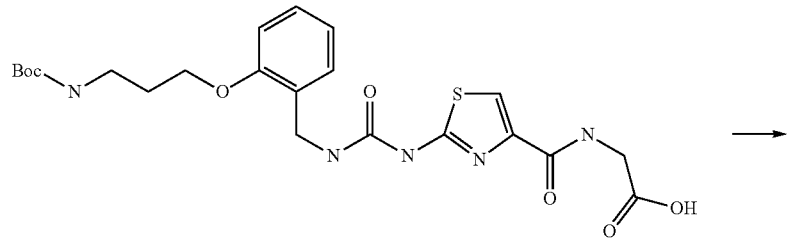

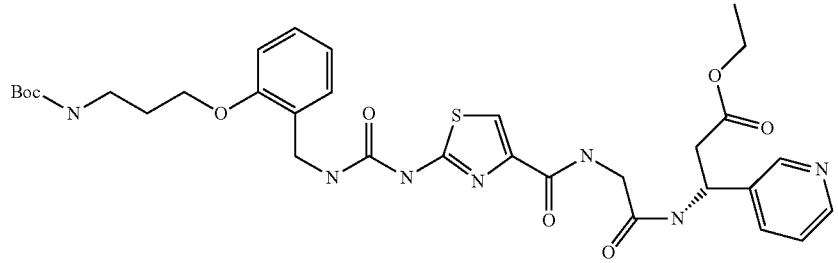

To a solution of [(2-{3-[2-(3-tert-butoxycarbonylamino-propoxy)-benzyl]-ureido}-thiazole-4-carbonyl)-amino]-acetic acid (7.08 g, 13.9 mmol) and HATU (5.8 g, 15.2 mmol) in THF (150 mL) at room temperature under nitrogen was added DIPEA (13.9 g, 107.7 mmol). Then the reaction mixture was stirred at room temperature for another 20 minutes. Compound (R)-ethyl 3-amino-3-(pyridin-3-yl)propanoate hydrochloride (4.45 g, 16.8 mmol) was added in one portion, and the reaction was stirred at this temperature for 16 hours. The solvent was evaporated and the residue was dissolved in 500 mL of ethyl acetate, washed with 0.3 N HCl (2×100 mL), brine (100 mL) and dried to give a crude product which was purified by silica gel chromatography (eluting with 10% methanol in ethyl acetate) to give the title compound (7.2 g, 77.3%) as solid. LC-MS: 684.2 [M+H]+, tR=2.60 min.

Preparation of (R)-ethyl 3-(2-(2-(3-(2-(3-amino-propoxyl)benzyl)ureido)thiazole-4 carboxamido)acetamido)-3-(pyridin-3-yl)propanoate hydrochloride To a stirred solution of (R)-ethyl 3-(2-(2-(3-(2-(3-(tert-butoxycarbonylamino)propoxy)benzyl)ureido)thiazole-4-carboxamido)acetamido)-3-(pyridin-3-yl)propanoate (2.3 g, 3.36 mmol) in ethanol (50 mL) was added acetyl chloride (5 mL) at 0° C. Then the solution was stirred at room temperature for 1 hour. The solvent was removed at reduced pressure and the residue was washed with ethyl acetate (100 mL) to give the title compound (1.1 g, 52.6%) as a white solid. 1H NMR (300 MHz, CD3OD): δ 8.97 (s, 1H), 8.83-8.81 (m, 1H), 8.73 (d, 1H, J=8.1 Hz), 8.13 (d, 1H, J=7.0 Hz), 7.73-7.75 (m, 1H), 7.34-7.28 (m, 2H), 7.04-6.96 (m, 2H), 5.56-5.51 (m, 1H), 4.49 (s, 2H), 4.23-4.07 (m, 6H), 3.26 (t, 2H, J=6.9 Hz), 3.11 (d, 2H, J=6.9 Hz), 2.26-2.22 (m, 2H), 1.24 (t, 3H, J=7.0 Hz). LC-MS: 584.0 [M+H]+, tR=2.17 min. HPLC: 100% at 214 nm, 100% at 254 nm, tR=5.91 min.

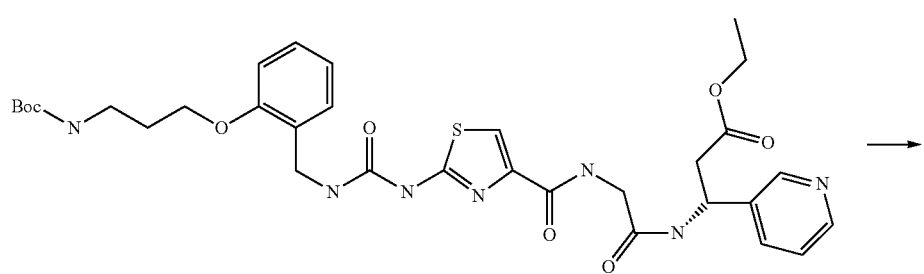

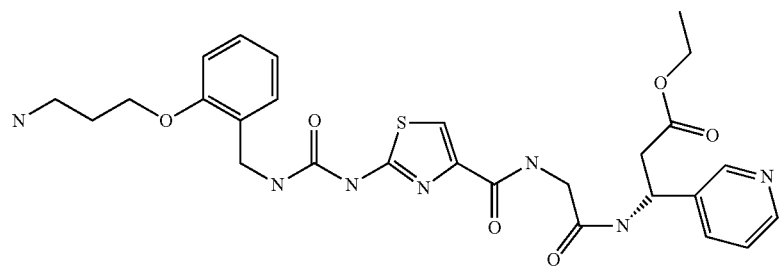

Preparation of (R)-3-(2-(2-(3-(2-(3-aminopropoxyl)
benzyl)ureido)thiazole-4-carboxamido)acetamido)-
3-(pyridin-3-yl)-propionic acid αVβ3 Ligand-5

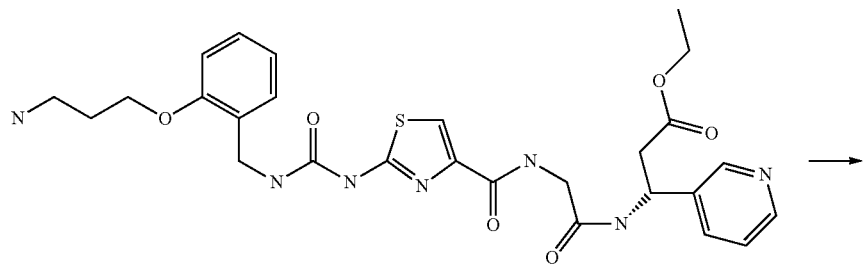

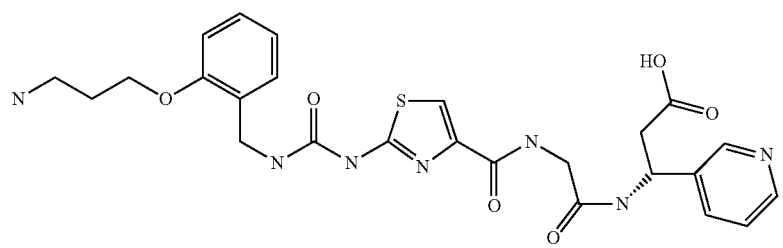

To a solution of (R)-ethyl 3-(2-(2-(3-(2-(3-amino-propoxyl)benzyl)ureido)thiazole-4-carboxamido)acetamido)-3-(pyridin-3-yl)propanoate dihydrochloride (1.99 g, 3.1 mmol) in MeOH (10 mL) was added 2 N sodium hydroxide (15.5 mL, 31.0 mmol) and the resulting reaction mixture was stirred at 55° C. overnight. Then it was neutralized with 1 N hydrochloric acid and purified by reverse-phase HPLC to yield 1.10 g of the title compound.

Example 11

Preparation of αVβ3 Ligand Reagent 9

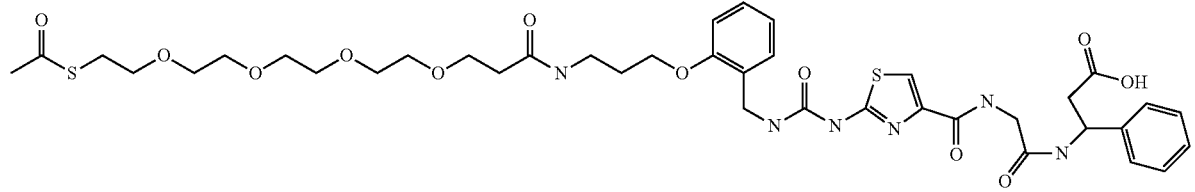 [SMILES: CC(=O)SCCOCCOCCOCCOCCC(=O)NCCCOc1ccccc1CNC(=O)Nc1nc(C(=O)NCC(=O)NC(CC(=O)O)c2ccccc2)cs1]

The title compound was prepared in a similar manner with 3-{2-[(2-{3-[2-(3-amino-propoxy)-benzyl]-ureido}-thiazole-4-carbonyl)-amino]-acetylamino}-3-phenyl-propionic acid and 3-(2-{2-[2-(2-acetylsulfanyl-ethoxy)-ethoxy]-ethoxy}-ethoxy)-propionic acid 2,5-dioxo-pyrrolidin-1-yl ester as shown in Example 7. HRMS m/e 883.2978 (M+Na)+

Example 12

Preparation of αVβ3 Ligand Reagent 10

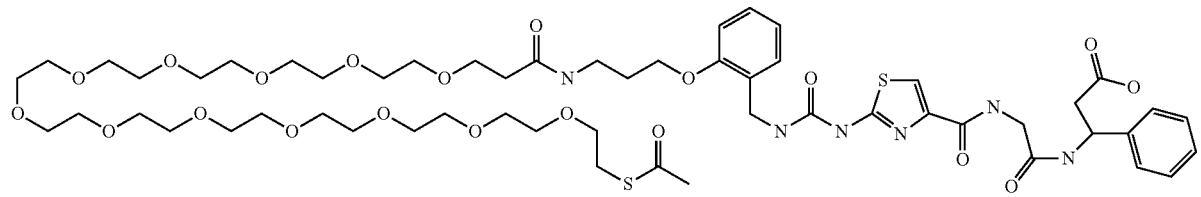 [SMILES: CC(=O)SCCOCCOCCOCCOCCOCCOCCOCCOCCOCCOCCOCCOCCC(=O)NCCCOc1ccccc1CNC(=O)Nc1nc(C(=O)NCC(=O)NC(CC(=O)O)c2ccccc2)cs1]

The title compound was prepared in a similar manner with 3-{2-[(2-{3-[2-(3-amino-propoxy)-benzyl]-ureido}-thiazole-4-carbonyl)-amino]-acetylamino}-3-phenyl-propionic acid and 1-(S-acetyl)-mercapto-3,6,9,12,15,18,21,24,27,30,33,36-dodecaoxanonatriacontan-39-oic acid N-hydroxysuccinimidyl ester as shown in Example 7. HRMS m/e 1213.5248 (M+H)+

Example 13

Preparation of αVβ3 Ligand Reagent 11

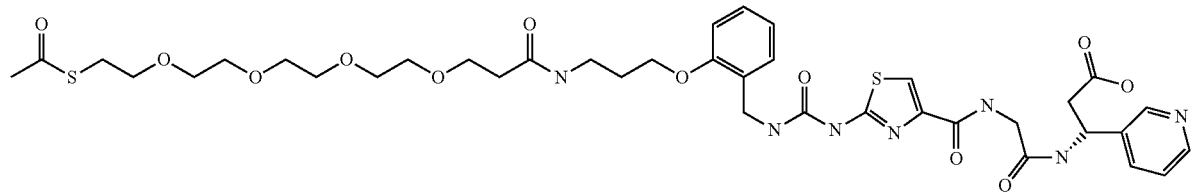

The title compound was prepared in a similar manner with (R)-3-(2-(2-(3-(2-(3-aminopropoxyl)benzyl)ureido)thiazole-4-carboxamido)acetamido)-3-(pyridin-3-yl)-propionic acid TFA and 3-(2-{2-[2-(2-acetylsulfanyl-ethoxy)-ethoxy]-ethoxy}-ethoxy)-propionic acid 2,5-dioxo-pyrrolidin-1-yl ester as shown in Example 7. HRMS m/e 884.2924 (M+H)+

Example 14

Preparation of αVβ3 Ligand Reagent 12

The title compound was prepared in a similar manner with (R)-3-(2-(2-(3-(2-(3-aminopropoxyl)benzyl)ureido)thiazole-4-carboxamido)acetamido)-3-(pyridin-3-yl)-propionic acid TFA and 1-(S-acetyl)-mercapto-3,6,9,12,15,18,21,24,27,30,33,36-dodecaoxanonatriacontan-39-oic acid N-hydroxysuccinimidyl ester as shown in Example 7. HRMS m/e 1214.5205 (M+H)+.

Preparation of Fluorescein (FITC) Labeled Targeting Reagents

The targeting reagents may be derivatized with fluorophores that may be useful for studying their binding tracking to cells that express receptors to the targeting small molecules. Such molecules may be made in either or both of two methods. First, it is possible to perform the reaction of the targeted maleimides with 2-[(5-fluoroseinyl)aminocarbonyl]ethylmercaptane. Alternatively, the one-pot reaction of the integrin antagonist small molecule targeting ligands, with 2-[(5-fluoroseinyl)aminocarbonyl]ethylmercaptane and the bi-functional PEG reagent which is shown in Schemes 17 and 18.

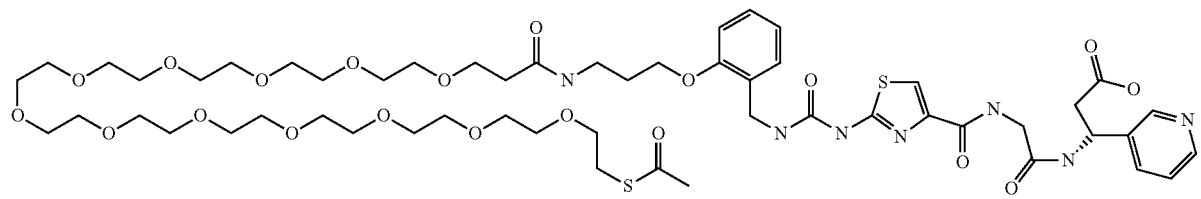

Example of Method a

Preparation of (S)—N-[4-[3-[3-[2-[2-[2-[2-[2-[2-[2-[2-[2-[2-[2-[3-(2,5-dioxo- 2,5-dihydro-pyrrol-1-yl)-propionylamino]ethoxy]ethoxy]ethoxy]ethoxy]ethoxy]ethoxy]ethoxy]ethoxy]ethoxy]ethoxy]-propionylamino]propoxy]-phenyl]-3-[2-[3-(guanidino)benzoylamino]-acetylamino]-succinamic acid-FITC

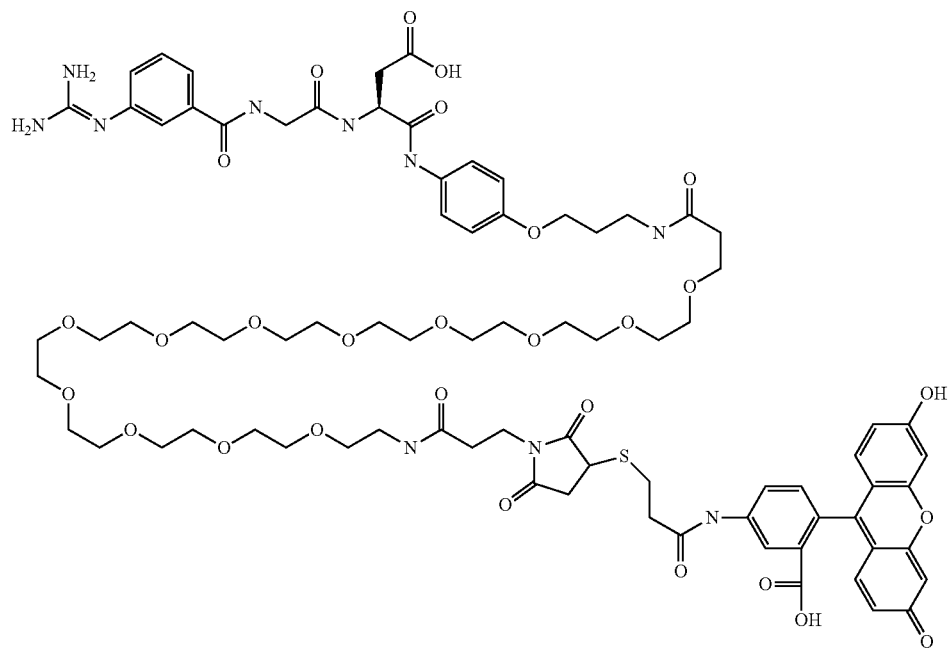 [SMILES: NC(N)=Nc1cccc(C(=O)NCC(=O)N[C@@H](CC(=O)O)C(=O)Nc2ccc(OCCCNC(=O)CCOCCOCCOCCOCCOCCOCCOCCOCCOCCOCCOCCOCCNC(=O)CCN3C(=O)CC(SCCC(=O)Nc4ccc(-c5c6ccc(=O)cc-6oc6cc(O)ccc56)c(C(=O)O)c4)C3=O)cc2)c1]

To an yellow suspension of (S)—N-[4-[3-[3-[2-[2-[2-[2-[2-[2-[2-[2-[2-[2-[2-[3-(2,5-dioxo-2,5-dihydro-pyrrol-1-yl)-propionylamino]ethoxy]ethoxy]ethoxy]ethoxy]ethoxy]ethoxy]ethoxy]ethoxy]ethoxy]ethoxy]-propionylamino]propoxy]-phenyl]-3-[2-[3-(guanidino)-benzoylamino]-acetylamino]-succinamic acid (37.5 mg, 0.03 mmol) and 2-[(5-fluoroseinyl)aminocarbonyl]ethyl-mercaptane (FITC reagent) (15.6 mg, 0.036 mml) in methanol (5 mL) was added an excess of DIPEA (38.7 mg, 52 uL, 0.3 mmol) at room temperature under nitrogen atmosphere. The resulting light yellow suspension was stirred for 2 h at which time LCMS analysis indicated the absence of starting material. Then, the excess DIPEA was removed under vacuum and the desired product was isolated by purification using HPLC to obtain 25 mg (50% yield) of (S)—N-[4-[3-[3-[2-[2-[2-[2-[2-[2-[2-[2-[2-[2-[3-(2,5- dioxo-2,5-di-hydro-pyrrol-1-yl)-propionylamino]ethoxy]ethoxy]ethoxy]ethoxy]ethoxy]ethoxy]ethoxy]ethoxy]ethoxy]ethoxy]-propionylamino]propoxy]-phenyl]-3-[2-[3-(guanidino)benzoylamino]-acetylamino]-succinamic acid-FITC derivative as a brown solid.

ES(+)-HRMS m/e calcd. for $C_{80}H_{104}N_{10}O_{28}S$ (M+2H)2+ 843.3444, obsd. 843.3437. LCMS data=M+H, 1687.6

Example of Method b

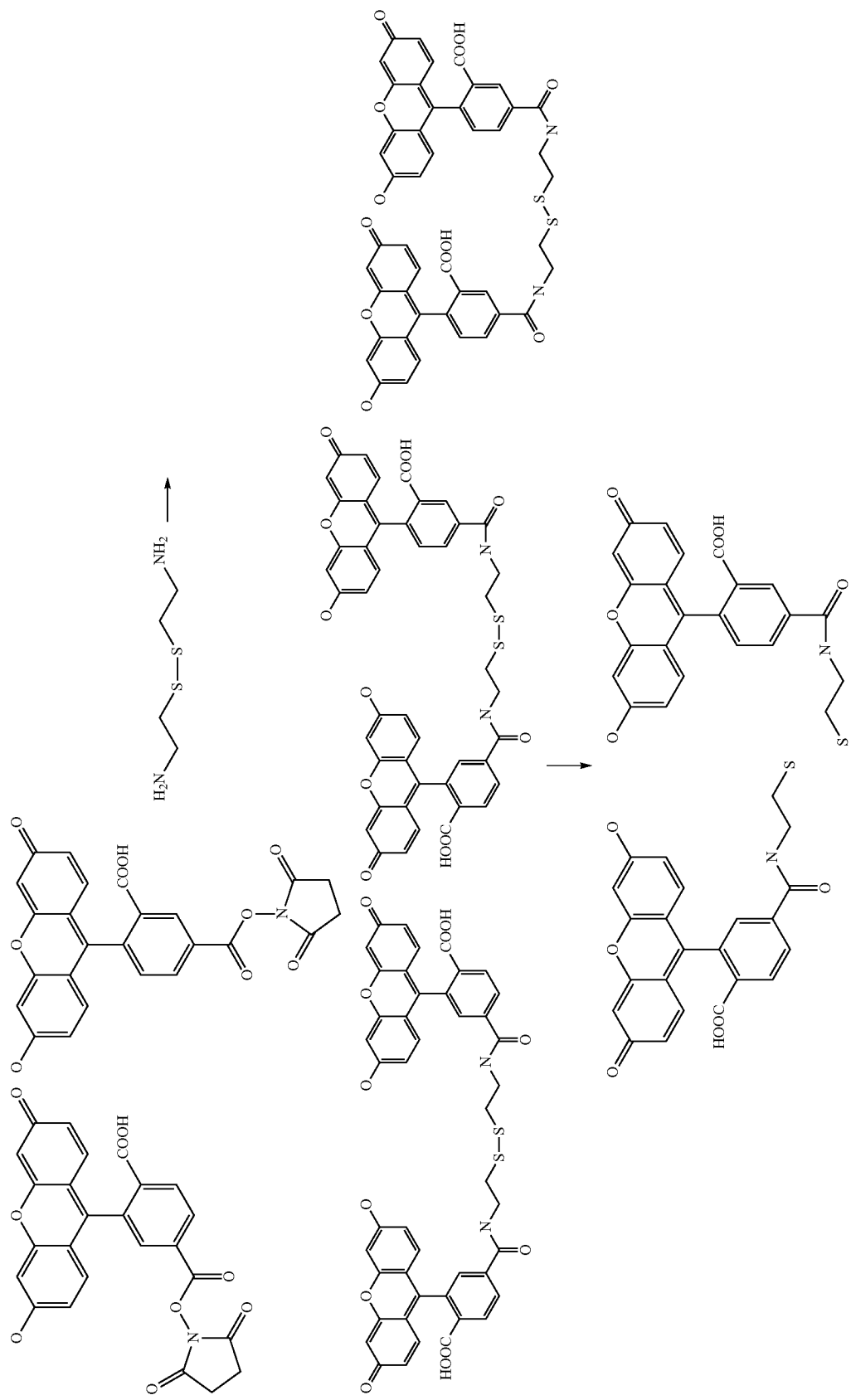

Step 1. Cystamine dihydrochloride (68 mg, 0.301 mmol) and DIEA (110 µL, 2.1 eq.) were dissolved in DMF (10 mL), followed by addition of NHS-fluorescein, a mixture of 5- and 6-carboxyfluorescein (300 mg, 0.634 mmol) and the resulting reaction mixture was stirred overnight at room temperature. Then it was diluted with ethyl acetate and washed three times with water and one time with brine. The extract was dried over anhydrous sodium sulfate, concentrated under reduced pressure, redissolved in small amount of methanol and ethyl acetate, and then triturated with diethyl ether to obtain 140 mg of fluorescein-cystamine adduct as a bright orange solid.

Step 2. The fluorescein-cystamine adduct (80 mg, 0.092 mmol) was dissolved in a 3:1 mixture of methanol and water (4 mL) and TCEP hydrochloride (80 mg, 3 eq.) was added. The resulting reaction mixture was stirred at room temperature for 2 h. The product was purified by HPLC to yield 78 mg of the product. LRMS (ESI) 435.0

Preparation of fluorescein-labeled small molecule-PEG conjugates

Oligoribonucleotide Synthesis

Oligoribonucleotides were synthesized according to the phosphoramidite technology on solid phase employing an ABI 394 synthesizer (Applied Biosystems) at the 10 µmol scale. For RNA sequence information see tables 1 and 2. The corresponding siRNAs are directed against the house keeping gene AHAL Syntheses were performed on a solid support made of controlled pore glass (CPG, 520 Å, with a loading of 75 µmol/g, obtained from Prime Synthesis, Aston, Pa., USA). Regular RNA phosphoramidites, 2'-O-Methyl-phosphoramidites as well as ancillary reagents were purchased from Proligo (Hamburg, Germany). Specifically, the following amidites were used: (5'-O-dimethoxytrityl-N6-(benzoyl)-2'-O-t-butyldimethylsilyl-adenosine-3'-O-(2-cyanoethyl-N,N-diisopropylamino)phosphoramidite, 5'-O-dimethoxytrityl-N4-(acetyl)-2'-O-t-butyldimethylsilyl-cytidine-3'-O-(2-cyanoethyl-N,N-diisopropylamino)phosphoramidite, (5'-O-dimethoxytrityl-N-2-(isobutyryl)-2'-O-t-butyldimethylsilyl-guanosine-3'-O-(2-cyanoethyl-N,N-diisopropylamino)phosphoramidite, and 5'-O-dimethoxytrityl-2'-O- t-butyldimethylsilyluridine-3'-O-(2-

Scheme 18

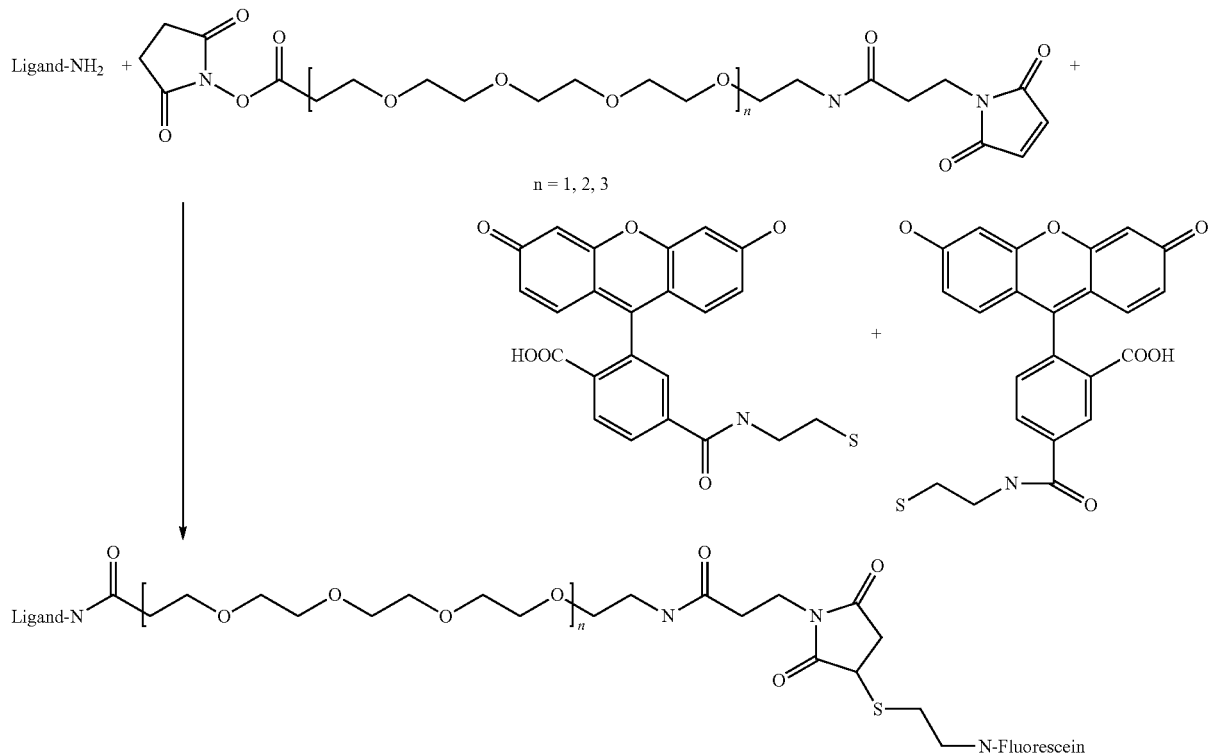

General Procedure:

To a solution of ligand (1 eq.) in DMSO was added DIEA (2 eq.) and SM(PEG)4n (1 eq.). The resulting reaction mixture was stirred at room temperature for 1 h. Next, fluorescein with thiol handle (1 eq.) was added and the reaction mixture was stirred for an additional 10 min. The product was purified by HPLC.

Procedures for Covalent Attachment to Small Molecule Integrin Targeting Ligands to 5'-Thiol-siRNA Oligonucleotides siRNA preparation.

cyanoethyl-N,N-diisopropylamino)phosphoramidite. 2'-O-Methylphosphoramidites carried the same protecting groups as the regular RNA amidites. All amidites were dissolved in anhydrous acetonitrile (100 mM) and molecular sieves (3 Å) were added. To generate the sulfhydryl linker at the 5'-end of the oligomer the 1-O-Dimethoxytritylhexyl-disulfide, 1'-[(2-cyanoethyl)-(N,N-diisopropyl)]-phosphoramidite linker from Glen Research (Sterling, Va., USA) was used. Prior to small molecule conjugation the disulfide linker was reduced using Tris-(2-carboxyethyl)phosphine (TCEP, see below). For 5'-end labeling with the Nu547 fluorophore the corresponding phosphoramidite obtained from Thermo Fisher (Milwaukee, Wis.) was employed. 5-Ethyl thiotetrazole (ETT, 500 mM in acetonitrile) was used as activator solution. Coupling times were 6 minutes. In order to introduce phosphorothioate linkages a 100 mM solution of 3-ethoxy-1,2,4-dithiazoline-5-one (EDITH, obtained from Link Technologies, Lanarkshire, Scotland) in anhydrous acetonitrile was employed.

Cleavage and Deprotection of Support Bound Oligomer

After finalization of the solid phase synthesis, the dried solid support was transferred to a 15 mL tube and treated with methylamine in methanol (2M, Aldrich) for 180 min at 45° C. After centrifugation the supernatant was transferred to a new 15 mL tube and the CPG was washed with 1200 µL N-methylpyrolidin-2-one (NMP, Fluka, Buchs, Switzerland). The washing was combined with the methanolic methylamine solution and 450 µL Triethylamine trihydrofluoride (TEA.3HF, Alfa Aesar, Karlsruhe, Germany) was added. This mixture was brought to 65° C. for 150 min. After cooling to room temperature 0.75 mL NMP and 1.5 mL of ethoxytrimethylsilane (Fluka, Buchs, Switzerland) was added. 10 min later, the precipitated oligoribonucleotide was collected by centrifugation, the supernatant was discarded and the solid was reconstituted in lmL buffer A (see below).

Purification of Oligoribonucleotides

Crude oligoribonucleotides were purified by strong anion exchange (SAX) HPLC employing a preparative 22×250 mm DNA Pac 100 column (Dionex, Idstein, Germany) on an AKTA Explorer system (GE Healthcare). Buffer A consisted of 10 mM NaClO4, 1 mM EDTA, 10 mM Tris, pH 7.4, 6M Urea and 20% acetonitrile. Buffer B had 500 mM NaClO4 in Buffer A. A flow rate of 4.5 mL/min was employed. UV traces at 260 and 280 nm were recorded. A gradient of 20% B to 45% B within 55 min was employed. Appropriate fractions were pooled and precipitated with 3M NaOAc, pH=5.2 and 70% Ethanol.

Crude Nu547 labeled oligomers were purified by RP HPLC using a XTerra Prep MS C8 10×50 mm column (Waters, Eschborn, Germany) on an AKTA Explorer system (GE Helthcare). Buffer A was 100 mM triethylammonium acetate (Biosolve, Valkenswaard, The Netherlands) and buffer B contained 50% acetonitrile in buffer A. A flow rate of 5 mL/min was employed. UV traces at 260, 280 and 547 nm (in case of Nu547 labeled oligoribonucleotide) were recorded. A gradient of 5% B to 60% B within 58 column volumes (CV) was employed. Appropriate fractions were pooled and precipitated with 3M NaOAc, pH=5.2 and 70% Ethanol.

Finally, the purified oligomer was desalted by size exclusion chromatography on a column containing Sephadex G-25 (GE Healthcare). The concentration of the solution was determined by absorbance measurement at 260 nm in a UV photometer (Beckman Coulter, Krefeld, Germany). Until annealing the individual strands were stored as frozen solutions at −20° C.

Preparation of Small Molecule RNA Conjugates

Small molecules equipped with a maleimide functionality were covalently conjugated to the RNA through a thioether linkage. To enable this chemistry, ~60 mg of the RNA containing the 5'-disulfide linker was reduced in water (5 mL) to the corresponding thiol using 1 mL TCEP (0.5 M in water, obtained from Sigma Aldrich). Once analytical anion exchange HPLC indicated completion of the reaction (~2 h at room temperature) the RNA was precipitated with 30 mL ethanol/3M NaOAc (pH 5.4) 32:1 (v/v) over night at −20° C. The pellet was collected by centrifugation and used for the subsequent small molecule conjugation.

In a typical conjugation reaction 10 mg RNA was dissolved in 2 mL sodium phosphate buffer (0.1 M, pH 7.0). To this solution the small molecule (0.12 mM) in ACN/NMP 1:1 (v/v) was added over a period of 5 minutes. Once RP LC-ESI MS showed consumption of the input RNA the mixture was diluted with water (~10 mL) and ~40 mL ethanol/3M NaOAc (pH 5.4) 32:1 (v/v) was added to precipitate the conjugated RNA over night at −20° C. The pellet was collected by centrifugation, dissolved in water and if necessary purified by anion exchange HPLC pursuing the procedure given above. If the conjugate is sufficiently pure the reaction mixture was filtered through a size exclusion column (Sephadex G-25, GE Healthcare).

Annealing of Oligoribonucleotides to Generate siRNA

Complementary strands were annealed by combining equimolar RNA solutions. The mixture was lyophilized and reconstituted with an appropriate volume of annealing buffer (100 mM NaCl, 20 mM sodium phosphate, pH 6.8) to achieve the desired concentration. This solution was placed into a water bath at 95° C. which was cooled to rt within 3 h.

The following assay was conducted to assess αVβ3 binding affinity of the αVβ3-targeted compounds of this invention.

Human αVβ3 solid phase assay:

Immuno 96-well Plates (NUNC, Part#439454) were coated with αVβ3 (R & D, Cat#3050-AV) by adding 100 uL of αVβ3 (lx) to each well and incubating the plates overnight at 40 C. Buffer used was Buffer A: 20 mM Tris, 150 mM NaCl, 1 mM CaCl2, 1 mM MgCl2, pH7.4. After removal of the coating reagent, 150 uL of 3.5% BSA in Buffer A was added to each well to block the plates for 105 minutes at 370 C. After blocking, plates were washed 5 times with 200 uL of Buffer B (Buffer A+1 mM MnC12). 50 uL of test compound solution (2×) in 5% DMSO and 50 uL of fibrinogen (2×) (Innovative Research, Cat# IFIB) were then added to each well. Plates were shaken for 2 minutes, and then incubated for 2 hours for 370 C. After the plates were washed 5 times with 200 uL of Buffer B, the 1st antibody rabbit anti-human fibrinogen (Innovative Research, Cat IASHFBGN-GF) in the amount of 100 uL/well, and the 2nd antibody Goat anti-rabbit IgG Horseradish peroxidase conjugate (Invitrogen, Cat#G21234) in the amount of 50 uL/well were added to plates, respectively. After the addition of 1st antibody and after the addition of 2nd antibody, plates were shaken for 2 minutes and incubated for 60 minutes at 370 C, and then washed 5 times with 200 uL of Buffer B correspondingly. The final conditions of the solid phase assay were: [αvβ3]=1.25 ug, [fibrinogen]=0.75 ug/mL, [Anti-FG]=1/2400 (diluted), [HPR-Anti-rabbit]=1/1000 (diluted). When the binding assay was completed, 100 uL/well of detection reagent ABTS (mixture of reagent A and reagent B) (KPL, Cat#50-62-00) was added to plates. Plates were shaken at RT for 5-8 min, and the development of a green color was gradually showing. After being added 100 uL/well Stop Buffer (1.0 M Phosphoric Acid (HPO4)), plates were read on Envision at Absorbance mode 450 nm.

The control compound (141) was determined to have an IC50 of about 2 nM (i.e. 50% of the cells did not bind to αVβ3 on the surface of the wells since the αVβ3 receptors of the cells were presumably bound to or associated with the control compound). These results are shown below in the Table 3 and 4.

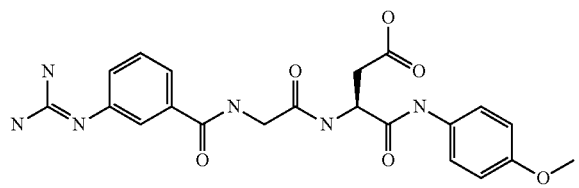

141

Evidence of Cellular Permeability and Localization of Small Molecule Derivatives for Covalently Linked Integrin Antagonists to FITC Fluorophores and siRNA for Targeted Delivery Procedure AML MV4-11 cells in growth medium (RPMI 1640 with 10% FBS) were incubated with Duplex-27 (500 nM) for 1 hour at 37° C. For determining VLA-4 independent binding, 140 (10 μM) was included in one condition to block VLA-4 dependent binding. After incubation, the cells were then washed twice with D-PBS and fixed in 1% paraformaldehyde for 10 minutes. The uptake of siRNA was analyzed by imaging flow cytometry using ImageStreamx (Aminis Corporation, Seattle). The results are shown in Table A and in FIGS. 1-4.

TABLE A

| Compound (concentration) | Mean Cy3 intensity |
|---|---|
| Nothing | 638 |
| 140 (10 μM) | 663 |
| Duplex-27 (500 nM) | 4007 |
| 140 (10 μM) + Duplex-27 (500 nM) | 2273 |

Assay of 5'-Sense Strand Modified siRNA for Knock-Down of AHA1 mRNA in Cellular Systems Materials and Methods
Reference gene: GAPDH
Cell line: H1299_Nut-Onc
Plating density: 5,000 cells/well
Plating format: 96-well
Time from plating to treatment: 0
Control treatment: mock, untreated, control siRNA
Transfection reagent: DharmaFect1
Transfection Method Reverse TF
TF Reagent volume/well 0.15 mL
siRNA final concentration 50 nM
Assay method: Day 1 manual/Day 2 Washer Reverse transfection: H1299 cells were transfected with indicated siRNA at final concentration of 50 nM using DharmaFect-1 transfection reagent at 0.15 μl/well. Cells were then plated into 96-well plate at 5000 cells/well and incubated at 37° C. for 48 hours.

Figure 5:
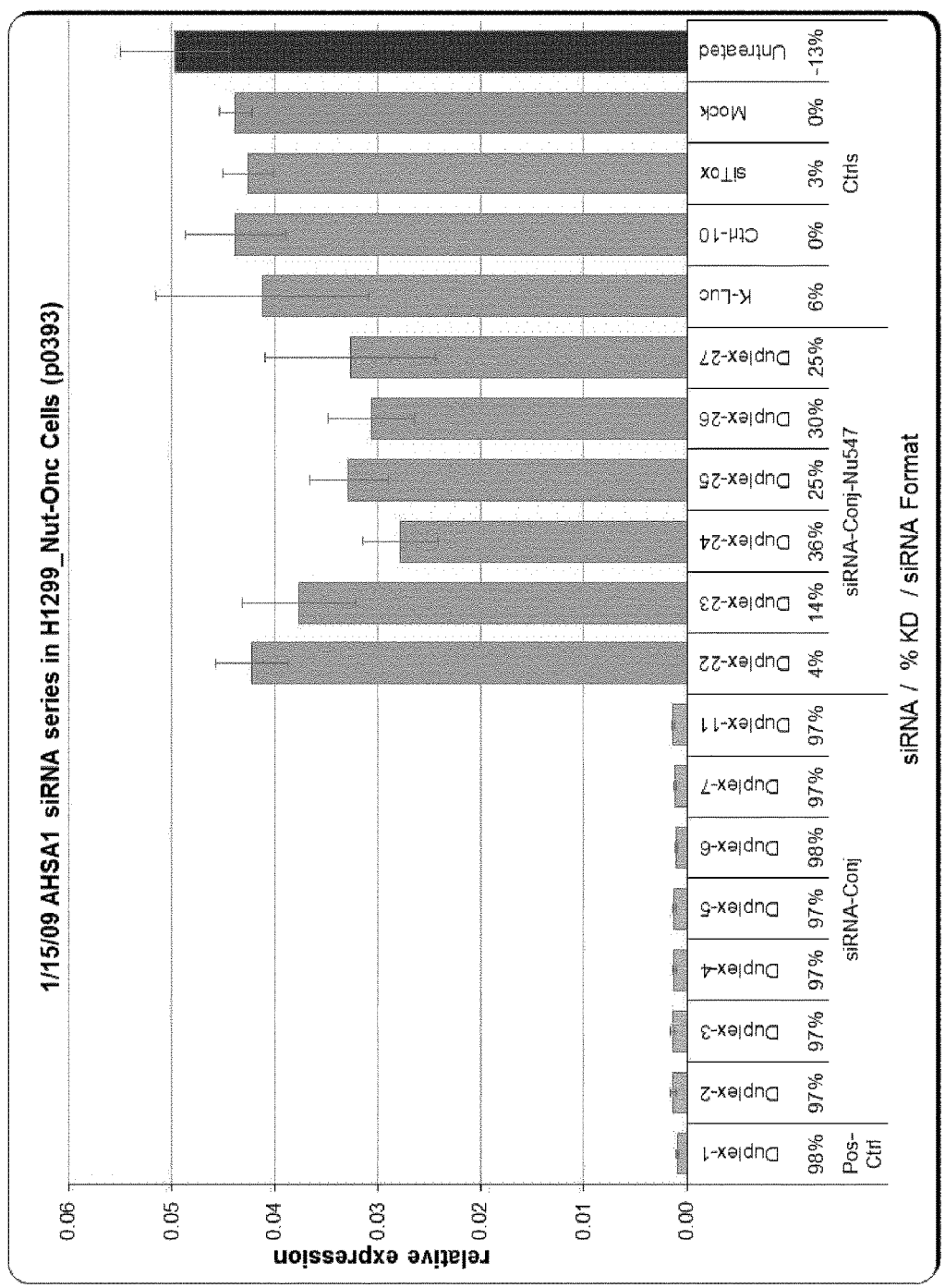
FIG. 5 shows the reduction of AHA1 expression in H1299 cells when treated with siRNA duplexes which have been derivatized on the 5'-sense strand with an integrin targeting small molecule. The y-axis indicates the observed expression level of AHA1. The lower bar indicates a greater degree of knock-down (a higher degree of siRNA transfection); a high bar, a lesser degree of knock-down (i.e., a lesser degree of siRNA transfection). Duplexes in blue have targeting modifications on the 5'-end of the sense strand; those in pink have targeting modifications on the 5'-end of the sense strand as well as Nu547 fluorophore attached to the 5'-end of the antisense strand.
Figure 6:
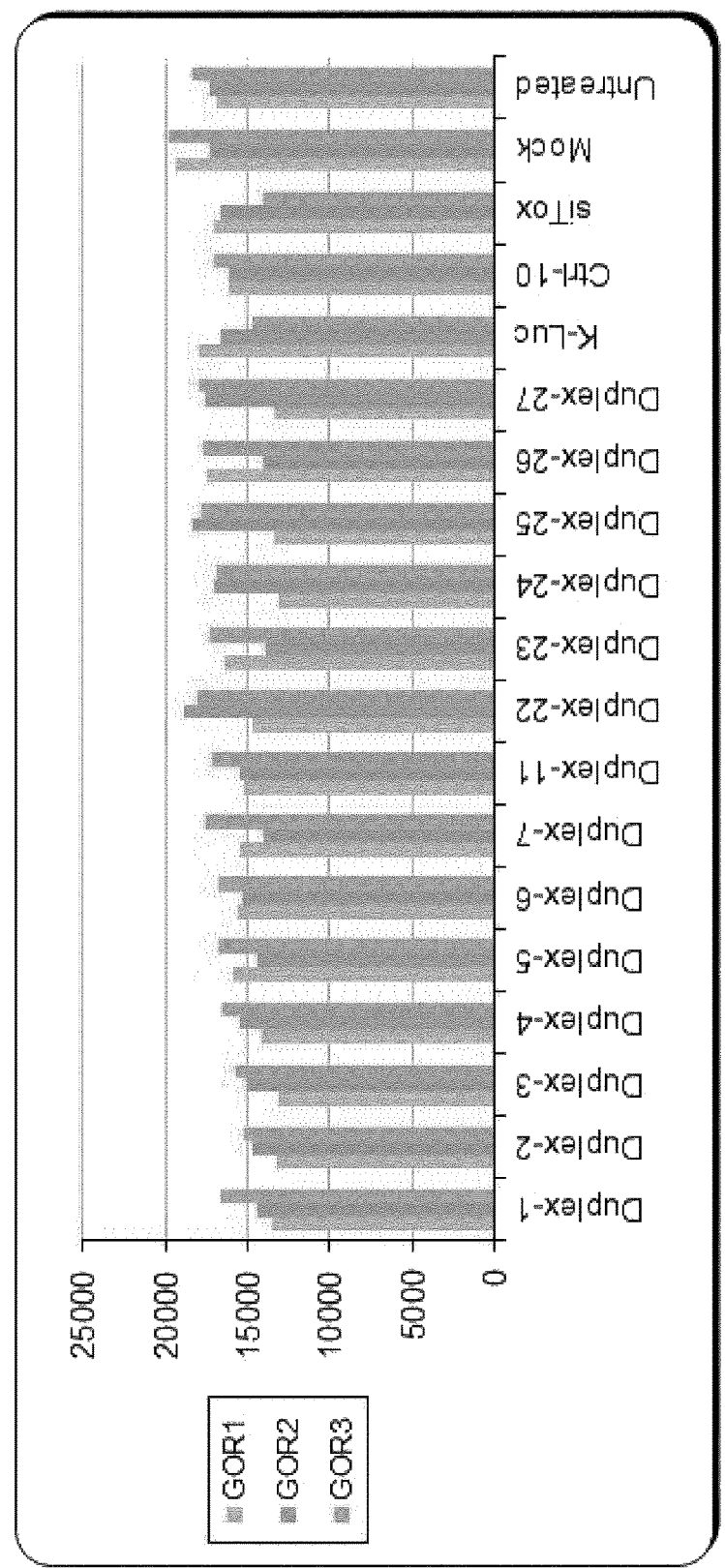
FIG. 6 shows the levels of GAPDH mRNA expression, a marker of cell health. The similarity of the expression levels for those cells treated with derivatized siRNA to that of the mock and untreated cells is an indication of the lack of cellular toxicity at the treatment concentration and duration.

The efficacy of siRNA knock-down was measured with a Branched DNA Assay as reported by the vendor; the results of such knockdown are shown in FIG. 5. The relative cell viability was assessed by the absolute expression of GAPDH in the same well (FIG. 6).

Unless stated to the contrary, all compounds in the examples were prepared and characterized as described. All patents and publications cited herein are hereby incorporated by reference in their entirety.

The invention claimed is:

1. A compound of formula I:

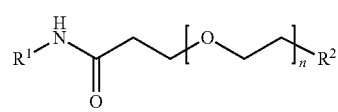

(I)

or a pharmaceutically acceptable salt or ester thereof; wherein n is 1-24 and wherein: $R^1$ is selected from the group consisting of:

89
(1) a moiety of the formula:
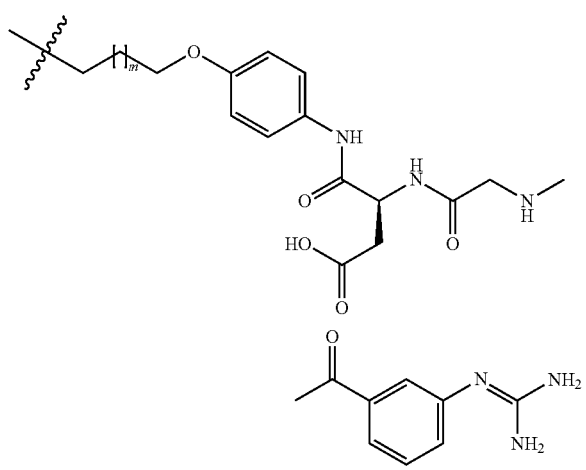
wherein m is 0 or 1;
(2) a moiety of the formula:
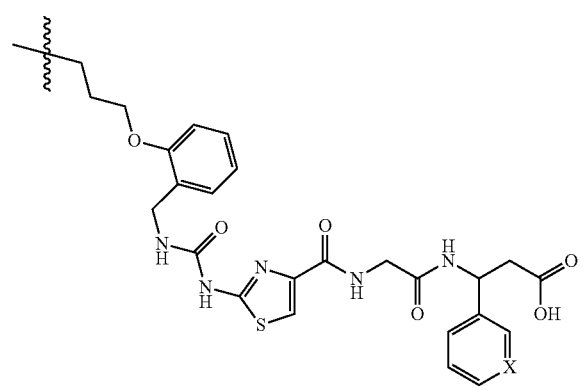
wherein X is N or CH;
(3) a moiety of the formula:
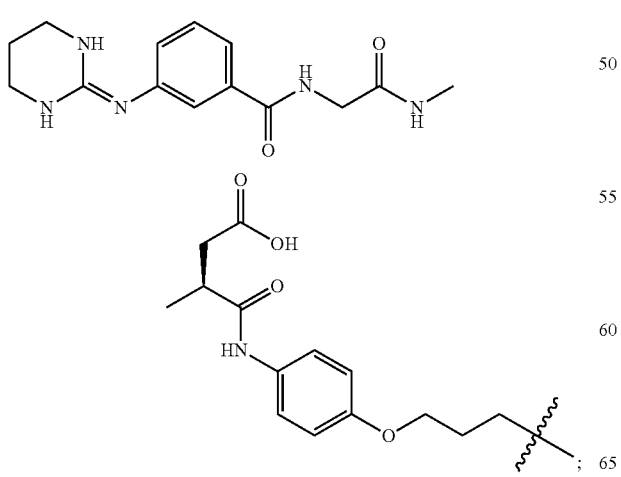
90
(4) a moiety of the formula:
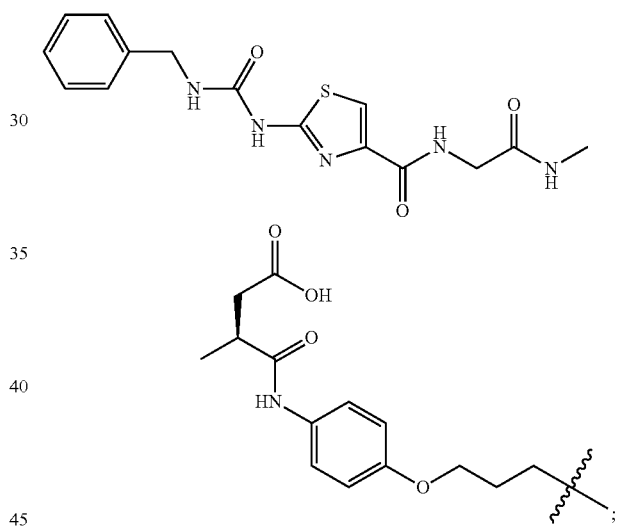
and
(5) a moiety of the formula:
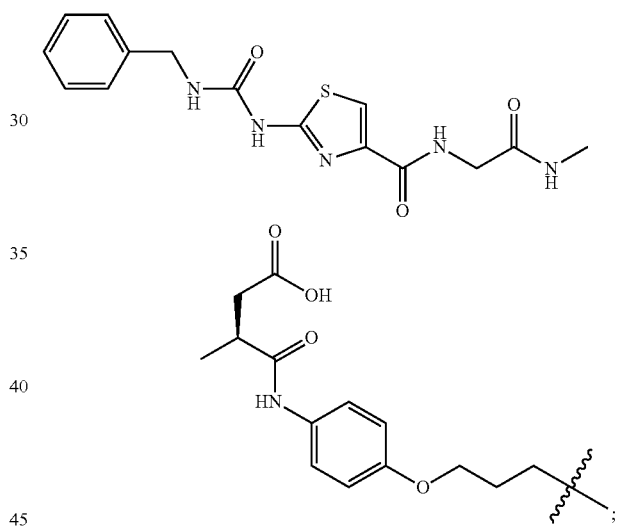
$R^2$ is selected from the group consisting of:
(1) a moiety of the formula:
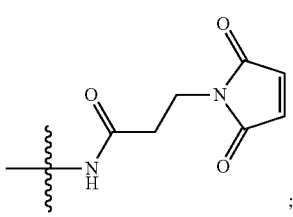 [SMILES: *NC(=O)CCN1C(=O)C=CC1=O]
(2) a moiety of the formula:
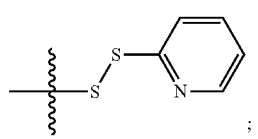 [SMILES: *SSc1ccccn1]

(3) a moiety of the formula:
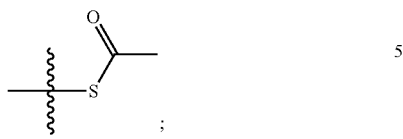
and
(4) a moiety of the formula:
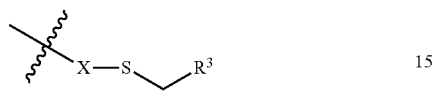
wherein $R^3$ is a conjugated moiety and X represents either sulfur or a moiety of the formula:
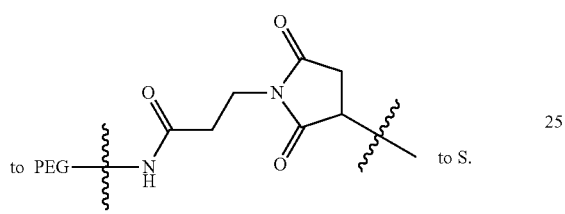
2. A compound according to claim 1, wherein $R^1$ is a moiety of the formula:
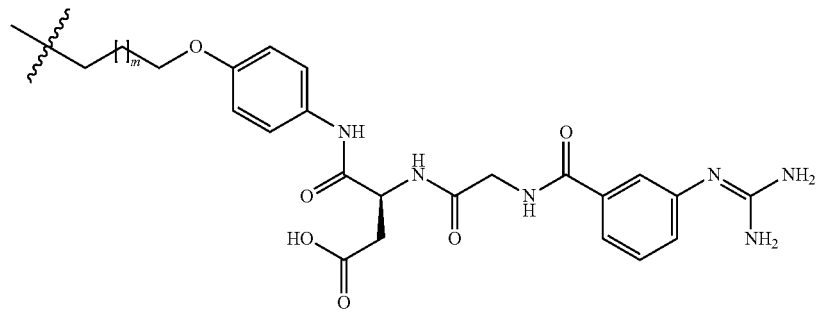
wherein m is 0 or 1.
3. A compound according to claim 1, wherein $R^1$ is a moiety of the formula:
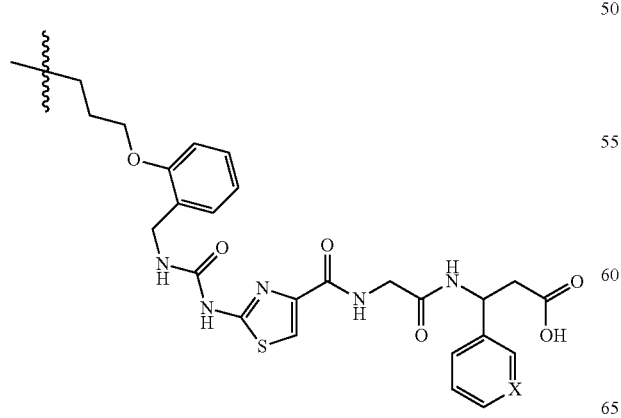
wherein X is N or CH.

4. A compound according to claim 1, wherein R¹ is a moiety of the formula:
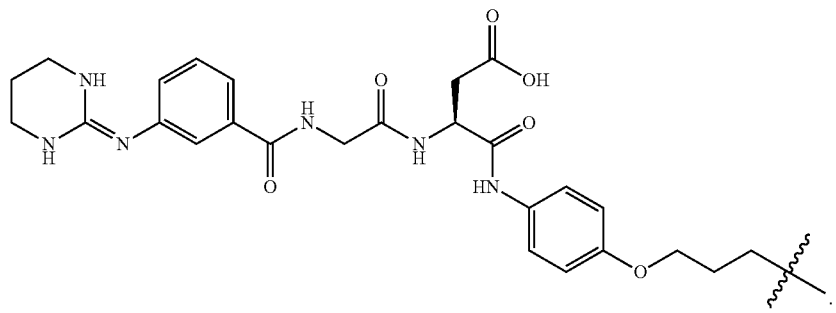 [SMILES: *CCCOc1ccc(NC(=O)[C@H](CC(=O)O)NC(=O)CNC(=O)c2cccc(N=C3NCCCN3)c2)cc1]
5. A compound according to claim 1, wherein R¹ is a moiety of the formula:
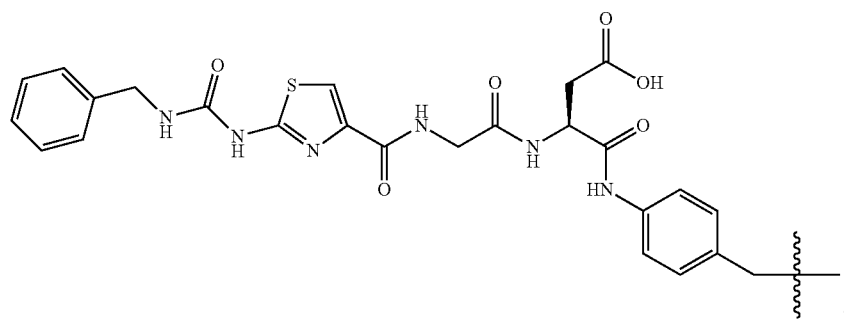 [SMILES: *Cc1ccc(NC(=O)[C@H](CC(=O)O)NC(=O)CNC(=O)c2csc(NC(=O)NCc3ccccc3)n2)cc1]
6. A compound according to claim 1, wherein R¹ is moiety of the formula:
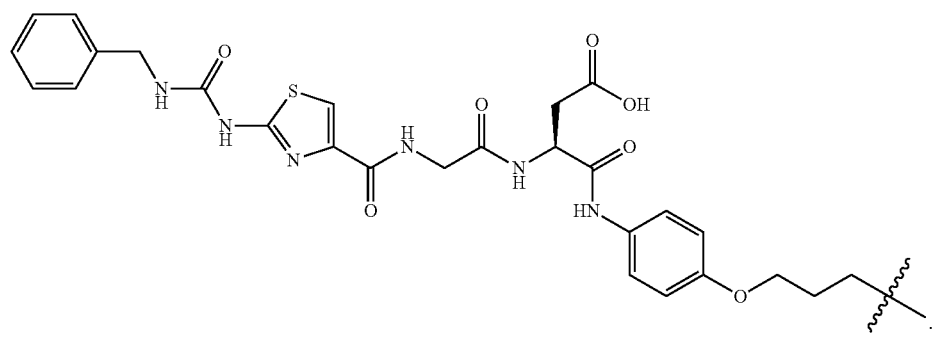 [SMILES: *CCCOc1ccc(NC(=O)[C@H](CC(=O)O)NC(=O)CNC(=O)c2csc(NC(=O)NCc3ccccc3)n2)cc1]
7. A compound according to claim 1, wherein R² is a moiety of the formula:
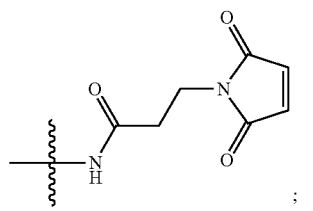
;
wherein R² is a moiety of the formula:
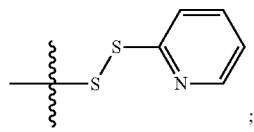
;

wherein R² is a moiety of the formula:

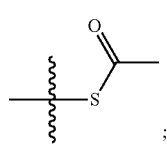 [SMILES: *SC(C)=O]

or wherein R² is a moiety of the formula:

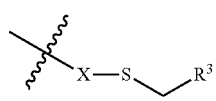

wherein R³ is a single or double stranded oligonucleotide and X represents either sulfur or a moiety of the formula:

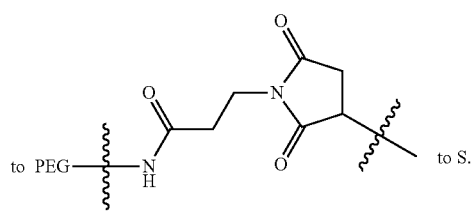

8. A compound according to claim 2, wherein R² is a moiety of the formula:

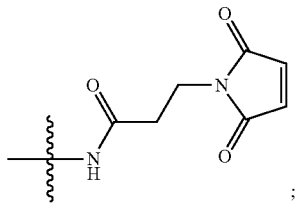

wherein R² is a moiety of the formula:

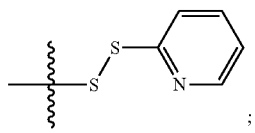

wherein R² is a moiety of the formula:

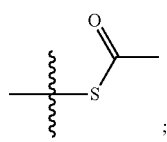 [SMILES: *SC(C)=O]

or wherein R² is a moiety of the formula:

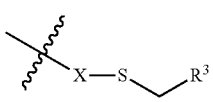

wherein R³ is a single or double stranded oligonucleotide and X represents either sulfur or a moiety of the formula:

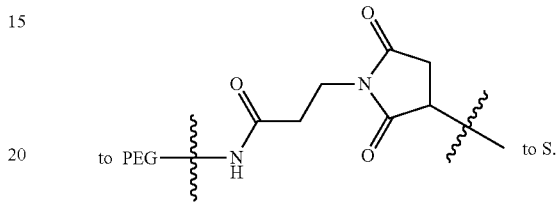

9. A compound according to claim 3, wherein R² is a moiety of the formula:

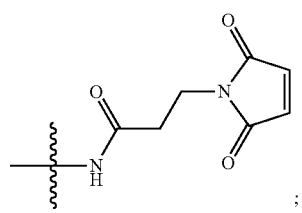

wherein R² is a moiety of the formula:

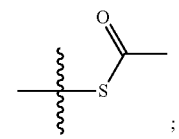

wherein R² is a moiety of the formula:

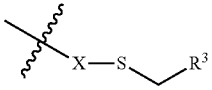

or wherein R² is a moiety of the formula:

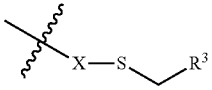

wherein R³ is a single or double stranded oligonucleotide and X represents either sulfur or a moiety of the formula:

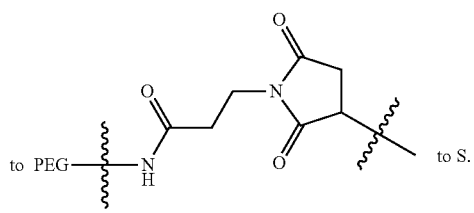

10. A compound according to claim 4, wherein $R^2$ is a moiety of the formula:

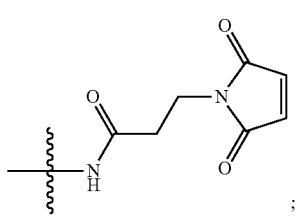

wherein $R^2$ is a moiety of the formula:

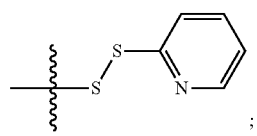

wherein $R^2$ is a moiety of the formula:

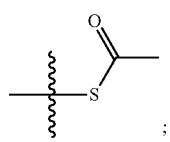 [SMILES: *SC(C)=O]

or
wherein $R^2$ is a moiety of the formula:

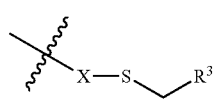

wherein $R^3$ is a single or double stranded oligonucleotide and X represents either sulfur or a moiety of the formula:

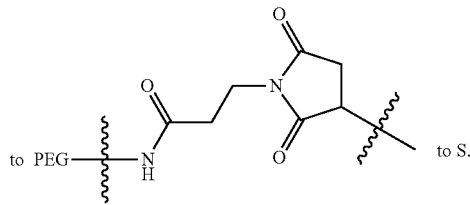

11. A compound according to claim 5, wherein $R^2$ is a moiety of the formula:

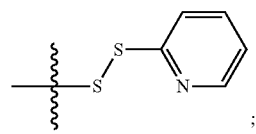

wherein $R^2$ is a moiety of the formula:

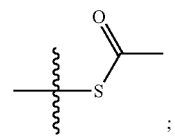

wherein $R^2$ is a moiety of the formula:

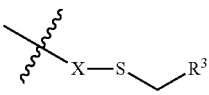

or
wherein $R^2$ is a moiety of the formula:

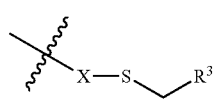

wherein $R^3$ is a single or double stranded oligonucleotide and X represents either sulfur or a moiety of the formula:

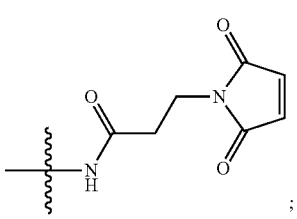

12. A compound according to claim 6, wherein $R^2$ is a moiety of the formula:

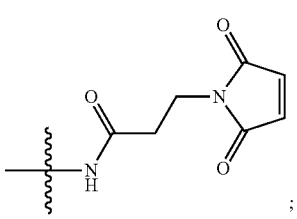

wherein R² is a moiety of the formula:

[structure: pyridyl disulfide]

wherein R² is a moiety of the formula:

[structure: thioester]

wherein R² is a moiety of the formula:

[structure with X—S—R³]

wherein R³ is a single or double stranded oligonucleotide and X represents either sulfur or a moiety of the formula:

[structure: maleimide linker to PEG and to S]

13. A compound according to claim 7, wherein R³ is a siRNA molecule.

14. A compound according to claim 1, wherein R³ is fluorescein isothiocyanate.

15. A compound according to claim 1, selected from the group consisting of:

(S)—N-[4-[3-3-[2-[2-[2-[2-[2-[2-[2-[2-[3-(2,5-dioxo-2,5-dihydro-pyrrol-1-yl)-propionylamino]ethoxy]ethoxy]ethoxy]ethoxy]ethoxy]ethoxy]ethoxy]-propionyamno]propoxy]-phenyl]-3-[2-[3-(guanidino)-benzoylamino]-acetylamino]-succinamic acid;

(S)—N-[4-[3-3-[2-[2-[2-[2-[2-[2-[2-[2-[2-[2-[3-(2,5-dioxo-2,5- dihydro-pyrrol-1-yl)-propionylamino]ethoxy]ethoxy]ethoxy]ethoxy]ethoxy]ethoxy]ethoxy]ethoxy]ethoxy]ethoxy]ethoxy]-propionylamino]propoxy]-phenyl]-3-[2-[3-(guanidino)-benzoylamino]-acetylamino]-succinamic acid;

3-(S)—N-[[[4-[3-[2-[2-[2-[2-[2-[2-[2-(2-acetylsulfanyl-ethoxy)ethoxy]ethoxy]ethoxy]ethoxy]ethoxy]ethoxy]ethoxy]-1-oxopropyl]amino]propoxy]-phenyl]-3-[2-[3-[guanidino]-benzoylamino]-acetylamino]-succinamic acid trifluoroacetate salt;

(S)—N-[[[4-[3-[2-[2-[2-[2-[2-[2-[2-(2-acetylsulfanyl-ethoxy)ethoxy]ethoxy]ethoxy]ethoxy]ethoxy]ethoxy]ethoxy]-1-oxopropyl]amino]propoxy]-phenyl]-3-[2-[3-(tetrahydropyrimidin-2-ylideneamino)-benzoylamino]-acetylamino]-succinamic acid;

(S)—N-[[4-[3-[2-[2-[2-[2-[2-[2-[2-[2-[2-[2-[2-(2-acetylsulfanyl-ethoxy)ethoxy]ethoxy]ethoxy]ethoxy]ethoxy]ethoxy]ethoxy]ethoxy]ethoxy]ethoxy]ethoxy]propionylamino]methyl]phenyl]-3-[2-[[2-(3-benzylureido)thiazole-4-carbonyl]amino]acetylamino]-succinamic acid;

(S)—N-[4-[3-3-[2-[2-[2-[2-[2-[2-[2-[3-(2,5-dioxo-2,5-dihydro-pyrrol-1-yl)-propionylamino]ethoxy]ethoxy]ethoxy]ethoxy]ethoxy]ethoxy]ethoxy]ethoxy]propionylamino]propoxy]-phenyl]-3-[2-[[2-(3-benzyl-ureido)-thiazole-4-carbonyl]-amino]-acetylamino]-succinamic acid (S)—N-[4-[3-3-[2-[2-[2-[2-[2-[2-[2-[2-[2-[2-[3-(2,5-dioxo-2,5- dihydro-pyrrol-1-yl)-propionylamino]ethoxy]ethoxy]ethoxy]ethoxy]ethoxy]ethoxy]ethoxy]ethoxy]ethoxy]ethoxy]ethoxy]ethoxy]propionylamino]ethoxy]-phenyl]-3-[2-[[2-(3-benzyl-ureido)-thiazole-4-carbonyl]-amino]-acetylamino]-succinamic acid; and (S)—N-[4-[3-3-[2-[2-[2-[2-[2-[2-[2-acetylsulfanyl-ethoxy]ethoxy]ethoxy]ethoxy]ethoxy]ethoxy]ethoxy]ethoxy]propionylamino]propoxy]-phenyl]-3-[2-[[2-(3-benzyl-urcido)-thiazole-4-carbonyl]-amino]-acetylamino]-succinamic acid.

16. A compound according to claim 1 which is: (R)-3-[2-{(2-[3-{2-[3-(3-(2-{2-[2-(2-Acetylsulfanyl-ethoxy}-ethoxy)-ethoxy]-ethoxy}-propionylamino)-propoxy]-benzyl}-ureido]-thiazole-4-carbonyl)-amino]-acetylamino]-phenyl-3-yl-propionic acid.

17. A compound according to claim 1 which is 3-[2-{(2-[3-{2-[3-(3-{2-[2-(2-{2-[2-(2-{2-[2-(2-Acetylsulfanyl-ethoxy)-ethoxy]-ethoxy}-ethoxy)-ethoxy]-ethoxy}-ethoxy)-ethoxy]-ethoxy}-ethoxy)-ethoxy]-ethoxy}-propionylamino)-propoxy]-benzyl}-ureido]-thiazole-4-carbonyl)-amino]-acetylamino]-phenyl-3-yl-propionic acid.

18. A compound according to claim 1 which is: (R)-3-[2-{(2-[3-{2-[3-(3-(2-{2-[2-(2-Acetylsulfanyl-ethoxy}-ethoxy)-ethoxy]-ethoxy}-propionylamino)-propoxy]-benzyl}-ureido]-thiazole-4-carbonyl)-amino]-acetylamino]-3-pyridin-3-yl-propionic acid.

19. A compound according to claim 1 which is: (R)-3-[2-{(2-[3-{2-[3-(3-{2-[2-(2-{2-[2-(2-{2-[2-(2-Acetylsulfanyl-ethoxy)-ethoxy]-ethoxy}-ethoxy)-ethoxy]-ethoxy}-ethoxy)-ethoxy]-ethoxy}-ethoxy)-ethoxy]-ethoxy}-propionylamino)-propoxy]-benzyl}-ureido]-thiazole-4-carbonyl)-amino]-acetylamino]-3-pyridin-3-yl-propionic acid.

20. A pharmaceutical composition comprising a compound according to claim 1 and a pharmaceutically acceptable carrier.

21. A pharmaceutical composition comprising a compound according to claim 2 and a pharmaceutically acceptable carrier.

22. A pharmaceutical composition comprising a compound according to claim 3 and a pharmaceutically acceptable carrier.

23. A pharmaceutical com position comprising a compound according to claim 4 and a pharmaceutically acceptable cattier.

24. A pharmaceutical composition comprising a compound according to claim 5 and a pharmaceutically acceptable carrier.

25. A pharmaceutical composition comprising a compound according to claim 6 and a pharmaceutically acceptable carrier.

26. A pharmaceutical composition comprising a compound according to claim 7 and a pharmaceutically acceptable carrier.

27. A pharmaceutical composition comprising a compound according to claim 8 and a pharmaceutically acceptable carrier.

28. A pharmaceutical composition comprising a compound according to claim 9 and a pharmaceutically acceptable carrier.

29. A pharmaceutical composition comprising a compound according to claim 26 and a pharmaceutically acceptable carrier.

30. A pharmaceutical composition comprising a compound according to claim 11 and a pharmaceutically acceptable carrier.

31. A pharmaceutical composition comprising a compound according to claim 12 and a pharmaceutically acceptable carrier.

32. A pharmaceutical composition comprising a compound according to claim 13 and a pharmaceutically acceptable carrier.

33. A pharmaceutical composition comprising a compound according to claim 14 and a pharmaceutically acceptable carrier.

34. A method for improving delivery of nucleic acids to tumor cells expressing $\epsilon V\beta$ receptors, comprising the step of administering to a patient in need thereof, a therapeutically effective amount of a compound according to claim 1.

* * * * *